(12) United States Patent
Galetto

(10) Patent No.: US 9,944,702 B2
(45) Date of Patent: Apr. 17, 2018

(54) CD33 SPECIFIC CHIMERIC ANTIGEN RECEPTORS FOR CANCER IMMUNOTHERAPY

(71) Applicant: CELLECTIS, Paris (FR)

(72) Inventor: Roman Galetto, Paris (FR)

(73) Assignee: CELLECTIS, Paris (FR)

(*) Notice: Subject to any disclaimer, the term of this patent is extended or adjusted under 35 U.S.C. 154(b) by 0 days.

(21) Appl. No.: 15/301,686

(22) PCT Filed: Apr. 2, 2015

(86) PCT No.: PCT/EP2015/057331
§ 371 (c)(1),
(2) Date: Oct. 3, 2016

(87) PCT Pub. No.: WO2015/150526
PCT Pub. Date: Oct. 8, 2015

(65) Prior Publication Data
US 2017/0145094 A1    May 25, 2017

(30) Foreign Application Priority Data
Apr. 3, 2014    (DK) .................................. 2014 70171

(51) Int. Cl.
C07K 16/28      (2006.01)
C07K 14/725     (2006.01)
C07K 14/705     (2006.01)
A61K 39/00      (2006.01)

(52) U.S. Cl.
CPC ...... *C07K 16/2803* (2013.01); *C07K 14/7051* (2013.01); *C07K 14/70517* (2013.01); *A61K 2039/505* (2013.01); *C07K 2317/24* (2013.01); *C07K 2317/53* (2013.01); *C07K 2317/62* (2013.01); *C07K 2317/622* (2013.01); *C07K 2317/73* (2013.01); *C07K 2319/03* (2013.01)

(58) Field of Classification Search
CPC .................................................. C07K 16/2803
See application file for complete search history.

(56) References Cited

U.S. PATENT DOCUMENTS

2004/0058414 A1    3/2004   Queen et al.
2013/0309223 A1    11/2013  Sutherland et al.

FOREIGN PATENT DOCUMENTS

WO    WO 2004/043344 A2    5/2004
WO    WO 2011/036183 A2    3/2011
WO    WO 2012/079000 A1    6/2012

OTHER PUBLICATIONS

Dutour et al. (2012, Advances in Hematology, Article ID 683065, pp. 1-11).*
O'Hear et al. (2013, Blood, 122:1441, Abstract Only).*
Carpenter et al. (ePub Jan. 23, 2013, Clin. Cancer Res., vol. 19(8), pp. 2048-2060).*
"Treatment of Relapsed and/or Chemotherapy Refractory CD33 Positive Acute Myeloid Leukemia by CART-33 (CART33)," Feb. 1, 2015, [Online], May 20, 2013, pp. 1-2.
Campana et al, "4-1BB chimeric antigen receptors," Cancer Journal, Mar. 1, 2014, pp. 134-140, vol. 20, No. 2.
Curran et al, "Chimeric antigen receptors for T cell immunotherapy: current understanding and future directions," The Journal of Gene Medicine, Jun. 27, 2012, pp. 405-415, vol. 14, No. 6.
Dutour et al, "In Vitro and In Vivo Antitumor Effect of Anti-CD33 Chimeric Receptor-Expressing EBV-CTL against Acute Myeloid Leukemia," Advances in Hematology, Jan. 1, 2012, pp. 271-10, vol. 5, No. 3.
Finney et al., "Activation of Resting Human Primary T Cells with Chimeric Receptors: Costimulation from CD28, Inducible Costimulator, CD134, and CD137 in Series with Signals from the TCRzeta chain," The Journal of Immunology, The American Association of Immunolgists, Jan. 1, 2004, pp. 104-113, vol. 172 No. 1 US.
International Search Report issued in PCT/EP2015/057331 dated Oct. 12, 2015.
International Type Search Report issued in DK 201470171 dated Nov. 18, 2014.
Jensen et al, "Design and implementation of adoptive therapy with chimeric antigen receptor-modified T cells Authors' addresses," Immunological Reviews, Dec. 13, 2013, pp. 127-144, vol. 257, No. 1.
Marin et al, "Cytokine-induced killer cells for cell therapy of acute myeloid leukemia: improvement of their immune activity by expression of CD33-specific chimeric receptors," Haematologica, Aug. 16, 2010, pp. 2144-2152, vol. 95, No. 12.
Milone et al, "Chimeric Receptors Containing CD137 Signal Transduction Domains Mediate Enhanced Survival of T Cells and Increased Antileukemic Efficacy In Vivo," Molecular Therapy, Aug. 1, 2009, pp. 1453-1464, vol. 17, No. 8.
Pizzitola et al, "Chimeric antigen receptors against CD33/CD123 antigens efficiently target primary acute myeloid leukemia cells in vivo," Leukemia, Macmillan Press Ltd., Feb. 21, 2014, pp. 1596-1605, vol. 28, No. 8.

(Continued)

*Primary Examiner* — Thaian N Ton
*Assistant Examiner* — David A. Montanari
(74) *Attorney, Agent, or Firm* — Arent Fox LLP

(57) ABSTRACT

The present invention relates to Chimeric Antigen Receptors (CAR) that are recombinant chimeric proteins able to redirect immune cell specificity and reactivity toward selected membrane antigens, and more particularly in which extracellular ligand binding is a scFV derived from a CD33 monoclonal antibody, conferring specific immunity against CD33 positive cells. The engineered immune cells endowed with such CARs are particularly suited for treating lymphomas and leukemia.

29 Claims, 8 Drawing Sheets

(56) References Cited

OTHER PUBLICATIONS

Wang et al, "Treatment of CD33-directed Chimeric Antigen Receptor-modified T Cells in One Patient With Relapsed and Refractory Acute Myeloid Leukemia," Molecular Therapy, Sep. 23, 2014, pp. 184-191, vol. 23, No. 1.

* cited by examiner

CD33 SPECIFIC CHIMERIC ANTIGEN RECEPTORS FOR CANCER IMMUNOTHERAPY

CROSS-REFERENCE TO RELATED APPLICATIONS

This application is a National Stage entry under 35 U.S.C. § 371 of International Application No. PCT/EP2015/057331, filed Apr. 2, 2015, which claims priority to Danish Patent Application No. PA201470171, filed Apr. 3, 2014. The disclosure of the prior applications are hereby incorporated in their entirety by reference.

FIELD OF THE INVENTION

The present invention relates to Chimeric Antigen Receptors (CAR) that are recombinant chimeric proteins able to redirect immune cell specificity and reactivity toward CD33, a cell surface glycoprotein found on most myeloid cells and used to diagnose acute myeloid Leukemia (AML) in patients. The CARs according to the invention are particularly useful to treat malignant cells bearing CD33, when expressed in T-cells or NK cells. The resulting engineered immune cells display high level of specificity toward malignant cells, conferring safety and efficiency for immunotherapy.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T-cell cytotoxicity. However, they failed to provide prolonged expansion and anti-tumor activity in vivo. Signaling domains from co-stimulatory molecules, as well as transmembrane and hinge domains have been added to form CARs of second and third generations, leading to some successful therapeutic trials in humans, where T-cells could be redirected against malignant cells expressing CD19 (June et al., 2011). However, the particular combination of signaling domains, transmembrane and co-stimulatory domains used with respect to CD19 ScFv, was rather antigen-specific and cannot be expanded to any antigen markers.

Acute myeloid leukaemia (AML) is the second most common acute leukaemia with approximately 13,300 new cases per year in the United States and 8,800 annual deaths. The commonly applied therapy of leukaemic diseases includes irradiation and/or chemotherapy. Furthermore, under certain circumstances, the additional possibility of bone marrow transplantation is regarded suitable. However, these therapies are relatively toxic to the patient and very often do not lead to a complete cure from the disease. Thus, although a complete remission can be achieved for 65-80% of patients receiving chemotherapy, most of these patients relapse (Cros et al., 2004) because the cells that survived the chemotherapy are enriched in AML leukaemia stem cells (AML-LSCs), and constitute a particularly dangerous reservoir of cells capable of re-expanding and causing a relapse. Leukaemia stem cells have been particularly well characterized for acute myeloid leukaemia. AML-LSCs express a characteristic set of cell-surface antigens including among others CD33. Patients older than 60 years have a poor prognosis with only 10% to 15% of 4-year disease-free survival (Gardin et al., 2007). This high relapse rate for AML patients and the poor prognosis for older patients highlight the urgent need for novel therapeutics preferentially targeting CD33+ cells.

CD33 (Sialic acid-binding Ig-like lectin 3) or SIGLEC3, referred to as P20138 under the UniProtKB/Swiss-Prot protein database, is a transmembrane receptor expressed on cells of myeloid lineage. It is usually considered myeloid-specific, but it can also be found on some lymphoid cells. It binds sialic acids, therefore is a member of the SIGLEC family of lectins.

In the past, different approaches have been used to develop unconjugated monoclonal antibodies with antitumor activity against CD33. However these attempts failed to address malignant cells specifically.

In 2000 Gemtuzumabozogamicin (Mylotarg™, GO), a calicheamicinconjugated humanized anti-CD33 monoclonal antibody, was approved by the American Food and Drug Administration (FDA) for treating patients older than 60 years with refractory or relapsed AML. However this was withdrawn from the market on Jun. 21, 2010; GO consisted of a humanized anti-CD33 IgG-antibody, chemically coupled to the cytotoxic agent calicheamicin. Post-approval study (SWOG 50106) raised concerns about the product's safety, while other clinical trials (British MRC AML-15 and the HOVON-43 trials) failed to demonstrate any clinical benefit (Maniecki et al., 2011). Side effects were found to include hepatic veno-occlusive disease, pulmonary toxicity and severe hypersensitivity reactions, whereas in vitro studies revealed antigen-independent cytotoxicities towards CD33 negative cell lines (Schwemmlein of al, 2006).

More recently, tri-specific polypeptide molecules combining immunoglobulin domains from CD123, CD16 and CD33 antibodies were proposed (WO2011/070109) to obviate the specificity issues previously encountered with therapeutics targeting CD33.

As an alternative to the previous strategies, the present invention provides with CD33 specific CARs, which can be expressed in immune cells to target CD33+ malignant cells with significant clinical advantage.

SUMMARY OF THE INVENTION

The inventors have generated CD33 specific CAR having different structure and comprising different scFV derived from different CD33 specific antibodies. Preferred CAR polypeptides of the invention comprise an amino acid sequence selected from SEQ ID NO.19 to 42. More preferred CAR polypeptides of the invention comprise an amino acid sequence of SEQ ID NO. 68, or with at least 80% identity with SEQ ID NO. 68. Following non-specific activation in vitro (e.g. with anti CD3/CD28 coated beads and recombinant IL2), T-cells from donors have been transformed with polynucleotides expressing these CARs using viral transduction. In certain instances, the T-cells were further engineered to create non-alloreactive T-cells, more especially by disruption of a component of TCR (αβ-T-Cell receptors) to prevent Graft versus host reaction and even more especially by disruption of a component of a TCR (αβ-T-Cell receptors) and of a CD33 gene.

The resulting engineered T-cells displayed reactivity in-vitro against CD33 positive cells to various extend, showing that the CARs of the present invention contribute to antigen dependent activation, and also proliferation, of the T-cells, making them useful for immunotherapy.

The polypeptides and polynucleotide sequences encoding the CARs of the present invention are detailed in the present specification.

The engineered immune cells of the present invention are particularly useful for therapeutic applications such as B-cell lymphoma or leukemia treatments.

TABLE 1

Sequence of the different CAR components

Figure 1:
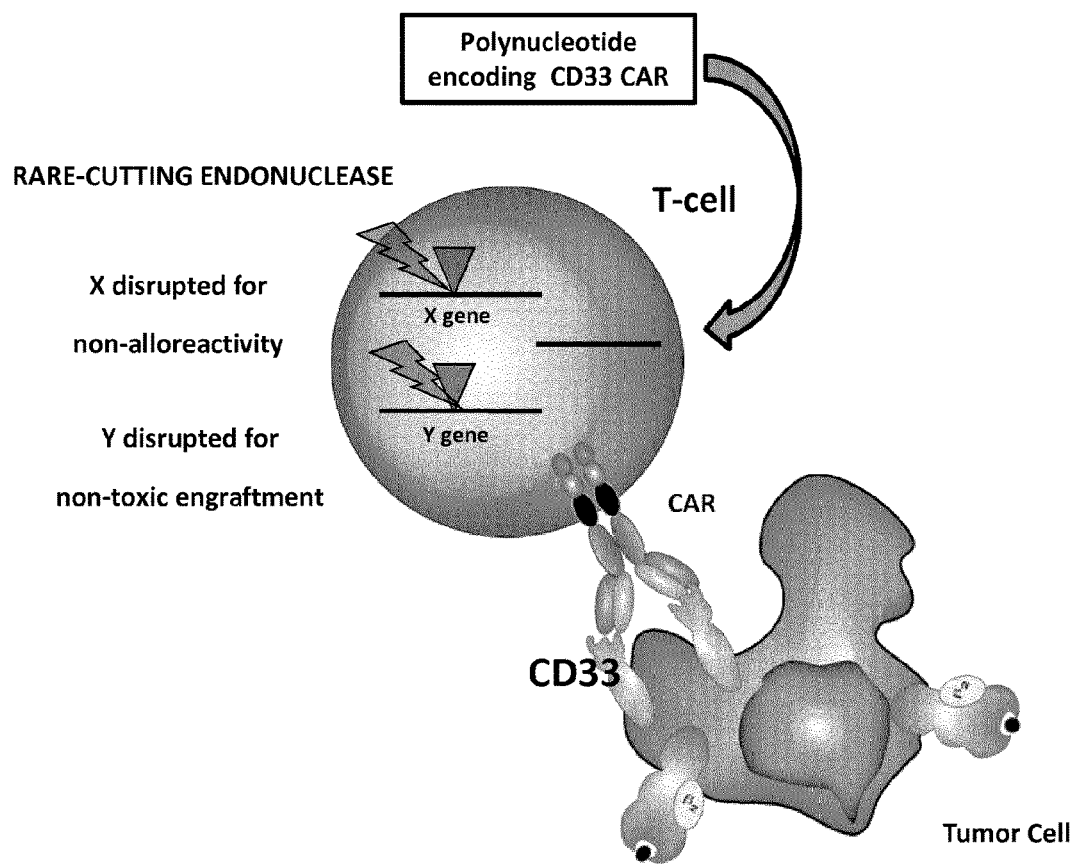
FIG. 1: Schematic representation of an engineered immune cell according to the invention. The engineered immune cell presented in this figure is a T-cell transduced with a retroviral polypeptide encoding CAR. This T-cell is further engineered to allow a better and safer engraftment into the patient, which is optional within the frame of the present invention. X gene may be for instance a gene expressing a component of TCR (TCRalpha or TCRbeta), Y may be a gene involved into the sensitivity of T-cells to immune-suppressive drugs like CD52 (with respect to Campath) or HPRT (with respect to 6-Thioguanine).

| Functional domains | SEQ ID # | Raw amino acid sequence |
|---|---|---|
| CD8α signal peptide | SEQ ID NO. 1 | MALPVTALLLPLALLLHAARP |
| Alternative signal peptide | SEQ ID NO. 2 | METDTLLLWVLLLWVPGSTG |
| FcγRIIIα hinge | SEQ ID NO. 3 | GLAVSTISSFFPPGYQ |
| CD8α hinge | SEQ ID NO. 4 | TTTPAPRPPTPAPTIASQPLSLRPEACRPAAGGAVHTRGLDFACD |
| IgG1 hinge | SEQ ID NO. 5 | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| CD8α transmembrane domain | SEQ ID NO. 6 | IYIWAPLAGTCGVLLLSLVITLYC |
| 41BB transmembrane domain | SEQ ID NO. 7 | IISFFLALTSTALLFLLFFLTLRFSVV |

TABLE 1 -continued

Sequence of the different CAR components

| Functional domains | SEQ ID # | Raw amino acid sequence |
|---|---|---|
| 41BB intracellular domain | SEQ ID NO. 8 | KRGRKKLLYIFKQPFMRPVQTTQEEDGCSCRFPE EEEGGCEL |
| CD3ζ intracellular domain | SEQ ID NO. 9 | RVKFSRSADAPAYQQGQNQLYNELNLGRREEY DVLDKRRGRDPEMGGKPRRKNPQEGLYNELQK DKMAEAYSEIGMKGERRRGKGHDGLYQGLSTA TKDTYDALHMQALPPR |
| Linker | SEQ ID NO. 10 | GGGGSGGGGSGGGGS |

TABLE 2

Sequence of the different CAR components

| ScFv sequences | SEQ ID # | Raw amino acid sequence |
|---|---|---|
| M195 heavy chain variable region | SEQ ID NO. 11 | EVQLQQSGPELVKPGASVKISCKASGYTFTDYN MHWVKQSHGKSLEWIGYIYPYNGGTGYNQKF KSKATLTVDNSSSTAYMDVRSLTSEDSAVYYCA RGRPAMDYWGQGTSVTVS |
| M195 light chain variable region | SEQ ID NO. 12 | DIVLTQSPASLAVSLGQRATISCRASESVDNYGI SFMNWFQQKPGQPPKLLIYAASNQGSGVPAR FSGSGSGTDFSLNIHPMEEDDTAMYFCQQSKE VPWTFGGGTKLEIK |
| M2H12 heavy chain variable region | SEQ ID NO. 13 | QVQLQQSGPELVRPGTFVKISCKASGYTFTNYD INWVNQRPGQGLEWIGWIYPGDGSTKYNEKF KAKATLTADKSSSTAYLQLNNLTSENSAVYFCAS GYEDAMDYWGQGTSVTVSS |
| M2H12 light chain variable region | SEQ ID NO. 14 | DIKMTQSPSSMYASLGERVIINCKASQDINSYLS WFQQKPGKSPKTLIYRAN RLVDGVPSRFSGSG SGQDYSLTISSLEYEDMGIYYCLQYDEFPLTFGA GTKLELKR |
| DRB2 heavy chain variable region | SEQ ID NO. 15 | EVKLQESGPELVKPGASVKMSCKASGYKFTDYV VHWLKQKPGQGLEWIGYINPYNDGTKYNEKF KGKATLTSDKSSSTAYMEVSSLTSEDSAVYYCA RDYRYEVYGMDYWGQGTSVTVSS |
| DRB2 light chain variable region | SEQ ID NO. 16 | DIVLTQSPTIMSASPGERVTMTCTASSSVNYIH WYQQKSGDSPLRWIFDTSKVASGVPARFSGSG SGTSYSLTISTMEAEDAATYYCQQWRSYPLTFG DGTRLELKRADAAPTVS |
| My9-6 heavy chain variable region | SEQ ID NO. 17 | QVQLQQPGAEVVKPGASVKMSCKASGYTFTS YYIHWIKQTPGQGLEWVGVIYPGNDDISYNQK FKGKATLTADKSSTTAYMQLSSLTSEDSAVYYC AREVRLRYFDVWGAGTTVTSS |
| My9-6 light chain variable region | SEQ ID NO. 18 | NIMLTQSPSSLAVSAGEKVTMSCKSSQSVFFSS SQKNYLAWYQQ1PGQSPKWYWASTRESGVP DRFTGSGSGTDFTLTISSVQSEDLAIYYCHQYLS SRTFGGGTKLEIKR |

TABLE 3

CAR of structure V-1

| CAR Designation V-1 | signal peptide (optional) | VH | VL | FcγRIIIα hinge | CD8α TM | 41BB-IC | CD3ζ CD |
|---|---|---|---|---|---|---|---|
| M195-1 (SEQ ID NO. 19) | SEQ ID NO. 1 | SEQ ID NO. 11 | SEQ ID NO. 12 | SEQ ID NO. 3 | SEQ ID NO. 6 | SEQ ID NO. 8 | SEQ ID NO. 9 |
| M2H12-1 (SEQ ID NO. 20) | SEQ ID NO. 1 | SEQ ID NO. 13 | SEQ ID NO. 14 | SEQ ID NO. 3 | SEQ ID NO. 6 | SEQ ID NO. 8 | SEQ ID NO. 9 |

TABLE 3-continued

CAR of structure V-1

CAR Structure

| CAR Designation V-1 | signal peptide (optional) | VH | VL | FcγRIIIα hinge | CD8α TM | 41BB-IC | CD3ζ CD |
|---|---|---|---|---|---|---|---|
| DRB2-1 (SEQ ID NO. 21) | SEQ ID NO. 1 | SEQ ID NO. 15 | SEQ ID NO. 16 | SEQ ID NO. 3 | SEQ ID NO. 6 | SEQ ID NO. 8 | SEQ ID NO. 9 |
| My9-6-1 (SEQ ID NO. 22) | SEQ ID NO. 1 | SEQ ID NO. 17 | SEQ ID NO. 18 | SEQ ID NO. 3 | SEQ ID NO. 6 | SEQ ID NO. 8 | SEQ ID NO. 9 |

TABLE 4

CAR of structure V-2

CAR Structure

| CAR Designation V-2 | signal peptide (optional) | VH | VL | FcγRIIIα hinge | 41BB-TM | 41BB-IC | CD3ζ CD |
|---|---|---|---|---|---|---|---|
| M195-2 (SEQ ID NO. 23) | SEQ ID NO. 1 | SEQ ID NO. 11 | SEQ ID NO. 12 | SEQ ID NO. 3 | SEQ ID NO. 7 | SEQ ID NO. 8 | SEQ ID NO. 9 |
| M2H12-2 (SEQ ID NO. 24) | SEQ ID NO. 1 | SEQ ID NO. 13 | SEQ ID NO. 14 | SEQ ID NO. 3 | SEQ ID NO. 7 | SEQ ID NO. 8 | SEQ ID NO. 9 |
| DRB2-2 (SEQ ID NO. 25) | SEQ ID NO. 1 | SEQ ID NO. 15 | SEQ ID NO. 16 | SEQ ID NO. 3 | SEQ ID NO. 7 | SEQ ID NO. 8 | SEQ ID NO. 9 |
| My9-6-2 (SEQ ID NO. 26) | SEQ ID NO. 1 | SEQ ID NO. 17 | SEQ ID NO. 18 | SEQ ID NO. 3 | SEQ ID NO. 7 | SEQ ID NO. 8 | SEQ ID NO. 9 |

TABLE 5

CAR of structure V-3

CAR Structure

| CAR Designation V-3 | signal peptide (optional) | VH | VL | CD8α hinge | CD8α TM | 41BB-IC | CD3ζ CD |
|---|---|---|---|---|---|---|---|
| M195-3 (SEQ ID NO. 27) | SEQ ID NO. 1 | SEQ ID NO. 11 | SEQ ID NO. 12 | SEQ ID NO. 4 | SEQ ID NO. 6 | SEQ ID NO. 8 | SEQ ID NO. 9 |
| M2H12-3 (SEQ ID NO. 28) | SEQ ID NO. 1 | SEQ ID NO. 13 | SEQ ID NO. 14 | SEQ ID NO. 4 | SEQ ID NO. 6 | SEQ ID NO. 8 | SEQ ID NO. 9 |
| DRB2-3 (SEQ ID NO. 29) | SEQ ID NO. 1 | SEQ ID NO. 15 | SEQ ID NO. 16 | SEQ ID NO. 4 | SEQ ID NO. 6 | SEQ ID NO. 8 | SEQ ID NO. 9 |
| My9-6-3 (SEQ ID NO. 30) | SEQ ID NO. 1 | SEQ ID NO. 17 | SEQ ID NO. 18 | SEQ ID NO. 4 | SEQ ID NO. 6 | SEQ ID NO. 8 | SEQ ID NO. 9 |

TABLE 6

CAR of structure V-4

CAR Structure

| CAR Designation V-4 | signal peptide (optional) | VH | VL | CD8α hinge | 41BB-TM | 41BB-IC | CD3ζ CD |
|---|---|---|---|---|---|---|---|
| M195-4 (SEQ ID NO. 31) | SEQ ID NO. 1 | SEQ ID NO. 11 | SEQ ID NO. 12 | SEQ ID NO. 4 | SEQ ID NO. 7 | SEQ ID NO. 8 | SEQ ID NO. 9 |
| M2H12-4 (SEQ ID NO. 32) | SEQ ID NO. 1 | SEQ ID NO. 13 | SEQ ID NO. 14 | SEQ ID NO. 4 | SEQ ID NO. 7 | SEQ ID NO. 8 | SEQ ID NO. 9 |
| DRB2-4 (SEQ ID NO. 33) | SEQ ID NO. 1 | SEQ ID NO. 15 | SEQ ID NO. 16 | SEQ ID NO. 4 | SEQ ID NO. 7 | SEQ ID NO. 8 | SEQ ID NO. 9 |
| My9-6-5 (SEQ ID NO. 34) | SEQ ID NO. 1 | SEQ ID NO. 17 | SEQ ID NO. 18 | SEQ ID NO. 4 | SEQ ID NO. 7 | SEQ ID NO. 8 | SEQ ID NO. 9 |

TABLE 7

CAR of structure V-5

| CAR Designation V-5 | signal peptide (optional) | VH | VL | IgG1 hinge | CD8α TM | 41BB-IC | CD3ζζ CD |
|---|---|---|---|---|---|---|---|
| M195-5 (SEQ ID NO. 35) | SEQ ID NO. 1 | SEQ ID NO. 11 | SEQ ID NO. 12 | SEQ ID NO. 5 | SEQ ID NO. 6 | SEQ ID NO. 8 | SEQ ID NO. 9 |
| M2H12-5 (SEQ ID NO. 36) | SEQ ID NO. 1 | SEQ ID NO. 13 | SEQ ID NO. 14 | SEQ ID NO. 5 | SEQ ID NO. 6 | SEQ ID NO. 8 | SEQ ID NO. 9 |
| DRB2-5 (SEQ ID NO. 37) | SEQ ID NO. 1 | SEQ ID NO. 15 | SEQ ID NO. 16 | SEQ ID NO. 5 | SEQ ID NO. 6 | SEQ ID NO. 8 | SEQ ID NO. 9 |
| My9-6-5 (SEQ ID NO. 38) | SEQ ID NO. 1 | SEQ ID NO. 17 | SEQ ID NO. 18 | SEQ ID NO. 5 | SEQ ID NO. 6 | SEQ ID NO. 8 | SEQ ID NO. 9 |

TABLE 8

CAR of structure V-6

| CAR Designation V-6 | signal peptide (optional) | VH | VL | IgG1 hinge | 41BB-TM | 41BB-IC | CD3ζ CD |
|---|---|---|---|---|---|---|---|
| M195-6 (SEQ ID NO. 39) | SEQ ID NO. 1 | SEQ ID NO. 11 | SEQ ID NO. 12 | SEQ ID NO. 5 | SEQ ID NO. 7 | SEQ ID NO. 8 | SEQ ID NO. 9 |
| M2H12-6 (SEQ ID NO. 40) | SEQ ID NO. 1 | SEQ ID NO. 13 | SEQ ID NO. 14 | SEQ ID NO. 5 | SEQ ID NO. 7 | SEQ ID NO. 8 | SEQ ID NO. 9 |
| DRB2-6 (SEQ ID NO. 41) | SEQ ID NO. 1 | SEQ ID NO. 15 | SEQ ID NO. 16 | SEQ ID NO. 5 | SEQ ID NO. 7 | SEQ ID NO. 8 | SEQ ID NO. 9 |
| My9-6-6 (SEQ ID NO. 42) | SEQ ID NO. 1 | SEQ ID NO. 17 | SEQ ID NO. 18 | SEQ ID NO. 5 | SEQ ID NO. 7 | SEQ ID NO. 8 | SEQ ID NO. 9 |

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

Figure 2:
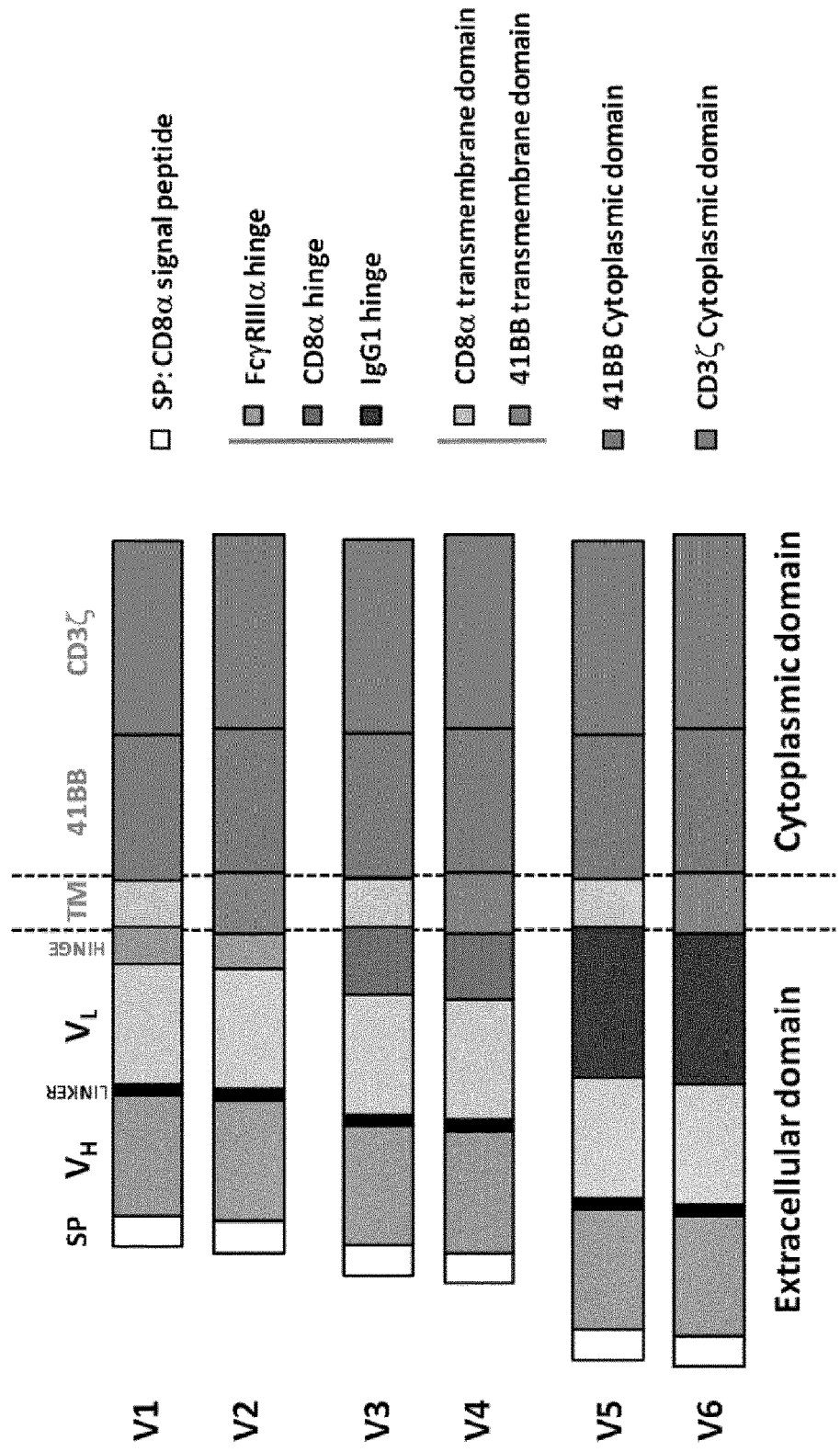
FIG. 2: Schematic representation of the different CAR Architecture (V1 to V6).

The present invention provides a CD33 specific chimeric antigen receptor (CAR) having at least 80% identity with one of the polypeptide structure selected from V1, V3 and V5 as illustrated in FIG. 2, said structure comprising:
(a) an extra cellular ligand binding-domain comprising VH and VL from a monoclonal anti-CD33 antibody,
(b) a hinge selected from FcRIIIα hinge, CD8α hinge, and IgG1 hinge,
(c) a CD8α transmembrane domain and
(d) a cytoplasmic domain including a CD3 zeta signaling domain and a co-stimulatory domain from 4-1BB.

In a preferred embodiment, the present invention provides a CD33 specific CAR as above wherein said structure V3 comprises a CD8α hinge and a CD8α transmembrane domain.

The present invention provides a CD33 specific CAR as above, wherein said CD8α hinge has at least 80% identity with SEQ ID NO.4.

The present invention provides a CD33 specific CAR as above, which comprises a polypeptide sequence having at least 80% identity with SEQ ID NO. 27, SEQ ID NO.28, SEQ ID NO.29 and SEQ ID NO.30.

In an embodiment, the present invention provides a CD33 specific CAR as above wherein said structure V1 comprises a FcγRIIIα hinge and a CD8α transmembrane domain.

The present invention provides a CD33 specific CAR as above, wherein said FcγRIIIα hinge has at least 80% identity with SEQ ID NO.3.

The present invention provides a CD33 specific CAR as above, which comprises a polypeptide sequence having at least 80% identity with SEQ ID NO. 19, SEQ ID NO.20, SEQ ID NO.21 and SEQ ID NO.22.

In an embodiment, the present invention provides a CD33 specific CAR as above, wherein said structure V5 comprises an IgG1 hinge and a CD8α transmembrane domain.

The present invention provides a CD33 specific CAR as above, wherein said IgG1 hinge has at least 80% identity with SEQ ID NO.5.

The present invention provides a CD33 specific CAR as above, which comprises a polypeptide sequence having at least 80% identity with SEQ ID NO. 35, SEQ ID NO.36, SEQ ID NO.37 and SEQ ID NO.38.

The present invention provides a CD33 specific CAR as above, wherein said VH has at least 80% identity with a polypeptide sequence selected from SEQ ID NO. 11, SEQ ID NO. 13, SEQ ID NO. 15 and SEQ ID NO. 17 and said VL has at least 80% identity with a polypeptide sequence selected from SEQ ID NO. 12, SEQ ID NO. 14, SEQ ID NO. 16 and SEQ ID NO. 18.

The present invention provides a CD33 specific CAR as above, wherein co-stimulatory domain from 4-1BB has at least 80% identity with SEQ ID NO.8.

The present invention provides a CD33 specific CAR as above, wherein said CD3 zeta signaling domain has at least 80% identity with SEQ ID NO. 9.

The present invention provides a CD33 specific CAR as above, wherein said CD8α transmembrane domain has at least 80% identity with SEQ ID NO.6.

The present invention provides a CD33 specific CAR as above, further comprising a signal peptide.

The present invention provides a CD33 specific CAR as above, wherein said signal peptide has at least 80% sequence identity with SEQ ID NO.1 or SEQ ID NO.2.

In one embodiment the present invention provides a CD33 specific CAR as above, which comprises a polypeptide sequence having at least 80% identity with SEQ ID NO. 48 to 71 SEQ ID NO. 48, preferably at least 80% identity with SEQ ID NO. 48, SEQ ID NO. 50, SEQ ID NO. 52, SEQ ID NO. 54, SEQ ID NO. 56, SEQ ID NO. 58, SEQ ID NO. 66, SEQ ID NO. 68, SEQ ID NO. 70, more preferably at least 80% identity with SEQ ID NO. 66, SEQ ID NO. 68, SEQ ID NO. 70.

The present invention provides a CD33 specific CAR as above further comprising another extracellular ligand binding domain which is not specific for CD33.

In one aspect the present invention provides a polynucleotide encoding a CAR according to any one of the embodiments above.

In one aspect the present invention provides an expression vector comprising a polynucleotide as above.

In one aspect, the present invention provides an engineered immune cell expressing at the cell surface membrane a CD33 specific CAR according to any one of the above.

The present invention provides an engineered immune cell as above, derived from inflammatory T-lymphocytes, cytotoxic T-lymphocytes, regulatory T-lymphocytes or helper T-lymphocytes.

The present invention provides an engineered immune cell as above, wherein expression of TCR is suppressed.

The present invention provides an engineered immune cell as above, wherein expression of CD33 is suppressed.

The present invention provides an engineered immune cell as above, wherein said engineered immune cell is modified to be resistant to at least one immune suppressive or chemotherapy drug.

The present invention provides an engineered immune cell as above, for use in therapy.

The present invention provides an engineered immune cell for use in therapy as above, wherein the patient is a human.

The present invention provides an engineered immune cell for use in therapy as above, wherein the condition is a pre-malignant or malignant cancer condition characterized by CD33-expressing cells.

The present invention provides an engineered immune cell for use in therapy as above, wherein the condition is a condition which is characterized by an overabundance of CD33-expressing cells.

The present invention provides an engineered immune cell for use in therapy as above wherein the condition is a hematological cancer condition.

The present invention provides an engineered immune cell for use in therapy as above, wherein the haematological cancer condition is leukemia.

The present invention provides an engineered immune cell for use in therapy as above, wherein said leukemia is selected from the group consisting of acute myelogenous leukemia (AML), chronic myelogenous leukemia, melodysplastic syndrome, acute lymphoid leukemia, chronic lymphoid leukemia, and myelodysplastic syndrome.

The present invention provides an engineered immune cell for use in therapy as above, wherein said leukemia is acute myelogenous leukemia (AML).

The present invention provides an engineered immune cell for use in therapy as above, wherein said hematological cancer is a malignant lymphoproliferative disorder.

The present invention provides an engineered immune cell for use in therapy as above, wherein said malignant lymphoproliferative disorder is a lymphoma.

The present invention provides an engineered immune cell for use in therapy as above, wherein said lymphoma is selected from the group consisting of multiple myeloma, non-Hodgkin's lymphoma, Burkitt's lymphoma, and follicular lymphoma (small cell and large cell).

In one aspect, the present invention provides a method of impairing a hematologic cancer cell comprising contacting said hematologic cancer cell with an engineered immune cell as above in an amount effective to cause impairment of said cancer cell.

In one aspect, the present invention provides a method of engineering an immune cell comprising:
  (a) Providing an immune cell,
  (b) Expressing at the surface of said cell at least one CD33 specific chimeric antigen receptor as described above.

The present invention provides a method of engineering an immune cell as above comprising:
  (a) Providing an immune cell,
  (b) Introducing into said cell at least one polynucleotide encoding said CD33 specific chimeric antigen receptor, as above
  (c) Expressing said polynucleotide into said cell, optionally expressing said CD33 specific chimeric antigen receptor.

The present invention provides a method of engineering an immune cell as above further comprising:
(d) Inhibiting TRC expression and/or CD33 expression.

In one embodiment, the immune cell provided for the step (a) of the method described above is an immune cell wherein the expression of TRC and/or CD33 at the cell surface is inhibited, and optionally resistant to at least one drug used to treat a cancer, in particular AML.

The present invention provides a method of engineering an immune cell as above further comprising:
(a) Introducing at least one other chimeric antigen receptor which is not specific for CD33.

The present invention also provides a method of treating a subject in need thereof comprising:
(a) Providing an immune cell expressing at the surface a CD33 specific Chimeric Antigen Receptor according to any one of the above;
(b) Administrating said immune cells to said patient.

In one aspect the present invention provides a method as above, wherein said immune cell is provided from a donor.

The present invention provides a method of treating a subject in need thereof as above wherein said immune cell (to be engineered according to the invention) is provided from the patient himself.

CD33 Specific Chimeric Antigen Receptors

The present invention relates to new designs of anti-CD33 chimeric antigen receptor (CAR or CD33 CAR or CD33 specific CAR or anti-CD33 CAR) comprising an extracellular ligand-binding domain, a transmembrane domain and a signaling transducing domain.

More precisely, the present invention relates to new CD33 specific CAR comprising an extra cellular ligand binding-domain comprising a VH and a VL from a monoclonal anti-CD33 antibody, a hinge selected from FcRIIIα hinge, CD8alpha hinge and IgG1 hinge, a CD8α transmembrane domain and a cytoplasmic domain including a CD3 zeta signaling domain and a co-stimulatory domain from 4-1BB.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. In a preferred embodiment, said extracellular ligand-binding domain comprises a single chain antibody fragment (scFv) comprising the light ($V_L$) and the heavy ($V_H$) variable fragment of a target antigen specific monoclonal anti CD-33 antibody joined by a flexible linker. Said $V_L$ and $V_H$ are preferably selected from the antibodies referred to as M195, m2H12, DRB2 and My9-6 as indicated in Table 2.

In an even more preferred embodiment said $V_L$ and $V_H$ comprises SEQ ID NO 17 and 18, optionally humanized.

They are preferably linked together by a flexible linker comprising for instance the sequence SEQ ID NO.10. In other words, said CARs preferentially comprise an extracellular ligand-binding domain comprising a polypeptide sequence displaying at least 90%, 95%, 97% or 99% identity with an amino acid sequence selected from the group consisting of SEQ ID NO: 11 to SEQ ID NO: 18.

In one embodiment, said CAR of the invention preferentially comprises an extracellular ligand-biding domain comprising a polypeptide of SEQ ID NO: 11 and SEQ ID NO: 12.

In one embodiment, said CAR of the invention preferentially comprises an extracellular ligand-biding domain comprising a polypeptide of SEQ ID NO: 13 and SEQ ID NO: 14.

In one embodiment, said CAR of the invention preferentially comprises an extracellular ligand-biding domain comprising a polypeptide of SEQ ID NO: 15 and SEQ ID NO: 16.

In one embodiment, said CAR of the invention preferentially comprises an extracellular ligand-biding domain comprising a polypeptide of SEQ ID NO: 17 and SEQ ID NO: 18.

By the term "recombinant antibody" as used herein, is meant an antibody or antibody fragment which is generated using recombinant DNA technology, such as, for example, an antibody or antibody fragment expressed by a bacteriophage, a yeast expression system or a mammalian cell expression system. The term should also be construed to mean an antibody or antibody fragment which has been generated by the synthesis of a DNA molecule encoding the antibody or antibody fragment and which DNA molecule expresses an antibody or antibody fragment protein, or an amino acid sequence specifying the antibody or antibody fragment, wherein the DNA or amino acid sequence has been obtained using recombinant or synthetic DNA or amino acid sequence technology which is available and well known in the art.

As used herein, the term "conservative sequence modifications" or "humanization" is intended to refer to amino acid modifications that do not significantly affect or alter the characteristics of the CAR (as compared to that of a CAR constructed using the original anti-CD33) and/or that do not significantly affect the activity of the CAR containing the modified amino acid sequence and reduce or abolish a human antimouse antibody (HAMA) response. Such conservative modifications include amino acid substitutions, additions and deletions in said antibody fragment in said CAR and/or any of the other parts of said CAR molecule. Modifications can be introduced into an antibody, into an antibody fragment or in any of the other parts of the CAR molecule of the invention by standard techniques known in the art, such as site-directed mutagenesis, PCR-mediated mutagenesis or by employing optimized germline sequences. Accordingly, the present invention provides a (humanized) CD33 CAR, wherein VH has at least 80% identity with SEQ ID NO 11, SEQ ID NO13, SEQ ID NO15, or SEQ ID NO17 and VL has at least 80% identity with SEQ ID NO 12, SEQ ID NO14, SEQ ID NO16, or SEQ ID NO18.

In one embodiment, said CAR of the invention preferentially comprises an extracellular ligand-biding domain comprising a polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% identity with an amino acid sequence of SEQ ID NO: 11 and SEQ ID NO 12.

In one embodiment, said CAR of the invention preferentially comprises an extracellular ligand-biding domain comprising a polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% identity with an amino acid sequence of SEQ ID NO 13 and SEQ ID NO 14.

In one embodiment, said CAR of the invention preferentially comprises an extracellular ligand-biding domain comprising a polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% identity with an amino acid sequence of SEQ ID NO 15 and SEQ ID NO 16.

In one embodiment, said CAR of the invention preferentially comprises an extracellular ligand-biding domain comprising a polypeptide sequence having at least 80%, 81%, 82%, 83%, 84%, 85%, 86%, 87%, 88%, 89%, 90%, 91%, 92%, 93%, 94%, 95%, 96%, 97%, 98%, or 99% identity with an amino acid sequence of SEQ ID NO 17 and SEQ ID NO 18.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind CD 33 using the functional assays described herein.

The signal transducing domain or intracellular signaling domain of a CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97%-99% or 100% sequence identity with amino acid sequence selected from the group consisting of (SEQ ID NO: 9).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank: AAA53133.) and CD28 (NP_006130.1). In particular the signal transduction domain of the CAR of the present invention comprises amino acid sequence which comprises at least 70%, preferably at least 80%, more preferably at least 90%, 95% 97% 699% or 100% sequence identity with amino acid sequence selected from the group consisting of SEQ ID NO: 8.

A CAR according to the present invention is expressed on the surface membrane of the cell. Thus, such CAR further comprises a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T-cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1) The transmembrane domain can further comprise a hinge region between said extracellular ligand-binding domain and said transmembrane domain. The term "hinge region" used herein generally means any oligo- or polypeptide that functions to link the transmembrane domain to the extracellular ligand-binding domain. In particular, hinge region are used to provide more flexibility and accessibility for the extracellular ligand-binding domain. A hinge region may comprise up to 300 amino acids, preferably 10 to 100 amino acids and most preferably 25 to 50 amino acids. Hinge region may be derived from all or part of naturally occurring molecules, such as from all or part of the extracellular region of CD8, CD4 or CD28, or from all or part of an antibody constant region. Alternatively the hinge region may be a synthetic sequence that corresponds to a naturally occurring hinge sequence, or may be an entirely synthetic hinge sequence. In a preferred embodiment said hinge domain comprises a part of human CD8 alpha chain, FcγRIIIα receptor or IgG1 respectively referred to in this specification as SEQ ID NO. 3, SEQ ID NO. 4 and SEQ ID NO.5, or hinge polypeptides which display preferably at least 80%, more preferably at least 90%, 95% 97% 99% or 100% sequence identity with these polypeptides.

A CAR according to the invention generally further comprises a transmembrane domain (TM) more particularly selected from CD8α and 4-1BB, showing identity with the polypeptides of SEQ ID NO. 6 or 7.

A CAR according to the invention generally comprises a transmembrane domain (TM) from CD8α showing 90%, 91%, 92%, 93%, 94%, 95%, 96%, 97%, 98%, 99% or 100% identity with the polypeptide of SEQ ID NO. 6. In a preferred embodiment, a CAR according to the invention generally further comprises a transmembrane domain (TM) from CD8α showing 100% identity with the polypeptide of SEQ ID NO. 6.

Downregulation or mutation of target antigens is commonly observed in cancer cells, creating antigen-loss escape variants. Thus, to offset tumor escape and render immune cell more specific to target, the CD33 specific CAR according to the invention can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

The present invention provides a CD33 specific CAR having one of the polypeptide structure selected from V1 to V6 as illustrated in FIG. 2, said structure comprising an extra cellular ligand binding-domain comprising VH and VL from a monoclonal anti-CD33 antibody, a hinge selected from FcRIIIα hinge, CD8α hinge, and IgG1 hinge, a CD8α transmembrane domain and a cytoplasmic domain including a CD3 zeta signaling domain and a co-stimulatory domain from 4-1BB.

The present invention provides a CD33 specific CAR having one of the polypeptide structure selected from V1, V3 and V5 as illustrated in FIG. 2, said structure comprising an extra cellular ligand binding-domain comprising VH and VL from a monoclonal anti-CD33 antibody, a hinge selected from a FcRIIIα hinge and CD8 alpha (a) hinge, a CD8α transmembrane domain and a cytoplasmic domain including a CD3 zeta signaling domain and a co-stimulatory domain from 4-1BB.

The present invention provides a CD33 CAR comprising a polypeptide sequence selected from the group consisting of SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59; SEQ ID NO: 60, SEQ ID NO: 61, SEQ ID NO: 62, SEQ ID NO: 63, SEQ ID NO: 64, SEQ ID NO: 65? SEQ ID NO: 66, SEQ ID NO: 67, SEQ ID NO: 68, SEQ ID NO: 69, SEQ ID NO:70, SEQ ID NO: 71, preferably said CAR comprises a polypeptide sequence selected from SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59; SEQ ID NO: 66, SEQ ID NO: 67, SEQ ID NO: 68, SEQ ID NO: 69, SEQ ID NO:70, SEQ ID NO: 71 and more preferably, said CAR preferentially comprises a polypeptide sequence selected from SEQ ID NO: 66, SEQ ID NO: 67, SEQ ID NO: 68, SEQ ID NO: 69, SEQ ID NO:70, SEQ ID NO: 71, and even more preferably, said CAR preferentially comprises a polypeptide of SEQ ID NO:68.

The present invention also provides:

A CD33 specific chimeric antigen receptor (CAR) comprising a polypeptide sequence having at least 80%, 81%, 82%, 83%, 84%, 85%, 86%, 87%, 88%, 89%, 90%, 91%, 92%, 93%, 94%, 95%, 96%, 97%, 98% or 99% identity with an amino acid sequence selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO:70, more preferably, a CAR comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%, or 99% identity with amino acid sequences consisting of SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, SEQ ID NO:70, even more preferably, a CARs comprising a polypeptide sequence displaying at least 80%, 81%, 82%, 83%, 84%, 85%, 86%, 87%, 88%, 89%, 90%, 91%, 92%, 93%, 94%, 95%, 96%, 97%, 98%, or 99% identity with amino acid sequences consisting of SEQ ID NO: 66, SEQ ID NO: 68, SEQ ID NO:70, Preferably, the present invention provides a CD33 specific CAR having a structure V1 as illustrated in FIG. 2, said structure comprising an extra cellular ligand binding-domain comprising VH and VL from a monoclonal anti-CD33 antibody, a FcRIIIα hinge, a CD8α transmembrane domain and a cytoplasmic domain including a CD3 zeta signaling domain and a co-stimulatory domain from 4-1BB.

Preferably, the present invention provides a CD33 specific CAR having one of the polypeptide structure V1 as illustrated in FIG. 2, said structure comprising an extra cellular ligand binding-domain comprising VH and VL from a monoclonal anti-CD33 antibody selected from M195, m2h12, and My9.6, optionally humanized, a FcRIIIα hinge, a CD8α transmembrane domain and a cytoplasmic domain including a CD3 zeta signaling domain and a co-stimulatory domain from 4-1BB.

More preferably, the present invention provides a CD33 specific chimeric antigen receptor (CAR) having one of the polypeptide structure V1 as illustrated in FIG. 2, comprising an amino acid sequence selected from the group consisting of SEQ ID NO: 48, SEQ ID NO: 54, SEQ ID NO: 60, and SEQ ID NO: 66, more preferably said CAR preferentially comprises a polypeptide sequence comprising and amino acid sequences consisting of SEQ ID NO: 48, SEQ ID NO: 54, and SEQ ID NO: 66.

Preferably, the present invention provides a CD33 specific chimeric antigen receptor (CAR) having a structure V3 as illustrated in FIG. 2, said structure comprising an extra cellular ligand binding-domain comprising VH and VL from a monoclonal anti-CD33 antibody, CD8α hinge, a CD8α transmembrane domain and a cytoplasmic domain including a CD3 zeta signaling domain and a co-stimulatory domain from 4-1BB.

Preferably, the present invention provides a CD33 specific CAR having a structure V3 as illustrated in FIG. 2, said structure comprising an extra cellular ligand binding-domain comprising VH and VL from a monoclonal anti-CD33 antibody selected from M195, m2h12, DRB2, and My9.6, optionally humanized, a FcRIIIα hinge, a CD8α transmembrane domain and a cytoplasmic domain including a CD3 zeta signaling domain and a co-stimulatory domain from 4-1BB.

More preferably, the present invention provides a CD33 specific CAR having a structure V3 as illustrated in FIG. 2, comprising an amino acid sequence selected from the group consisting of SEQ ID NO: 50, SEQ ID NO: 56, SEQ ID NO: 62, and SEQ ID NO: 68, more preferably said CAR preferentially comprises a polypeptide sequence comprising and amino acid sequences consisting of SEQ ID NO: 50, SEQ ID NO: 56, and SEQ ID NO: 68.

Preferably, the present invention provides a CD33 specific CAR having a structure V5 as illustrated in FIG. 2, said structure comprising an extra cellular ligand binding-domain comprising VH and VL from a monoclonal anti-CD33 antibody, a IgG1 hinge, a CD8α transmembrane domain and a cytoplasmic domain including a CD3 zeta signaling domain and a co-stimulatory domain from 4-1BB.

Preferably, the present invention provides a CD33 specific CAR having a structure V5 as illustrated in FIG. 2, said structure comprising an extra cellular ligand binding-domain comprising VH and VL from a monoclonal anti-CD33 antibody selected from M195, m2h12, DRB2, and My9.6, optionally humanized, a FcRIIIα hinge, a CD8α transmembrane domain and a cytoplasmic domain including a CD3 zeta signaling domain and a co-stimulatory domain from 4-1BB.

More preferably, the present invention provides a CD33 specific CAR having a structure V5 as illustrated in FIG. 2, comprising an amino acid sequence selected from the group consisting of SEQ ID NO: 52, SEQ ID NO: 58, SEQ ID NO: 64, and SEQ ID NO: 70, more preferably said CAR preferentially comprises a polypeptide sequence comprising and amino acid sequences consisting of SEQ ID NO: 52, SEQ ID NO: 58, and SEQ ID NO: 70.

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to CD33;
a Hinge derived from Fcgamma (☐) RIIIalpha (☐) having an amino acid sequence with at least 80%, more preferably at least 90%, 95% 97% or 99% sequence identity with the polypeptide of SEQ ID NO. 3;
a transmembrane domain derived from CD8alpha (☐) having an amino acid sequence with at least 90%, 91%, 92%, 93%, 94%, 95%, 96%, 97%, 98%, 99% or 100% identity with the polypeptide of SEQ ID NO. 6;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;
an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9;

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to CD33;
a Hinge derived from Fcgamma (☐) RIIIalpha (☐) having an amino acid sequence with at least 80%, more preferably at least 90%, 95% 97% or 99% sequence identity with the polypeptide of SEQ ID NO. 3;
a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;

an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9.

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to CD33;
a Hinge derived from human CD8 alpha chain having an amino acid sequence with at least 80%, more preferably at least 90%, 95% 97% or 99% sequence identity with the polypeptide of SEQ ID NO. 4;
a transmembrane domain derived from CD8alpha chain having an amino acid sequence with at least 90%, 91%, 92%, 93%, 94%, 95%, 96%, 97%, 98%, 99% or 100% identity with the polypeptide of SEQ ID NO. 6;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;
an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9;

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to CD33;
a Hinge derived from human CD8 alpha chain having an amino acid sequence with at least 80%, more preferably at least 90%, 95% 97% or 99% sequence identity with the polypeptide of SEQ ID NO. 4;
a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;
an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9.

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to CD33;
a Hinge derived from IgG1 having an amino acid sequence with at least 80%, more preferably at least 90%, 95% 97% or 99% sequence identity with the polypeptide of SEQ ID NO: 5;
a transmembrane domain derived from CD8alpha (図) having an amino acid sequence with at least 90%, 91%, 92%, 93%, 94%, 95%, 96%, 97%, 98%, 99% or 100% identity with the polypeptide of SEQ ID NO. 6;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;
an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9;

In one embodiment, the present invention provides a CD33 specific chimeric antigen receptor comprising:
a optional signal peptide having an amino acid sequence with at least 80%, more preferably at least 90%, 95% 97% or 99% sequence identity with the polypeptide of SEQ ID NO. 1 or 2; Preferably the optional signal peptide has an amino acid sequence with at least 80%, more preferably at least 90%, 95% 97% or 99% sequence identity with the polypeptide of SEQ ID NO 1. Preferably, the signal peptide is present.
a VH domain separated to a VL domain by a linker, said VH and VL contributing to the binding to
CD33;
a Hinge derived from IgG1 having an amino acid sequence with at least 80%, more preferably at least 90%, 95% 97% or 99% sequence identity with the polypeptide of SEQ ID NO: 5;
a transmembrane domain (TM) derived from 4-1BB having an amino acid sequence with at least 90%, 91%, 92%, 93%, 94%, 95%, 96%, 97%, 98%, 99% or 100% identity with the polypeptide of SEQ ID NO. 7;
a co-stimulatory signal molecule derived from 4-1BB having an amino acid sequence with at least 70%, preferably at least 80%, more preferably at least 90%, 95% 97%, 99% or 100% sequence identity with amino acid sequence selected from the group consisting of SEQ ID NO: 8;
an intracellular signaling domain comprising the CD3zeta signaling domain having an amino acid sequence with at least 70%, preferably at least 80%, more preferably at least 90%, 95% 97%, 99% or 100% sequence identity with amino acid sequence selected from the group consisting of SEQ ID NO: 9.

In one embodiment, the present invention provides at least one of the following CD33 specific CAR having the following sequences—or 80% of the following sequences:

M195-1
SEQ ID NO 48:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPAMDYWGQGTSVTVSS**GGGGSGGGGSGGG
GS**DIVLTQSPASLAVSLGQRATISCRASESVDNYGISFMNWFQQKPGQPP
KLLIYAASNQGSGVPARFSGSGSGTDFSLNIHPMEEDDTAMYFCQQSKEV
PWTFGGGTKLEIK<u>GLAVSTISSFFPPGYQIYIWAPLAGTCGVLLLSLVIT
LYCKRGRKKLLYIFKQP</u>FMRPVQTTQEEDGCSCRFPEEEEGGCELRVKFS
RSADAPAYQQGQNQLYNELNLGRREEYDVLDKRRGRDPEMGGKPRRKNPQ
EGLYNELQKDKMAEAYSEIGMKGERRRGKHDGLYQGLSTATKDTYDALH
MQALPPR

M195-2
SEQ ID NO 49:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPAMDYWGQGTSVTVSS**GGGGSGGGGSGGG
GS**DIVLTQSPASLAVSLGQRATISCRASESVDNYGISFMNWFQQKPGQPP
KLLIYAASNQGSGVPARFSGSGSGTDFSLNIHPMEEDDTAMYFCQQSKEV
PWTEGGGTKLEIK<u>GLAVSTISSFFPPGYQIISFFLALTSTALLFLLFFLT
LRFSVV</u>KRGRKKLLYIFKQPFMRPVQTTQEEDGCSCRFPEEEEGGCELRV
KFSRSADAPAYQQGQNQLYNELNLGRREEYDVLDKRRGRDPEMGGKPRRK
NPQEGLYNELQKDKMAEAYSEIGMKGERRRGKHDGLYQGLSTATKDTYD
ALHMQALPPR

M195-3
SEQ ID NO 50:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPANIDYWGQGTSVTVSS**GGGGSGGGGSGG
GGS**DIVLTQSPASLAVSLGQRATISCHASESVDNYGISFNINWFQQKPGQ
PPKLLIYAASNQGSGVPARFSGSGSGTDFSLNIHPMEEDDTAMYFCQQSK
EVPWTFGGGTKLEIK<u>TTTTPAPRPPTPAPTIASQPLSLRPEACRPAAGGAV
HTRGLDFACD</u>IYIWAPLAGTCGVLLLSLVITLYCKRGRKKLLYIFKQPFM
RPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEI
GMKGERRRGKHDGLYQGLSTATKDTYDALHMQALPPR

M195-4
SEQ ID NO 51:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPAMDYWGQGTSVTVSS**GGGGSGGGGSGGG
GS**DIVLTQSPASLAVSLGQRATISCHASESVDNYGISFNINWFQQKPGQP
PKLLIYAASNQGSGVPARFSGSGSGTDFSLNIHPMEEDDTAMYFCQQSKE
VPWTFGGGTKLEIK<u>TTTTPAPRPPTPAPTIASQPLSLRPEACRPAAGGAVH
TRGLDFACDIISFFLALTSTALLFLLFFLTLRFSVV</u>KRGRKKLLYIFKQP
FMRPVQTTQEEDGCSCRFPEEEEGGCELRVKFSRSADAPAYQQGQNQLYN
ELNLGRREEYDVLDKRRGRDPEMGGKPRRKNPQEGLYNELQKDKMAEAYS
EIGMKGERRRGKHDGLYQGLSTATKDTYDALHMQALPPR

M195-5
SEQ ID NO 52:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPANIDYWGQGTSVTVSS**GGGGSGGGGSGG
GGS**DIVLTQSPASLAVSLGQRATISCHASESVDNYGISFMNWFQQKPGQP
PKLLIYAASNQGSGVPARFSGSGSGTDFSLNIHPMEEDDTAMYFCQQSKE
VPWTFGGGTKLEIK<u>EPKSPDKTHTCPPCPAPPVAGPSVFLFPPKPKDTLM
IARTPEVICVVVDVSHEDPEVKFNWYVDGVEVHNAKTKPREEQYNSTYRV
VSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGKIYIWA
PLAGTCGVLLLSLVITLYCKRGRKKLLYIFKQPF</u>MRPVQTTQEEDGCSCR
FPEEEEGGCELRVKFSRSADAPAYQQGQNQLYNELNLGRREEYDVLDKRR
GRDPEMGGKPRRKNPQEGLYNELQKDKMAEAYSEIGMKGERRRGKHDGL
YQGLSTATKDTYDALHMQALPPR

M195-6
SEQ ID NO 53:
MALPVTALLLPLALLLHAARPEVQLQQSGPELVKPGASVKISCKASGYTF
TDYNMHWVKQSHGKSLEWIGYIYPYNGGTGYNQKFKSKATLTVDNSSSTA
YMDVRSLTSEDSAVYYCARGRPANIDYWGQGTSVTVSS**GGGGSGGGGSGG
GGS**DIVLTQSPASLAVSLGQRATISCRASESVDNYGISFNINWFQQKPGQ
PPKLLIYAASNQGSGVPARFSGSGSGTDFSLNIHPMEEDDTAMYFCQQSK
EVPWTFGGGTKLEIK<u>EPKSPDKTHTCPPCPAPPVAGPSVFLFPPKPKDTL
MIARTPEVICVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKIISF
FLALTSTALLFLLFFLTLRFSVV</u>KRGRKKLLYIFKQPFMRPVQTTQEEDG
CSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKG
HDGLYQGLSTATKDTYDALHMQALPPR m2H12-1
SEQ ID NO 54:
MALPVTALLLPLALLLHAARPQVQLQQSGPELVRPGTFVKISCKASGYTF
TNYDINWVNQRPGQGLEWIGWIYPGDGS TKYNEKFKAKATLTADKSSST
AYLQLNNLTSENSAVYFCASGYEDAMDYWGQGTSVTVSS**GGGGSGGGGSG
GGGS**DIKMTQSPSSMYASLGERVIINCKASQDINSYLSWFQQKPGKSPKT

LIYRANRLVDGVPSRFSGSGSGQDYSLTISSLEYEDMGIYYCLQYDEFPL

TFGAGTKLELKRGLAVSTISSFFPPGYQIYIWAPLAGTCGVLLLSLVITL

YCKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQE

GLYNELQKDKMAEAYSEIGMKGERRRGKGHDGLYQGLSTATKDTYDALHM

QALPPR m2H12-2
SEQ ID NO 55:
MALPVTALLLPLALLLHAARPQVQLQQSGPELVRPGTFVKISCKASGYTF

TNYDINWVNQRPGQGLEWIGWIYPGDGSTKYNEKFKAKATLTADKSSSTA

YLQLNNLTSENSAVYFCASGYEDAMDYWGQGTSVTVSSGGGGSGGGGSGG

GGSDIKMTQSPSSMYASLGERVIINCKASQDINSYLSWFQQKPGKSPKTL

IYRANRLVDGVPSRFSGSGSGQDYSLTISSLEYEDMGIYYCLQYDEFPLT

FGAGTKLELKRGLAVSTISSFFPPGYQIISFFLALTSTALLFLLFFLTLR

FSVVKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPR m2H12-3
SEQ ID NO 56:
MALPVTALLLPLALLLHAARPQVQLQQSGPELVRPGTFVKISCKASGYTF

TNYDINWVNQRPGQGLEWIGWIYPGDGSTKYNEKFKAKATLTADKSSSTA

YLQLNNLTSENSAVYFCASGYEDAMDYWGQGTSVTVSSGGGGSGGGGSGG

GGSDIKMTQSPSSMYASLGERVIINCKASQDINSYLSWFQQKPGKSPKTL

IYRANRLVDGVPSRFSGSGSGQDYSLTISSLEYEDMGIYYCLQYDEFPLT

FGAGTKLELKRTTTPAPRPPTPAPTIASQPLSLRPEACRPAAGGAVHTRG

LDFACDIYIWAPLAGTCGVLLLSLVITLYCKRGRKKLLYIFKQPFMRPVQ

TTQEEDGCSCRFPEEEEGGCELRVKFSRSADAPAYQQGQNQLYNELNLGR

REEYDVLDKRRGRDPEMGGKPRRKNPQEGLYNELQKDKMAEAYSEIGMKG

ERRRGKGHDGLYQGLSTATKDTYDALHMQALPPR m2H12-4
SEQ ID NO 57:
MALPVTALLLPLALLLHAARPQVQLQQSGPELVRPGTFVKISCKASGYTF

TNYDINWVNQRPGQGLEWIGWIYPGDGSTKYNEKFKAKATLTADKSSSTA

YLQLNNLTSENSAVYFCASGYEDAMDYWGQGTSVTVSSGGGGSGGGGSGG

GGSDIKMTQSPSSMYASLGERVIINCKASQDINSYLSWFQQKPGKSPKTL

IYRANRLVDGVPSRFSGSGSGQDYSLTISSLEYEDMGIYYCLQYDEFPLT

FGAGTKLELKRTTTPAPRPPTPAPTIASQPLSLRPEACRPAAGGAVHTRG

LDFACDIISFFLALTSTALLFLLFFLTLRFSVVKRGRKKLLYIFKQPFMR

PVQTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR m2H12-5
SEQ ID NO 58:
MALPVTALLLPLALLLHAARPQVQLQQSGPELVRPGTFVKISCKASGYTF

TNYDINWVNQRPGQGLEWIGWIYPGDGSTKYNEKFKAKATLTADKSSSTA

YLQLNNLTSENSAVYFCASGYEDAMDYWGQGTSVTVSSGGGGSGGGGSGG

GGSDIKMTQSPSSMYASLGERVIINCKASQDINSYLSWFQQKPGKSPKTL

IYRANRLVDGVPSRFSGSGSGQDYSLTISSLEYEDMGIYYCLQYDEFPLT

FGAGTKLELKREPKSPDKTHTCPPCPAPPVAGPSVFLFPPKPKDTLMIAR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGKIYIWAPLA

GTCGVLLLSLVITLYCKRGRKKLLYIFKQPFMRPVQTTQEEDGCSCRFPE

EEEGGCELRVKFSRSADAPAYQQGQNQLYNELNLGRREEYDVLDKRRGRD

PEMGGKPRRKNPQEGLYNELQKDKMAEAYSEIGMKGERRRGKGHDGLYQG

LSTATKDTYDALHMQALPPR m2H12-6
SEQ ID NO 59:
MALPVTALLLPLALLLHAARPQVQLQQSGPELVRPGTFVKISCKASGYTF

TNYDINWVNQRPGQGLEWIGWIYPGDGSTKYNEKFKAKATLTADKSSSTA

YLQLNNLTSENSAVYFCASGYEDAMDYWGQGTSVTVSSGGGGSGGGGSGG

GGSDIKMTQSPSSMYASLGERVIINCKASQDINSYLSWFQQKPGKSPKTL

IYRANRLVDGVPSRFSGSGSGQDYSLTISSLEYEDMGIYYCLQYDEFPLT

FGAGTKLELKREPKSPDKTHTCPPCPAPPVAGPSVFLFPPKPKDTLMIAR

TPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFF

LYSKLTVDKSRWQQGNVFSCSVMHEALHNHYTQKSLSLSPGKIISFFLAL

TSTALLFLLFFLTLRFSVVKRGRKKLLYIFKQPFMRPVQTTQEEDGCSCR

FPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGL

YQGLSTATKDTYDALHMQALPPR

DRB2-1
SEQ ID NO 60:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVSGLAVSTISSFFPPGYQIYIWAPLAGTCGV

LLLSLVITLYCKRGRKKLLYIFKQPFMRPVQTTQEEDGCSCRFPEEEEGG

CELRVKFSRSADAPAYQQGQNQLYNELNLGRREEYDVLDKRRGRDPEMGG

KPRRKNPQEGLYNELQKDKMAEAYSEIGMKGERRRGKGHDGLYQGLSTAT

KDTYDALHMQALPPR

DRB2-2
SEQ ID NO 61:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVS<u>GLAVSTISSFFPPGYQIISFFLALTSTAL</u>

<u>LFLLFFLTLRFSVV</u>KRGRKKLLYIFKQPFMRPVQTTQEEDGCSCRFPEEE

EGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLS

TATKDTYDALHMQALPPR

DRB2-3
SEQ ID NO 62:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVS<u>TTTPAPRPPTPAPTIASQPLSLRPEACRP</u>

<u>AAGGAVHTRGLDFACD</u>IYIWAPLAGTCGVLLLSLVITLYCKRGRKKLLYI

FKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR

DRB2-4
SEQ ID NO 63:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVS<u>TTTPAPRPPTPAPTIASQPLSLRPEACRP</u>

<u>AAGGAVHTRGLDFACD</u>IISFFLALTSTALLFLLFFLTLRFSVVKRGRKKL

LYIFKQPFMRPVQTTQEEDGCSCRFPEEEEGGCELRVKFSRSADAPAYQQ

GQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

DRB2-5
SEQ ID NO 64:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVS<u>EPKSPDKTHTCPPCPAPPVAGPSVFLFPP</u>

<u>KPKDTLMIARTPEVICVVVDVSHEDPEVKFNWYVDGVEVHNAKTKPREEQ</u>

<u>YNSTYRVVSVLTVLHQDWLNGKEYKCKVSNKALPAPIEKTISKAKGQPRE</u>

<u>PQVYTLPPSRDELTKNQVSLTCLVKGFYPSDIAVEWESNGQPENNYKTTP</u>

<u>PVLDSDGSFFLYSKLTVDKSRWQQGNVFSCSVMHEALHNHYTQKSLSLSP</u>

<u>GK</u>IYIWAPLAGTCGVLLLSLVITLYCKRGRKKLLYIFKQPFMRPVQTTQE

EDGCSCRFPEEEEGGCELRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR

DRB2-6
SEQ ID NO 65:
MALPVTALLLPLALLLHAARPEVKLQESGPELVKPGASVKMSCKASGYKF

TDYVVHWLKQKPGQGLEWIGYINPYNDGTKYNEKFKGKATLTSDKSSSTA

YMEVSSLTSEDSAVYYCARDYRYEVYGMDYWGQGTSVTVSSGGGGSGGGG

SGGGGSDIVLTQSPTIMSASPGERVTMTCTASSSVNYIHWYQQKSGDSPL

RWIFDTSKVASGVPARFSGSGSGTSYSLTISTMEAEDAATYYCQQWRSYP

LTFGDGTRLELKRADAAPTVS<u>EPKSPDKTHTCPPCPAPPVAGPSVFLFPP</u>

<u>KPKDTLMIARTPEVICVVVDVSHEDPEVKFNWYVDGVEVHNAKTKPREEQ</u>

<u>YNSTYRVVSVLTVLHQDWLNGKEYKCKVSNKALPAPIEKTISKAKGQPRE</u>

<u>PQVYTLPPSRDELTKNQVSLTCLVKGFYPSDIAVEWESNGQPENNYKTTP</u>

<u>PVLDSDGSFFLYSKLTVDKSRWQQGNVFSCSVMHEALHNHYTQKSLSLSP</u>

<u>GK</u>IISFFLALTSTALLFLLFFLTLRFSVVKRGRKKLLYIFKQPFMRPVQT

TQEEDGCSCRFPEEEEGGCELRVKFSRSADAPAYQQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR

My9.6-1
SEQ ID NO 66:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

GQSPKLLIYWASTRESGVPDRFTGSGSGTDFTLTISSVQSEDLAIYYCHQ

YLSSRTFGGGTKLEIKR<u>GLAVSTISSFFPPGYQI</u>YIWAPLAGTCGVLLLS

LVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR

My9.6-2
SEQ ID NO 67:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

-continued

GQSPKLLIYWASTRESGVPDRFTGSGSGTDFTLTISSVQSEDLAIYYCHQ

YLSSRTFGGGTKLEIKR<u>GLAVSTISSFFPPGYQIISFFLALTSTALLFLL</u>

<u>FFLTLRFSVVKRGRKKLLYIFKQPFMRPVQTTQEEDGCSCRFPEEEEGGC</u>

<u>ELRVKFSRSADAPAYQQGQNQLYNELNLGRREEYDVLDKRRGRDPEMGGK</u>

<u>PRRKNPQEGLYNELQKDKMAEAYSEIGMKGERRRGKGHDGLYQGLSTATK</u>

<u>DTYDALHMQALPPR</u>

My9.6-3
SEQ ID NO 68:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

GQSPKLLIYWASTRESGVPDRFTGSGSGTDFTLTISSVQSEDLAIYYCHQ

YLSSRTEGGGTKLEIKR<u>TTTPAPRPPTPAPTIASQPLSLRPEACRPAAGG</u>

<u>AVHTRGLDFACDIYIWAPLAGTCGVLLLSLVITLYCKRGRKKLLYIFKQP</u>

<u>FMRPVQTTQEEDGCSCRFPEEEEGGCELRVKFSRSADAPAYQQGQNQLYN</u>

<u>ELNLGRREEYDVLDKRRGRDPEMGGKPRRKNPQEGLYNELQKDKMAEAYS</u>

<u>EIGMKGERRRGKGHDGLYQGLSTATKDTYDALHMQALPPR</u>

My9.6-4
SEQ ID NO 69:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

GQSPKLLIYWASTRESGVPDRFTGSGSGTDFTLTISSVQSEDLAIYYCHQ

YLSSRTFGGGTKLEIKR<u>TTTPAPRPPTPAPTIASQPLSLRPEACRPAAGG</u>

<u>AVHTRGLDFACDIISFFLALTSTALLFLLFFLTLRFSVVKRGRKKLLYIF</u>

<u>KQPFMRPVQTTQEEDGCSCRFPEEEEGGCELRVKFSRSADAPAYQQGQNQ</u>

<u>LYNELNLGRREEYDVLDKRRGRDPEMGGKPRRKNPQEGLYNELQKDKMAE</u>

<u>AYSEIGMKGERRRGKGHDGLYQGLSTATKDTYDALHMQALPPR</u>

My9.6-5
SEQ ID NO 70:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

GQSPKLLIYWASTRESGVPDRFTGSGSGTDFTLTISSVQSEDLAIYYCHQ

YLSSRTFGGGTKLEIKR<u>EPKSPDKTHTCPPCPAPPVAGPSVFLFPPKPKD</u>

<u>TLMIARTPEVTCVVVDVSHEDPEVKFNWYVDGVEVHNAKTKPREEQYNST</u>

<u>YRVVSVLTVLHQDWLNGKEYKCKVSNKALPAPIEKTISKAKGQPREPQVY</u>

<u>TLPPSRDELTKNQVSLTCLVKGFYPSDIAVEWESNGQPENNYKTTPPVLD</u>

<u>SDGSFFLYSKLTVDKSRWQQGNVFSCSVMHEALHNHYTQKSLSLSPGKIY</u>

<u>IWAPLAGTCGVLLLSLVITLYCKRGRKKLLYIFKQPFMRPVQTTQEEDGC</u>

<u>SCRFPEEEEGGCELRVKFSRSADAPAYQQGQNQLYNELNLGRREEYDVLD</u>

<u>KRRGRDPEMGGKPRRKNPQEGLYNELQKDKMAEAYSEIGMKGERRRGKGH</u>

<u>DGLYQGLSTATKDTYDALHMQALPPR</u>

My9.6-6
SEQ ID NO 71:
MALPVTALLLPLALLLHAARPQVQLQQPGAEVVKPGASVKMSCKASGYTF

TSYYIHWIKQTPGQGLEWVGVIYPGNDDISYNQKFKGKATLTADKSSTTA

YMQLSSLTSEDSAVYYCAREVRLRYFDVWGAGTTVTVSSGGGGSGGGGSG

GGGSNIMLTQSPSSLAVSAGEKVTMSCKSSQSVFFSSSQKNYLAWYQQIP

GQSPKLLIYWASTRESGVPDRFTGSGSGTDFTLTISSVQSEDLAIYYCHQ

YLSSRTFGGGTKLEIKR<u>EPKSPDKTHTCPPCPAPPVAGPSVFLFPPKPKD</u>

<u>TLMIARTPEVTCVVVDVSHEDPEVKFNWYVDGVEVHNAKTKPREEQYNST</u>

<u>YRVVSVLTVLHQDWLNGKEYKCKVSNKALPAPIEKTISKAKGQPREPQVY</u>

<u>TLPPSRDELTKNQVSLTCLVKGFYPSDIAVEWESNGQPENNYKTIPPVLD</u>

<u>SDGSFFLYSKLTVDKSRWQQGNVFSCSVMHEALHNHYTQKSLSLSPGKII</u>

<u>SFFLALTSTALLFLLFFLTLRFSVVKRGRKKLLYIFKQPFMRPVQTTQEE</u>

<u>DGCSCRFPEEEEGGCELRVKFSRSADAPAYQQGQNQLYNELNLGRREEYD</u>

<u>VLDKRRGRDPEMGGKPRRKNPQEGLYNELQKDKMAEAYSEIGMKGERRRG</u>

<u>KGHDGLYQGLSTATKDTYDALHMQALPPR.</u>

In one embodiment, the present invention provides primary T cells endowed with at least one of these CD33 specific CAR.

In a preferred embodiment, the present invention provides a CD33 specific chimeric antigen receptor (CAR) with at least 80% of a sequence selected from: SEQ ID N° 48 to 71, more preferably at least 80% of SEQ ID NO. 68.

and even more preferably, said CARs preferentially comprise a polypeptide sequence displaying at least 80%, 81%, 82%, 83%, 84%, 85%, 86%, 87%, 88%, 89%, 90%, 91%, 92%, 93%, 94%, 95%, 96%, 97%, 98%, or 99% identity with amino acid sequences consisting of SEQ ID NO:68.

In this embodiment, said CAR preferentially comprises a polypeptide sequence displaying 81% identity with amino acid sequences consisting of SEQ ID NO:68, said CAR preferentially comprises a polypeptide sequence displaying 82% identity with amino acid sequences consisting of SEQ ID NO:68, said CAR preferentially comprises a polypeptide sequence displaying 83% identity with amino acid sequences consisting of SEQ ID NO:68, said CAR preferentially comprises a polypeptide sequence displaying 84% identity with amino acid sequences consisting of SEQ ID NO:68, said CAR preferentially comprises a polypeptide sequence displaying 85% identity with amino acid sequences consisting of SEQ ID NO:68, said CAR preferentially comprises a polypeptide sequence displaying 86% identity with amino acid sequences consisting of SEQ ID NO:68, said CAR preferentially comprises a polypeptide sequence displaying 87% identity with amino acid sequences consisting of SEQ ID NO:68, said CARs preferentially comprises a polypeptide sequence displaying 88% identity with amino acid sequences consisting of SEQ ID NO:68, said CAR preferentially comprises a polypeptide sequence displaying 89% identity with amino acid sequences consisting of SEQ ID NO:68,
said CAR preferentially comprises a polypeptide sequence displaying 90% identity with amino acid sequences consisting of SEQ ID NO:68,
said CAR preferentially comprises a polypeptide sequence displaying 91% identity with amino acid sequences consisting of SEQ ID NO:68,
said CAR preferentially comprises a polypeptide sequence displaying 92% identity with amino acid sequences consisting of SEQ ID NO:68,
said CAR preferentially comprises a polypeptide sequence displaying 93% identity with amino acid sequences consisting of SEQ ID NO:68,
said CAR preferentially comprises a polypeptide sequence displaying 94% identity with amino acid sequences consisting of SEQ ID NO:68,
said CAR preferentially comprises a polypeptide sequence displaying 95% identity with amino acid sequences consisting of SEQ ID NO:68,
said CAR preferentially comprises a polypeptide sequence displaying 96% identity with amino acid sequences consisting of SEQ ID NO:68,
said CAR preferentially comprises a polypeptide sequence displaying 97% identity with amino acid sequences consisting of SEQ ID NO:68
said CAR preferentially comprises a polypeptide sequence displaying 98% identity with amino acid sequences consisting of SEQ ID NO:68,
said CAR preferentially comprises a polypeptide sequence displaying 99% identity with amino acid sequences consisting of SEQ ID NO:68,
In one embodiment, said CAR is having 100% identity with amino acid sequences consisting of SEQ ID NO:68.

The present invention encompasses a CAR having a percentage of identity as described herein (from 80% to 99%) with any one of the sequences from SEQ ID 48 to SEQ ID 71.

The present invention provides a CD33 specific CAR comprising
(a) an extra cellular ligand binding-domain comprising VH and VL from a monoclonal anti-CD33 antibody, optionally humanized
(b) a CD8☐ hinge,
(c) a CD8α transmembrane domain and
(d) a cytoplasmic domain including a CD3 zeta signaling domain and a co-stimulatory domain from 4-1BB.

The present invention provides a CD33 specific CAR comprising
(a) an extra cellular ligand binding-domain comprising VH and VL from a monoclonal anti-CD33 antibody, optionally humanized
(b) a FcγRIIIα hinge,
(c) a CD8α transmembrane domain and
(d) a cytoplasmic domain including a CD3 zeta signaling domain and a co-stimulatory domain from 4-1BB
Polynucleotides, Vectors:

The present invention also relates to polynucleotides, vectors encoding any one of the above described CARs according to the invention.

The present invention also relates to a polynucleotide encoding an anti-CD33 CAR according to the invention, to a vector, preferably to a lentiviral vector, comprising at least one of said polynucleotide encoding an anti-CD33 CAR according to the invention.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 1 and 2.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering Immune Cells Endowed with CARs:

The present invention encompasses the method of preparing immune cells for immunotherapy comprising introducing ex-vivo into said immune cells the polynucleotides or vectors encoding one of the CD33 CAR as previously described.

In a preferred embodiment, said polynucleotides are included in lentiviral vectors in view of being stably expressed in the immune cells.

According to further embodiments, said method further comprises the step of genetically modifying said cell to make them more suitable for allogeneic transplantation.

According to a first aspect, the immune cell can be made less allogeneic, for instance, by inactivating at least one gene expressing one or more component of T-cell receptor (TCR) as described in WO 2013/176915, which can be combined with the inactivation of a gene encoding or regulating HLA or β2m protein expression. Accordingly, the risk of graft versus host syndrome and graft rejection is significantly reduced.

According to another aspect, at least one gene allowing the expression of one or more component of CD33 is inactivated in the CD33 specific CAR immune cells of the invention. Inhibiting CD33 surface expression in cells expressing an anti-CD33 CAR is part of a method for preparing the anti-CD33 CAR expressing immune cells of the invention.

A general method is described in WO 2013/176915. Inactivation of CD33 gene can be combined with the activation/or inactivation of a gene encoding or regulating CD33 expression such as sialic acid binding Ig-like lectins (Cao H, Crocker P R. Evolution of CD33-related siglecs: regulating host immune functions and escaping pathogen exploitation? *Immunology.* 2011 January; 132(1):18-26) so that cell surface expression of CD33 the anti-CD33 CAR expressing immune cells is inhibited and consequently do not alter the survival or inhibit the activity the anti-CD33 CAR expressing neighboring cells.

According to another aspect, the immune cells can be further genetically engineered to improve their resistance to immunosuppressive drugs or chemotherapy treatments, which are used as standard care for treating CD33 positive malignant cells. For instance, CD52 and glucocorticoid receptors (GR), which are drug targets of Campath (alemtuzumab) and glucocorticoids treatments, can be inactivated to make the cells resistant to these treatments and give them a competitive advantage over patient's own T-cells not endowed with specific CD33 CARs. Expression of CD3 gene can also be suppressed or reduced to confer resistance to Teplizumab, which is another immune suppressive drug. Expression of HPRT can also be suppressed or reduced according to the invention to confer resistance to 6-thioguanine, a cytostatic agent commonly used in chemotherapy especially for the treatment of acute lymphoblasic leukemia. Expression of the "GLI1" gene may be reduced.

According to further aspect of the invention, the immune cells can be further manipulated to make them more active or limit exhaustion, by inactivating genes encoding proteins that act as "immune checkpoints" that act as regulators of T-cells activation, such as PDCD1 or CTLA-4. Examples of genes, which expression could be reduced or suppressed are indicated in Table 9.

TABLE 9

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |

TABLE 9-continued

List of genes encoding immune checkpoint proteins.

| Pathway | | Genes that can be inactivated In the pathway |
|---|---|---|
| | LAIR1(cd305) | LAIR1 |
| | SIGLECs | SIGLEC7 |
| | | SIGLEC3 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

In a preferred embodiment said method of further engineering the immune cells involves introducing into said T cells polynucleotides, in particular mRNAs, encoding specific rare-cutting endonuclease to selectively inactivate the genes, as those mentioned above, by DNA cleavage. In a more preferred embodiment said rare-cutting endonucleases are TALE-nucleases or Cas9 endonuclease. TAL-nucleases have so far proven higher specificity and cleavage efficiency over the other types of rare-cutting endonucleases, making them the endonucleases of choice for producing of the engineered immune cells on a large scale with a constant turn-over.

Delivery Methods

The different methods described above involve introducing CAR into a cell. As non-limiting example, said CAR can be introduced as transgenes encoded by one plasmid vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non-limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

As a preferred embodiment, the present invention provides T-cells or a population of T-cells endowed with a CD33 CAR as described above, that do not express functional TCR and that a reactive towards CD33 positive cells, for their allogeneic transplantation into patients.

As a more preferred embodiment, the present invention provides the engineered immune cells according to the invention comprising T-cells or a population of T-cells endowed with a CD33 CAR as described above, that do neither express a functional TCR nor CD33, and are reactive towards CD33 positive cells, for their allogeneic transplantation into patients.

As an even more preferred embodiment, the present invention provides the engineered immune cells according to the invention comprising T-cells or a population of T-cells endowed with a CD33 CAR, said CD33 CAR comprising a polypeptide structure selected from V1, V3 and V5, said polypeptide structure comprising an extra cellular ligand binding-domain comprising VH and VL from a monoclonal anti-CD33 antibody, a hinge selected from a FcRIIIα hinge, CD8α hinge, and IgG1 hinge, a CD8α transmembrane domain and a cytoplasmic domain including a CD3 zeta signaling domain and a co-stimulatory domain from 4-1BB.

In one embodiment, the engineered immune cells according to the invention comprise a specific CD33 CAR comprising a monoclonal anti-CD33 antibody is selected from M195, m2h12, DRB2, and My9.6, or from M195, m2h12, and My9.6, and optionally humanized.

In a more preferred embodiment, said CD33 CAR comprises a polypeptide selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO:70, or comprise a polypeptide selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, SEQ ID NO:70.

In an even more preferred embodiment, T-cells endowed with a CD33 CAR, do not express functional TCR and CD33, and said CD33 CAR comprises a polypeptide of SEQ ID NO: 68, and optionally humanized.

In one even more preferred embodiment, T-cells or a population of T-cells endowed with a CD33 CAR, in particular anti-CD33 CAR expressing T cells that do neither express functional TCR nor CD33, comprise a polypeptide sequence having at least 80%, 81%, 82%, 83%, 84%, 85%, 86%, 87%, 88%, 89%, 90%, 91%, 92%, 93%, 94%, 95%, 96%, 97%, 98% or 99% identity with any one of an amino acid sequence selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, SEQ ID NO:70, or having at least 80%, 81%, 82%, 83%, 84%, 85%, 86%, 87%, 88%, 89%, 90%, 91%, 92%, 93%, 94%, 95%, 96%, 97%, 98% or 99% identity with any one of an amino acid sequence selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, SEQ ID NO:70 or having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 68.

In this even more preferred embodiment, T-cells endowed with a CD33 CAR, do not express functional TCR and CD33 and comprise a polypeptide sequence having at least 80%, 81%, 82%, 83%, 84%, 85%, 86%, 87%, 88%, 89%, 90%, 91%, 92%, 93%, 94%, 95%, 96%, 97%, 98% or 99% identity with an amino acid sequence selected from the group consisting of SEQ ID NO: 50, SEQ ID NO: 52, SEQ ID NO: 56, SEQ ID NO: 58, SEQ ID NO: 68, SEQ ID NO:70, or a polypeptide sequence having at least 80%, 81%, 82%, 83%, 84%, 85%, 86%, 87%, 88%, 89%, 90%, 91%, 92%, 93%, 94%, 95%, 96%, 97%, 98% or 99% identity with an amino acid sequence selected from the group consisting of SEQ ID NO: 50, SEQ ID NO: 56, SEQ ID NO: 68 or a polypeptide sequence having at least 80%, 81%, 82%, 83%, 84%, 85%, 86%, 87%, 88%, 89%, 90%, 91%, 92%, 93%, 94%, 95%, 96%, 97%, 98% or 99% identity with SEQ ID NO: 68.

Preferably, said anti-CD33 CAR expressing T cell is a TCRalpha KO and CD33 KO T cell and is resistant to at least one drug used for the treatment of AML.

An anti-CD33 CAR expressing T cell according to the invention represents isolated immune T cells endowed with anti-CD33 CAR, preferably TCRalpha KO and/or CD33 KO immune T cells endowed with anti-CD33 CAR cells and more preferably TCRalpha KO and/or CD33 KO immune T cells endowed with anti-CD33 CAR cells that are resistant to at least one drug used for the treatment of AML. Preferably, an anti-CD33 CAR expressing T cell expressed in T cells according to the invention comprises an anti-CD33 CAR having one of the sequences selected from SEQ ID NO 48 to SEQ ID NO 71, more preferably an anti-CD33 CAR having at least 80% identity with the SEQ ID NO 48 to SEQ ID NO 71 and even more preferably at least 80% identity with SEQ ID NO 68. An Engineered immune cell (or anti-CD33 CAR-expressing T cells) according to the invention means any one of the engineered immune cell according to the invention, described above.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, −10, −2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

In a preferred aspect, the present invention relies on methods for treating patients in need thereof, said method comprising at least one of the following steps:

(a) Providing an immune-cell obtainable by any one of the methods of the invention to prepare an anti-CD33 expressing CAR immune cell, (or any of the engineered immune cell of the invention)

(b) Administrating said anti-CD33 expressing CAR immune cells to said patient; optionally, said CD33 CAR T cell of the invention can undergo robust in vivo T cell expansion and can persist for an extended amount of time, in particular can bind to CD33 for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In one embodiment, an anti-CD33 CAR expressing T cell according to the invention is provided for its use as a medicament.

In a particular embodiment, said anti-CD33 CAR expressing T cell according to the invention provided for its use as a medicament, comprises a polypeptide selected from SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38 and more preferably a polypeptide having at least 80% identity with a polypeptide selected from a polypeptide of SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, Even more preferably, said anti-CD33 CAR expressing T cell according to the invention provided for its use as a medicament, comprises a polypeptide selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO:70, or comprise a polypeptide selected from the group consisting of SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, SEQ ID NO:70; any of these CAR may be humanized.

In one embodiment, an anti-CD33 CAR expressing T cell according to the invention provided for its use as a medicament, comprises a polypeptide of SEQ ID NO: 68 or a polypeptide having at least 80% identity with a polypeptide of SEQ ID NO: 68, optionally humanized.

In other words, the invention is related to an anti-CD33 CAR expressing T cell according to the invention comprising a polypeptide having at least 80% identity with any one of the polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68 and SEQ ID NO:70, optionally humanized for its use as a medicament.

Engineered immune cells that can be used as a medicament or with the disclosed methods are described in the previous sections. Preferably Engineered immune cells may comprise primary T cells, wherein a CD33 expression in altered, a TCR expression is altered, optionally resistant to at least one drug used to treat an hematological cancer.

In general, said medicament can be used for treating a CD33-expressing cell-mediated pathological condition or a condition characterized by the direct or indirect activity of a CD33-expressing cell, ie a condition linked to the detrimental activity of CD33-expressing cells.

Said medicament can be used to treat patients diagnosed wherein a pre-malignant or malignant cancer condition characterized by CD33-expressing T cells, especially by an overabundance of CD33-expressing T cells. Such conditions are found in hematologic cancers, such as leukemia or malignant lymphoproliferative disorders such as B-cell lymphoproliferative disorders.

Another example of CD33-expressing cell-mediated pathological condition or a condition characterized by the direct or indirect activity of a CD33-expressing cell that can be treated with an anti-CD33 CAR expressing T cell according to the invention is Alzheimer disease.

A Lymphoproliferative disorder can be lymphoma, in particular multiple myeloma, non-Hodgkin's lymphoma, Burkitt's lymphoma, and follicular lymphoma (small cell and large cell).

Any one of the CD33-mediating or CD33-involving disease in particular malignant lymphoproliferative disorder or leukemia may be treated and the health condition of the patient suffering said pathological condition may be improved, with the anti-CD33 CAR-expressing T cells of the present invention.

In a preferred embodiment, the cancer that may be treated using the anti-CD33 CAR-expressing T cells of the present invention is leukemia, a disease associated to leukemia or a complication thereof, in particular AML, an AML subtype, AML-related complication, and AML-related conditions.

A leukemia that can also be prevented or treated using the anti-CD33 CAR-expressing T cells of the present invention can be acute myelogenous leukemia (AML), chronic myelogenous leukemia, melodysplastic syndrome, acute lymphoid leukemia, acute lymphoblastic leukemia, chronic lymphoid leukemia, and myelodysplastic syndrome.

AML or AML subtypes that may be treated using the anti-CD33 CAR-expressing T cells of the present invention may be in particular, acute myeloblastic leukemia, minimally differentiated acute myeloblastic leukemia, acute myeloblastic leukemia without maturation, acute myeloblastic leukemia with granulocytic maturation, promyelocytic or acute promyelocytic leukemia (APL), acute myelomonocytic leukemia, myelomonocytic together with bone marrow eosinophilia, acute monoblastic leukemia (M5a) or acute monocytic leukemia (M5b), acute erythroid leukemia, including erythroleukemia (M6a) and very rare pure erythroid leukemia (M6b), acute megakaryoblastic leukemia (M7), acute basophilic leukemia, acute panmyelosis with myelofibrosis, whether involving CD33-positive cells.

Subtypes of AML that may be treated using the anti-CD33 CAR-expressing T cells of the present invention also include, AML with t (8; 21) (q22; q22), (AML1/ETO), AML with inv (16) (p13; q22) or t (16; 16) (p13; q22), (CBFβ/MYH11), AML with t (15; 17) (q22; q12), (PML/RARα) and variants, AML with t(9; 11)(p22; q23), (MLLT3/MLL), AML with t(6; 9)(p23; q34) (DEK/NUP214), AML with inv(3)(q21q26) or t(3; 3)(q21;q26), (RPN1/EVI1), AML with t(1; 22)(p13; q13) (RBM15/MKL1) (megakaryocytic), AML with myelodysplasia-related changes including AML arising from prior MDS or MDS/MPN, AML with an MDS-related cytogenetic abnormality, and AML with multilineage dysplasia, alkylating agent/radiation related AML, AML, minimally differentiated (also known as AML-M0), AML without maturation (also known as AML-M1), AML with maturation (also known as AML-M2), Acute myelomonocytic leukemia (also known as AML-M4), Acute monoblastic/monocytic leukemia (also known as AML-M5), Acute erythroid leukemia (also known as AML-M6) and pure erythroid leukemia.

Accordingly, AML classified as AML with specific genetic abnormalities are conditions that may be treated using the anti-CD33 CAR-expressing T cells of the present invention. Classification is based on the ability of karyotype to predict response to induction therapy, relapse risk, survival.

Accordingly, AML that may be treated using the anti-CD33 CAR-expressing T cells of the present invention may be AML with a translocation between chromosomes 8 and 21, AML with a translocation or inversion in chromosome 16, AML with a translocation between chromosomes 9 and 11, APL (M3) with a translocation between chromosomes 15 and 17, AML with a translocation between chromosomes 6 and 9, AML with a translocation or inversion in chromosome 3, AML (megakaryoblastic) with a translocation between chromosomes 1 and 22.

The present invention is particularly useful for the treatment of AML associated with these particular cytogenetic markers.

The present invention also provides an anti-CD33 CAR expressing T cell for the treatment of patients with specific cytogenetic subsets of AML, such as patients with t(15; 17)(q22; q21) identified using all-trans retinoic acid (ATRA) and for the treatment of patients with t(8; 21)(q22; q22) or inv(16)(p13q22)/t(16;16)(p13; q22) identified using repetitive doses of high-dose cytarabine.

Preferably, the present invention provides an anti-CD33 CAR expressing T cell for the treatment of patients with aberrations, such as −5/del(5q), −7, abnormalities of 3q, or a complex karyotype, who have been shown to have inferior complete remission rates and survival.

Group of Patients

In a preferred embodiment, the invention provides a medication for leukemia in particular for AML in patients over 60 years, in patients of less than 20 years, in particular in children.

In a more preferred embodiment, the present invention provides a pediatric treatment, in particular a pediatric treatment against AML, or AML-related diseases or complications.

In still another preferred embodiment, the present invention is used as a treatment in AML patients with low, poor or unfavorable status that is to say with a predicted survival of less than 5 years survival rate. In this group, patients suffering AML with the following cytogenetic characteristics: −5; 5q; −7; 7q-; 11q23; non t(9; 11); inv(3); t(3; 3); t(6; 9); t(9; 22) is associated with poor-risk status (Byrd J. C. et al., Dec. 15, 2002; Blood: 100 (13) and is especially contemplated to be treated according to the present invention or with an object of the present invention.

In one embodiment, the anti-CD33 CAR expressing T cell of the present invention may be used as a treatment in case of AML relapse, or in case of refractory or resistant AML. Preferably, T cells comprising at least one humanized anti-CD33 CAR of the invention comprising or consisting of SEQ ID NO. 1 and of a polypeptide selected from a polypeptide having at least 80% to 100% identity with SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, or a combination thereof, are used in patients with AML relapse, or with refractory or resistant AML, more preferably, in combination with at least one other anti-cancer drug.

In another preferred embodiment, said least one anti-CD33 CAR T cell of the invention, is used for preventing cancer cells development occurring in particular after anti-cancer treatment, during bone marrow depletion or before bone marrow transplantation, after bone marrow destruction.

AML Complications

In one particular embodiment the invention provides a medicament that improves the health condition of a patient, in particular a patient undergoing a complication related to AML. More preferably, said engineered anti-CD33 CAR expressing T cell of the invention is expressing at least one anti-CD33 CAR comprising a SEQ ID NO 1 and a polypeptide having at least 80% identity with SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, or a combination thereof, and is used as a medicament for the treatment of a complication related to AML.

In one particular embodiment the invention provides a medicament that improves the health condition of a patient suffering from AML, in particular a patient undergoing a complication related to AML, said medicament comprising an anti-CD33 CAR expressing T cell of the invention comprising a polypeptide having at least 80% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70.

A complication or disease related to AML may include a preceding myelodysplasia phase, secondary leukemia, in particular secondary AML, high white blood cell count, and absence of Auer rods. Among others, leukostasis and involvement of the central nervous system (CNS), Hyperleukocytosis, residual disease, are also considered as a complication or disease related to AML.

AML Associated Diseases

In one embodiment, the present invention also provides an anti-CD33 CAR expressing T cell for the treatment of a pathological condition related to AML. Preferably, the present invention provides a cell expressing at least one anti-CD33 CAR comprising a polypeptide having at least 80% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70. for the treatment of a pathological condition related to AML.

The present invention provides a medicament for AML related myeloid neoplasms, for acute myeloid leukemia and myelodysplastic syndrome a treatment of relapsed or refractory acute myeloid leukemia, a treatment of relapsed or refractory acute promyelocytic leukemia in adults, a treatment for acute promyeloid leukaemia, a treatment of acute myeloid leukemia in adults over 60 years.

According to another aspect, the present invention provides a composition for the treatment of AML associated diseases, in particular hematologic malignancy related to AML.

Hematologic malignancy related to AML conditions include myelodysplasia syndromes (MDS, formerly known as "preleukemia") which are a diverse collection of hematological conditions united by ineffective production (or dysplasia) of myeloid blood cells and risk of transformation to AML.

In another embodiment, the invention provides a medicament according to the invention that improves the health state of a patient suffering multiple myeloma.

Other pathological conditions or genetic syndromes associated with the risk of AML can be improved with the adequate use of the present invention, said genetic syndromes include Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome).

In one embodiment the present invention provides an anti-CD33 CAR expressing T cell for the treatment of Alzheimer's disease. The present invention provides cells that can be used with the disclosed methods are described in the previous section, preferably cells are anti-CD33 CAR expressing T cells and more preferably TCR and CD33 KO anti-CD33 CAR expressing T cells. Said treatment can be used to treat patients diagnosed wherein a pre-malignant or malignant cancer condition characterized by CD33-expressing cells, especially by an overabundance of CD33-expressing cells. Such conditions are found in hematologic cancers, such as leukemia or malignant lymphoproliferative disorders.

Leukemia can be acute myelogenous leukemia, chronic myelogenous leukemia, melodysplastic syndrome, acute lymphoid leukemia, chronic lymphoid leukemia, and myelodysplastic syndrome.

Lymphoproliferative disorder can be lymphoma, in particular multiple myeloma, non-Hodgkin's lymphoma, Burkitt's lymphoma, and follicular lymphoma (small cell and large cell).

Cancers that may be treated may comprise nonsolid tumors (such as hematological tumors, including but not limited to pre-B ALL (pediatric indication), adult ALL, mantle cell lymphoma, diffuse large B-cell lymphoma and the like. Types of cancers to be treated with the CARs of the invention include, but are not limited leukemia or lymphoid malignancies. Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

Compositions

The present invention provides a composition comprising an anti-CD33 expressing T cells according to the invention and a pharmaceutically acceptable vehicle.

In one embodiment said composition is provided for use as a medicament.

In another embodiment said composition is provided for use as a medicament for the treatment of conditions characterized by CD33-expressing cells, in particular by an overabundance of CD33-expressing cells. Such conditions are found in hematologic cancers, such as leukemia or malignant lymphoproliferative disorders such as B-cell lymphoproliferative disorders.

According to one aspect, the present invention provides a composition comprising an anti-CD33 expressing T cells according to the invention and a pharmaceutically acceptable vehicle for the treatment of CD33+cell-mediated diseases. These CD33+cell mediated diseases include a pre-malignant or malignant cancer condition, inflammation, autoimmune diseases, Alzheimer disease.

In one aspect, a CD33-expressing hematologic cancer cell that can be treated using a composition according to the invention may be a CD33-expressing hematologic cancer stem cell including but not limited to CD33-expressing cancer cell in leukemia (such as acute myelogenous leukemia (AML), chronic myelogenous leukemia, acute lymphoid leukemia, chronic lymphoid leukemia and myelodysplasia syndrome) and malignant lymphoproliferative conditions, including lymphoma (such as multiple myeloma, non-Hodgkin's lymphoma, Burkitt's lymphoma, and small cell- and large cell-follicular lymphoma), or a complication thereof.

A composition comprising an anti-CD33 expressing T cells according to the invention and a pharmaceutically acceptable vehicle is provided for use in a method of reducing the amount, inhibiting the proliferation and/or activity of CD33-expressing hematologic cancer cells in a patient. An exemplary method includes contacting a population of cells comprising a CD33-expressing cell with a CD 33 CART cell of the invention that binds to the CD33-expressing cell.

In a more specific aspect, the present invention provides a composition comprising an anti-CD33 expressing T cells according to the invention and a pharmaceutically acceptable vehicle for its use, in particular in a method for inhibiting the proliferation or reducing the population of cancer cells expressing CD33 in a patient, the methods comprising contacting the CD33-expressing cancer cell population with a CD 33 CART cell of the invention that binds to the CD33-expressing cell, binding of a CD 33 CART cell of the invention to the CD33-expressing cancer cell resulting in the destruction of the CD33-expressing cancer cells.

In certain aspects, the composition comprising a CD 33 CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% (to undetectable level) in a subject with or animal model for myeloid leukemia or another cancer associated with CD33-expressing cells, relative to a negative control.

The present invention also provides a method for preventing, treating and/or managing a disorder or condition associated with CD33-expressing cells (e.g., associated with a hematologic cancer, AML), the methods comprising administering to a subject in need a composition comprising a CD 33 CART cell of the invention that binds to the CD33-expressing cell, in particular a composition comprising an anti-CD33 expressing T cells according to the invention and a pharmaceutically acceptable vehicle. In one aspect, the subject is a human. Non-limiting examples of disorders associated with CD33-expressing cells include inflammatory disorders (such as allergies, Inflammatory bowel diseases BD, Alzheimer disease) and cancers (such as hematological cancers, in particular AML or AML complications).

The present invention also provides a composition for its use or a method for treating a disease comprising the T cell expressing an anti-CD33 CAR of the invention and a pharmaceutically acceptable vehicle, preferably, said anti-CD33 CAR comprising a SEQ ID NO. 1 and a polypeptide having at least 80% to 100% identity with a polypeptide selected from SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, and a combination thereof, and a pharmaceutically acceptable carrier or vehicle. In one aspect, the disease is a diseases as described herein, in particular a hematologic cancer, more particularly a stem cell cancer including but is not limited to leukemia (such as acute myelogenous leukemia (AML), chronic myelogenous leukemia, acute lymphoid leukemia, chronic lymphoid leukemia and myelodysplasia syndrome) and malignant lymphoproliferative conditions, including lymphoma (such as multiple myeloma, non-Hodgkin's lymphoma, Burkitt's lymphoma, and small cell- and large cell-follicular lymphoma), or a complication thereof.

The present invention also provides a composition comprising an anti-CD33 expressing T cells according to the invention and a pharmaceutically acceptable vehicle for its use in a method for inhibiting the proliferation or reducing a CD33-expressing cell population or activity in a patient. An exemplary method includes contacting a population of cells comprising a CD33-expressing cell with a CD 33 CART cell of the invention that binds to the CD33-expressing cell, preferably said anti-CD33 CAR comprises a SEQ ID NO. 1 and a polypeptide having at least 80% to 100% identity with a polypeptide selected from SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, and a combination thereof.

The present invention also provides a composition comprising an anti-CD33 expressing T cells according to the invention and a pharmaceutically acceptable vehicle for its use in a method for preventing, treating and/or managing a disorder or condition associated with CD33-expressing cells (e.g., associated with a hematologic cancer), the methods comprising administering to a subject in need a composition of the invention, wherein said anti-CD33 CAR comprises a SEQ ID NO. 1 and a polypeptide having at least 80% to 100% identity with a polypeptide selected from SEQ ID NO 19, SEQ ID NO 20, SEQ ID NO 21, SEQ ID NO 22, SEQ ID NO 27, SEQ ID NO 28, SEQ ID NO 29, SEQ ID NO 30, SEQ ID NO 35, SEQ ID NO 36, SEQ ID NO 37, SEQ ID NO 38, and a combination thereof, that binds to the CD33-expressing cell. In one aspect, the subject is a human. Non-limiting examples of disorders associated with CD33-expressing cells include autoimmune disorders (such as lupus), inflammatory disorders (such as allergies, IBD, and asthma) and cancers (such as hematological cancers, in particular AML or AML complications).

The present invention also provides a composition for its use comprising the T cell expressing an anti-CD33 CAR of the invention and a pharmaceutically acceptable vehicle, or a method for treating a disease comprising it use, preferably, said anti-CD33 CAR comprising a polypeptide having at least 80% to 100% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70. In one aspect, the disease is a diseases as described herein, in particular a hematologic cancer, more particularly a stem cell cancer including but is not limited to leukemia (such as acute myelogenous leukemia (AML), chronic myelogenous leukemia, acute lymphoid leukemia, chronic lymphoid leukemia and myelodysplasia syndrome) and malignant lymphoproliferative conditions, including lymphoma (such as multiple myeloma, non-Hodgkin's lymphoma, Burkitt's lymphoma, and small cell- and large cell-follicular lymphoma), or a complication thereof.

The present invention also provides a composition comprising an anti-CD33 expressing T cells according to the invention and a pharmaceutically acceptable vehicle for its use in a method for inhibiting the proliferation or reducing a CD33-expressing cell population or activity in a patient. An exemplary method includes contacting a population of cells comprising a CD33-expressing cancer cell with a CD 33 CAR T cell of the invention that binds to the CD33-expressing cell, preferably said anti-CD33 CAR comprises a polypeptide having at least 80% identity with a sequence selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70.

The present invention also provides a composition comprising an anti-CD33 expressing T cells according to the invention and a pharmaceutically acceptable vehicle for its use in a method for preventing, treating and/or managing a disorder or condition associated with CD33-expressing cells (e.g., associated with a hematologic cancer), the methods comprising administering to a subject in need a composition of the invention, wherein said anti-CD33 CAR comprises a polypeptide having at least 80% to 100% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70.

In one aspect, the subject is a human. Non-limiting examples of disorders associated with CD33-expressing cells include autoimmune disorders (such as lupus), inflammatory disorders (such as allergies, IBD, and asthma) and cancers (such as hematological cancers, in particular AML or AML complications).

The present invention also provides a composition comprising an anti-CD33 expressing T cells according to the invention and a pharmaceutically acceptable vehicle for its use in a method for preventing, treating and/or managing a disease associated with CD33-expressing cells, the method comprising administering to a subject in need a composition of the invention that binds to the CD33-expressing cell. In this embodiment, said anti-CD33 CAR comprises a polypeptide having at least 80% to 100% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70. In one aspect, the subject is a human. Non-limiting examples of diseases associated with CD33-expressing cells include Acute Myeloid Leukemia (AML), myelodysplasia, B-cell Acute Lymphoid Leukemia, T-cell Acute Lymphoid Leukemia, hairy cell leukemia, blastic plasmacytoid dendritic cell neoplasm, chronic myeloid leukemia, Hodgkin lymphoma.

The present invention provides a composition comprising an anti-CD33 expressing T cells according to the invention and a pharmaceutically acceptable vehicle for its use in a method for treating or preventing relapse of cancer associated with CD33-expressing cells, the method comprising administering to a subject in need thereof a composition according to the invention, wherein said anti-CD33 CAR comprises a polypeptide having at least 80% to 100% identity with a polypeptide selected from SEQ ID NO: 48, SEQ ID NO: 50, SEQ ID NO: 52, SEQ ID NO: 54, SEQ ID NO: 56, SEQ ID NO: 58, SEQ ID NO: 66, SEQ ID NO: 68, and SEQ ID NO:70 that binds to the CD 33-expressing cell. In another aspect, the methods comprise administering to the subject in need thereof an effective amount of composition according to the invention in combination with an effective amount of another therapy.

In one aspect, the invention provides compositions and methods for treating subjects that have undergone treatment for a disease or disorder associated with elevated expression levels of CD 19, and exhibits a disease or disorder associated with elevated levels of CD33.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Unless otherwise specified, "a," "an," "the," and "at least one" are used interchangeably and mean one or more than one.—Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc: ζ) and have the ability, when expressed in T cells, to redirect antigen recognition based on the monoclonal antibody's specificity. One example of CAR used in the present invention is a CAR directing against CD33 antigen and can comprise as non-limiting example the amino acid sequences: SEQ ID NO: 19 to 42 and preferably the amino acid sequences from SEQ ID NO 48 to 71.

By V1 structure is intended molecules that combine a CD8alpha signal peptide, a VH domain separated to a VL domain by a linker, said VH and VL contributing to the binding to CD33, a Hinge from Fcgamma (γ) RIIIalpha (α)

a transmembrane domain derived from CD8alpha (α)

a cytoplasmic domain derived from 41BB and CD3 zeta (ζ)

By V2 structure is intended molecules with a V1 structure and wherein the transmembrane domain derived from 41BB By V3 structure is intended molecules that combine CD8alpha signal peptide, a VH domain separated to a VL domain by a linker, said VH and VL contributing to the binding to CD33, a Hinge from CD8alpha (α)

a transmembrane domain derived from CD8alpha (α)

a cytoplasmic domain derived from 41BB and CD3 zeta (ζ)

By V4 structure is intended molecules with a V3 structure and wherein the transmembrane domain derived from 41BB.
By V5 structure is intended molecules that combine
  a CD8alpha signal peptide,
  a VH domain separated to a VL domain by a linker, said VH and VL contributing to the binding to CD33,
  a Hinge from IgG1 (α)
  a transmembrane domain derived from CD8alpha (α)
  a cytoplasmic domain derived from 41BB and CD3 zeta (ζ).
By V6 structure is intended molecules with a V5 structure and wherein the transmembrane domain derived from 41BB.
The CAR structures of the invention are illustrated in FIG. 2, preferably in FIG. 3.

The term "chemotherapy" refers to any therapy using a chemical, in particular those used against cancer.—The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Engineered TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA:crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif-PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomega-lovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non-limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory Ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The terms "drug used to treat a cancer, in particular AML" refers to medicament used for the treatment of cancer, in particular AML and are described for example in document PCT/EP2015/055848.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

General Methods:

Inactivation of Specific Gene(s) in Primary T Cells

Inactivation of specific gene(s) in primary T cells may be performed before or after CAR introduction into T cells.

At least one gene, one gene or two genes may be inactivated in one step or in successive steps. In a preferred embodiment two genes may be inactivated at once, preferably TCRalpha gene and CD33 gene.

In general, heterodimeric nuclease, in particular TALE-Nuclease targeting two long sequences (called half targets) separated by a spacer within a target gene is designed and produced.

Each TALE-nuclease construct may be cloned in an appropriate mammalian expression vector. mRNA encoding TALE-nuclease cleaving a targeted genomic sequence may be synthesized from plasmid carrying the coding sequence downstream a promoter.

Cells are purified T cells preactivated with anti-CD3/CD28 coated beads. Cells are transfected with each of the 2 mRNAs encoding both half TALE-nucleases, in particular both half TALE-nucleases and spacer.

Cells may be reactivated with soluble anti-CD28 to measure cell proliferation and the activation marker CD25 detected to assess the activation state of the cells.

Chimeric Antigen Receptors

Nucleic Acids—Vectors

Figure 3:
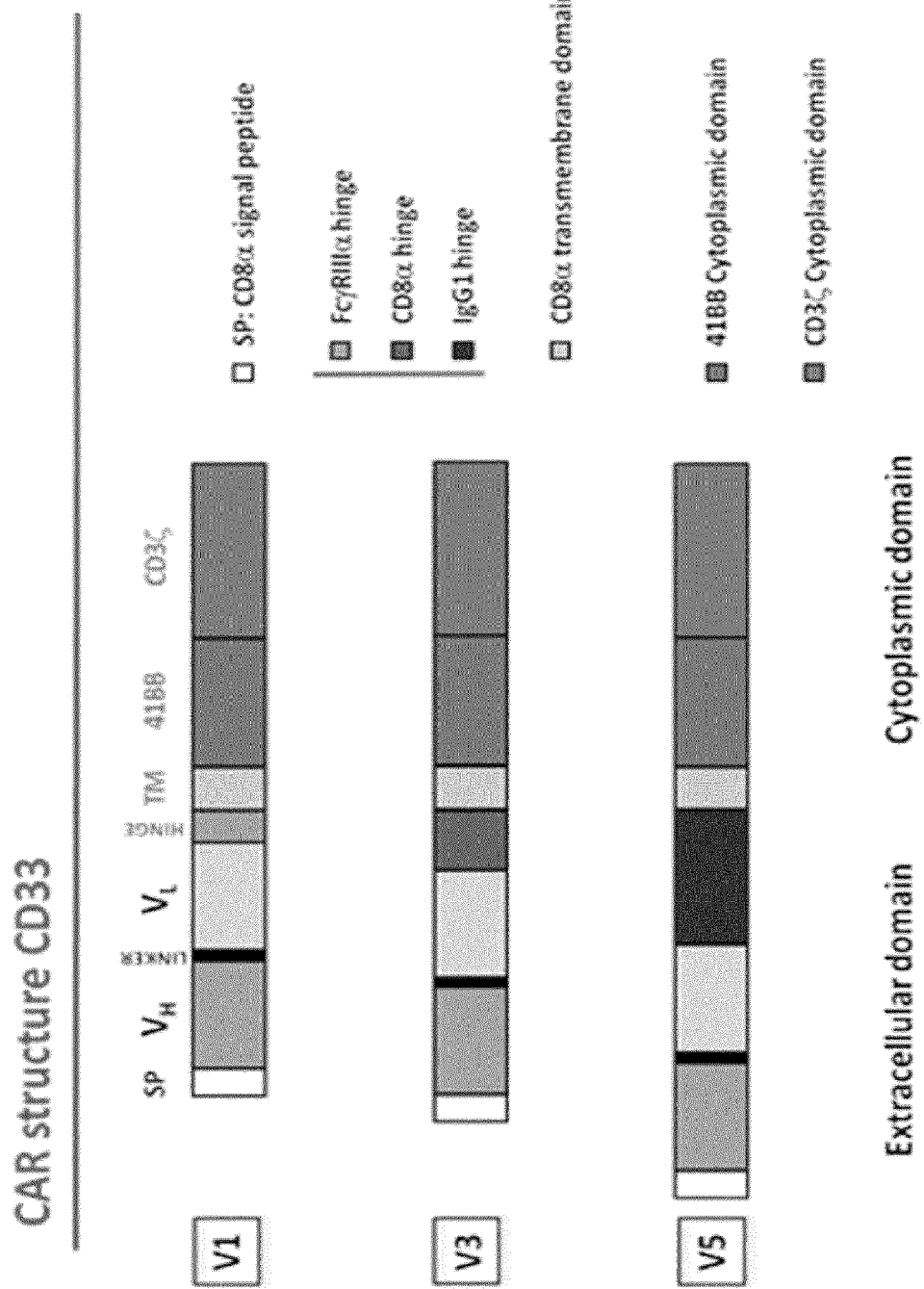
FIG. 3: Schematic representation of different CAR with a V1, V3 or V5 structure.

An acid nucleic (mRNA or lentiviral vector) encoding an anti-CD33 CAR of the invention is constructed according to the architecture designed in FIG. 2 or FIG. 3.

Anti-CD33 CAR lentiviral vectors may be prepared for example as previously described in WO2013176915, WO2013176916, or in WO2014130635, and incorporated herein by reference. Lentiviral vectors are produced by Vectalys SA (Toulouse, France).

CAR mRNAs may be produced using T7 mRNA polymerase and transfections done using Cytopulse technology.

Screening and Selection of Anti-CD33 CAR

Primary T-Cell Cultures

T cells are purified from Buffy coat samples provided by EFS (Etablessiment Français du Sang, Paris, France) using Ficoll gradient density medium. The PBMC layer is recovered and T cells purified using a commercially available T-cell enrichment kit. Purified T cells are activated in X-Vivo™-15 medium (Lonza) using Human IL-2 and Dynabeads Human T activator CD3/CD28.

CAR mRNA Transfection

Transfections of CAR mRNAs encoding the different CAR constructs are performed at Day 4 or Day 11 after T-cell purification and activation.

T-cell transduction with recombinant lentiviral vectors allowing the expression of CAR Transduction of T-cells with recombinant lentiviral vectors are carried out three days after T-cell purification/activation. Lentiviral vectors are produced by Vectalys SA (Toulouse, France), by transfecting genomic and helper plasmids in HEK-293 cells. Transductions may be carried out at various multiplicity of infection (MOI), in particular at a MOI of 5. CAR detection at the surface of T-cells is performed using a recombinant protein consisting on the extracellular domain of the human CD33 protein fused together with a murine IgG1 Fc fragment (produced by LakePharma).

Binding of this protein to the CAR molecule is detected with a PE-conjugated secondary antibody (Jackson Immunoresearch) targeting the mouse Fc portion of the protein, and Degranulation Assay (CD107a Mobilization)

T-cells are incubated together with an equal amount of cells expressing various levels of the CD33 protein. Co-cultures are maintained for at least 6 hours. CD107a staining is performed during cell stimulation, by the addition of a fluorescent anti-CD107a antibody at the beginning of the co-culture. After the 6 h incubation period, cells are stained with a fixable viability dye and fluorochrome-conjugated anti-CD8 and analyzed by flow cytometry. The degranulation activity is determined as the % of CD8+/CD107a+ cells, and by determining the mean fluorescence intensity signal (MFI) for CD107a staining among CD8+ cells.

Degranulation assays are carried out 24 h after mRNA transfection.

IFN Gamma Release Assay 24 h after mRNA transfection, anti-CD33 CAR expressing T-cells are incubated together with cell lines expressing various levels of the CD33 protein for 24 hours at 37° C. The supernatants are recovered and IFN gamma detection in the cell culture supernatants is done by ELISA assay.

Cytotoxicity Assay

CD33 CAR expressing T-cells are incubated together with target cells (expressing various levels of CD33) or (CD33neg) cells in the same well. Target CD33+ and control CD33-target cells are labelled with fluorescent intracellular dyes (eg. CFSE or Cell Trace Violet), before co-culture with for 4 hours at 37° C. After this incubation period, cells are labelled with a fixable viability dye and analyzed by flow cytometry. Viability of each cellular population (target cells or CD33neg control cells) is determined and the % of specific cell lysis is calculated. Cytotoxicity assays are carried out 48 h after mRNA transfection.

Anti-Tumor Mouse Model

Immuno deficient NOG mice are intravenously (iv) injected with CD33 expressing-Luciferase cells. Optionally, mice receive an anti-cancer treatment before injection with anti-CD33 CAR+ T-cells. Mice are then iv injected (eg either 2 or 7 days after injection of the tumor cell line) with different doses of anti-CD33 CAR+ T-cells to be tested, or with T-cells that were not transduced with the CAR lentiviral vector. Bioluminescent signals are determined at the day of T-cell injection (D0), at D7, 14, 21, 28 and 40 after T-cell injection in order to follow tumoral progression in the different animals.

Having generally described this invention, a further understanding can be obtained by reference to certain specific examples, which are provided herein for purposes of illustration only, and are not intended to be limiting unless otherwise specified.

EXAMPLES

Construction of CD33 CAR Using Various Anti-CD33 Antibody Fragments

Different architectures of CAR were designed (FIG. 3) namely V1 to V6. As a first step, 4 different scFv's from M195, DRB2, m2H12 and My9.6 antibody were constructed to generate Chimeric Antigen Receptors (CARs) (SEQ ID NO 48 to SEQ ID NO 71) in T cells.

Example 1: Proliferation of TCRalpha Inactivated Cells Expressing a CD33-CAR

Primary T-Cell Cultures

T cells were purified from various buffy coat samples provided by EFS (Etablessiment Français du Sang, Paris, France) using Ficoll gradient density medium. The PBMC layer was recovered and T cells were purified using a commercially available T-cell enrichment kit (Stem Cell Technologies). Purified T cells were activated in X-Vivo™-15 medium (Lonza) supplemented with 20 ng/mL Human IL-2, 5% Human Serum, and Dynabeads Human T activator CD3/CD28 at a bead:cell ratio 1:1 (Life Technologies). After activation cells were grown and maintained in X-Vivo™-15 medium (Lonza) supplemented with 20 ng/mL Human IL-2 and 5% Human Serum.

CAR mRNA Transfection

Transfections of each CD33 CAR generated using various anti-CD33 antibody fragments were done at Day 4 or Day 11 after T-cell purification and activation. 5 million cells were transfected with 15 μg of mRNA encoding the different CAR constructs. CAR mRNAs were produced using the mMESSAGE mMACHINE T7 Kit (Life Technologies) and purified using RNeasy Mini Spin Columns (Qiagen). Transfections were done using Cytopulse technology, by applying two 0.1 mS pulses at 3000V/cm followed by four 0.2 mS pulses at 325V/cm in 0.4 cm gap cuvettes in a final volume of 200 μg of "Cytoporation buffer T" (BTX Harvard Apparatus). Cells were immediately diluted in X-Vivo™-15 media (Lonza) and incubated at 37° C. with 5% $CO_2$. IL-2 was added 2 h after electroporation at 20 ng/mL.

Primary T Cells Transduction

T-Cell Transduction

Transduction of T-cells with recombinant lentiviral vectors expression the antiCD33 CAR were carried out three days after T-cell purification/activation. Lentiviral vectors produced by Vectalys SA (Toulouse, France) were used. Anti-CD33 CAR detection at the surface of T-cells is performed using a recombinant protein consisting on the extracellular domain of the human CD33 protein fused together with a murine IgG1 Fc fragment (produced by LakePharma). Binding of this protein to the anti-CD33 CAR molecule is detected with a PE-conjugated secondary antibody (Jackson Immunoresearch) targeting the mouse Fc portion of the protein, and analyzed by flow cytometry.

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 10.

TABLE 10

TAL-nucleases targeting TCRalpha gene

| Target | Target sequence | Repeat sequence | Half TALE-nuclease |
|---|---|---|---|
| TRAC_T01 | TTGTCCCACAGAT ATCCAgaaccctg acccctgCCGTG TACCAGCTGAGA (SEQ ID NO: 43) | Repeat TRAC_T01-L (SEQ ID NO: 44) Repeat TRAC_T01-R (SEQ ID NO: 45) | TRAC_T01-L TALEN (SEQ ID NO: 46) TRAC_T01-R TALEN (SEQ ID NO: 47) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with anti-CD3/CD28 coated beads were transfected with each of the 2 mRNAs encoding both half TRAC_T01 TALE-nucleases. 48 hours post-transfection, different groups of T cells from the same donor were respectively transduced with a lentiviral vector encoding one of the CD33 CAR previously described (SEQ ID NO: 19 to 42). 2 days post-transduction, $CD3_{NEG}$ cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. Increased proliferation in TCR alpha inactivated cells expressing the CD33 CARs, especially when reactivated with anti-CD28, was observed compared to non-transduced cells.

To investigate whether the human T cells expressing the CD33CAR display activated state, the expression of the activation marker CD25 are analyzed by FACS 7 days post transduction. The purified cells transduced with the lentiviral vector encoding CD33 CAR assayed for CD25 expression at their surface in order to assess their activation in comparison with the non-transduced cells. Increased CD25 expression is expected both in CD28 reactivation or no reactivation conditions.

The present invention provided a CD33 specific CAR T cell wherein the level of TCR at the cell surface was below detected.

Example 2

Inactivation of the CD33 Gene

To inactivate the CD33 gene, heterodimeric TALE-nuclease targeting two sequences (called Sequence bound by TALEN Left and Sequence bound by TALEN Right, see table 11) separated by a 10 or 15-bp spacer within CD33 gene were designed and produced as described below. Each half target is recognized by repeats of the half TALE-nucleases listed in Table 11. The constructs were then introduced into T cells together with and at the same time that those designed to inactivate the TCR alpha gene.

TABLE 11

TAL-nucleases targeting TCRaIpha gene

| Target | Target sequences |
|---|---|
| TALEN1_CD33_Exon3 | TGCATCCCCTCTTTCTCCTCACTAGACTTGAC CCACAGGCCCAA (SEQ ID NO: 72) |
| TALEN2_CD33_Exon3 | TTCTCCTCACTAGACTTGACCCACAGGCCCAA AATCCTCATCCCTGGCA (SEQ ID NO: 73) |
| TALEN1_CD33_Exon4 | TCCTCTCCTAGATGTTCCACAGAACCCAACAA CTGGTATCTTTCCAGGA (SEQ ID NO: 74) |
| TALEN2_CD33_Exon4 | TCCTAGATGTTCCACAGAACCCAACAACTGGT ATCTTTCCAGGA (SEQ ID NO: 75) |

| Sequence bound by TALEN Left | Spacer | Sequence bound by TALEN Right |
|---|---|---|
| TGCATC-CCCTCTTTCTC (SEQ ID NO: 76) | CTCACTAGAC (SEQ ID NO: 80) | TTGACCCACAGGCCCAA (SEQ ID NO: 84) |
| TTCTCCTCACTA-GACTT (SEQ ID NO: 77) | GACCCACAGGCCCAA (SEQ ID NO: 81) | AATCCTCATCCCTGGCA (SEQ ID NO: 85) |
| TCCTCTCCTAGAT-GTTC (SEQ ID NO: 78) | CACAGAACCCAACAA (SEQ ID NO: 82) | CTGGTATCTTTCCAGGA (SEQ ID NO: 86) |
| TCCTAGATGTTC-CACAG (SEQ ID NO: 79) | AACCCAACAA (SEQ ID NO: 83) | CTGGTATCTTTCCAGGA (SEQ ID NO :87) |

In the resulting cells, the extracellular domain of CD33 is truncated. Double staining of the resulting cells and analysis by flow cytometry indicated a drop in cell surface expression of CD33 and of TCR as compared to control (mock-transfected) cells.

Alternatively, purified TCR KO T cells preactivated during 72 hours with anti-CD3/CD28 coated beads may be used for CD33 inactivation.

To investigate the activated state of the human TCR KO and CD33 KO T cells expressing the CD33 CAR, the expression of the activation marker CD25 are analyzed by FACS 7 days post transduction.

Anti-CD33 CARs T cells and anti-CD33 CARs T cells wherein TCR alpha gene and/or CD33 gene is inactivated and wherein CAR is corresponding to architectures V1, V3 and V5, can be produced.

Cells are designated as "T cells" or "CD33 CAR", for convenience.

Example 3

Degranulation Activity of CD33 CAR Generated Using Various Anti-CD33 Antibody Fragments The activity of the constructs V1, V3 and V5 of M195, m2H12 and My9.6 as described above was first determined upon transient expression in human primary T-cells.

Degranulation Assay (CD107a Mobilization)

T-cells were then incubated in 96-well plates (40,000 cells/well), together with an equal amount of cells expressing various levels of the CD33 protein. Co-cultures were maintained in a final volume of 100 µl of X-Vivo™-15 medium (Lonza) for 6 hours at 37° C. with 5% $CO_2$. CD107a staining was done during cell stimulation, by the addition of a fluorescent anti-CD107a antibody at the beginning of the co-culture, together with 1 µg/ml of anti-CD49d, 1 µg/ml of anti-CD28, and 1× Monensin solution. After the 6 h incubation period, cells were stained with a fixable viability dye and fluorochrome-conjugated anti-CD8 and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection.

Figure 6:
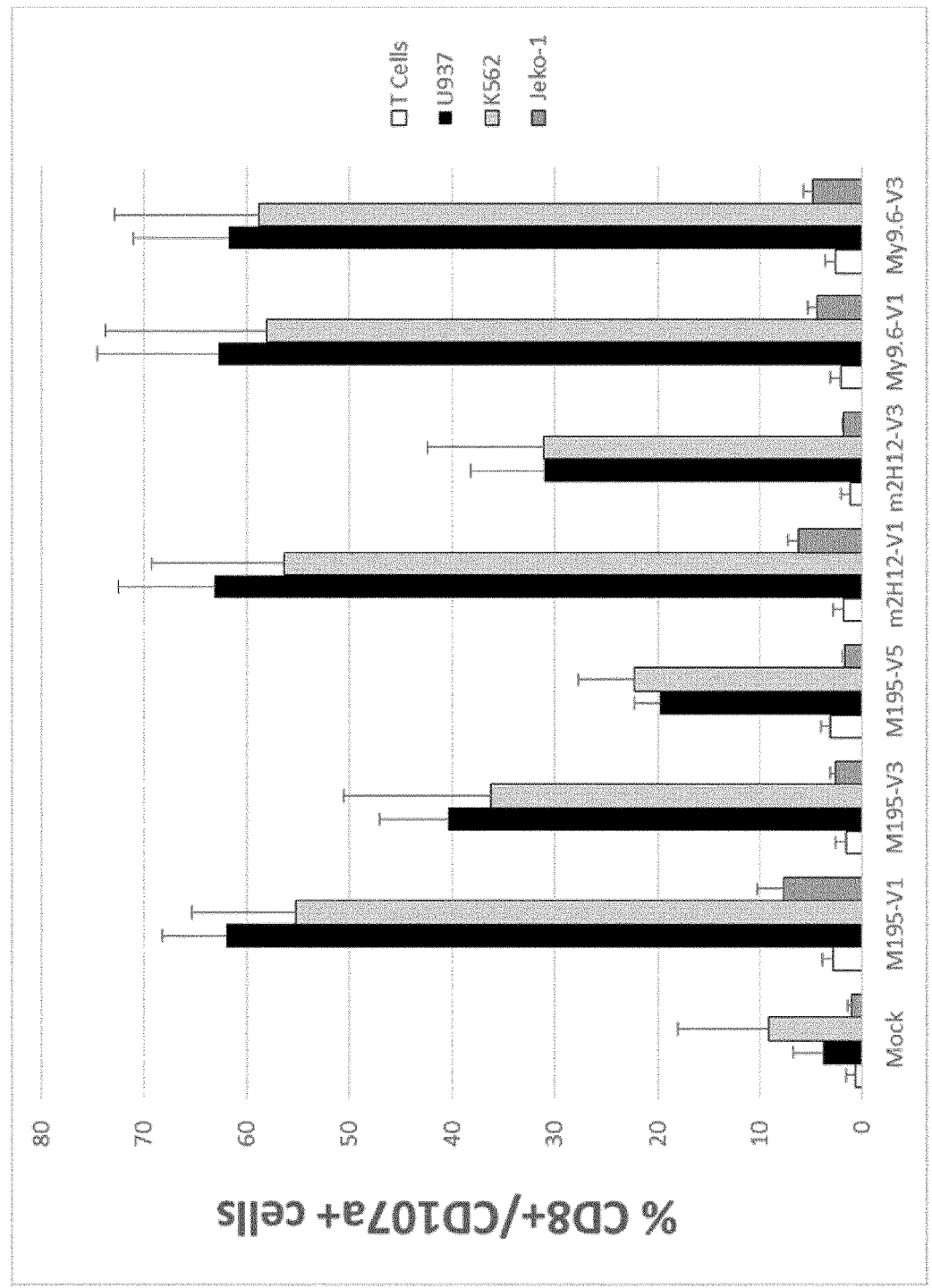
FIG. 6: Degranulation activity (% CD8/CD107a+ cells) of 7 constructions: M195-V1, M195-V3, M195-V5, m2H12-V1, m2H12-V3 and My9.6-V1 and My9.6-V3 (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with cells expressing high or intermediate levels of CD33 (U937 and K562, respectively), or with cells that do not express CD33 (Jeko-1). The data is presented as a percentage (%) of degranulation.
Figure 7:
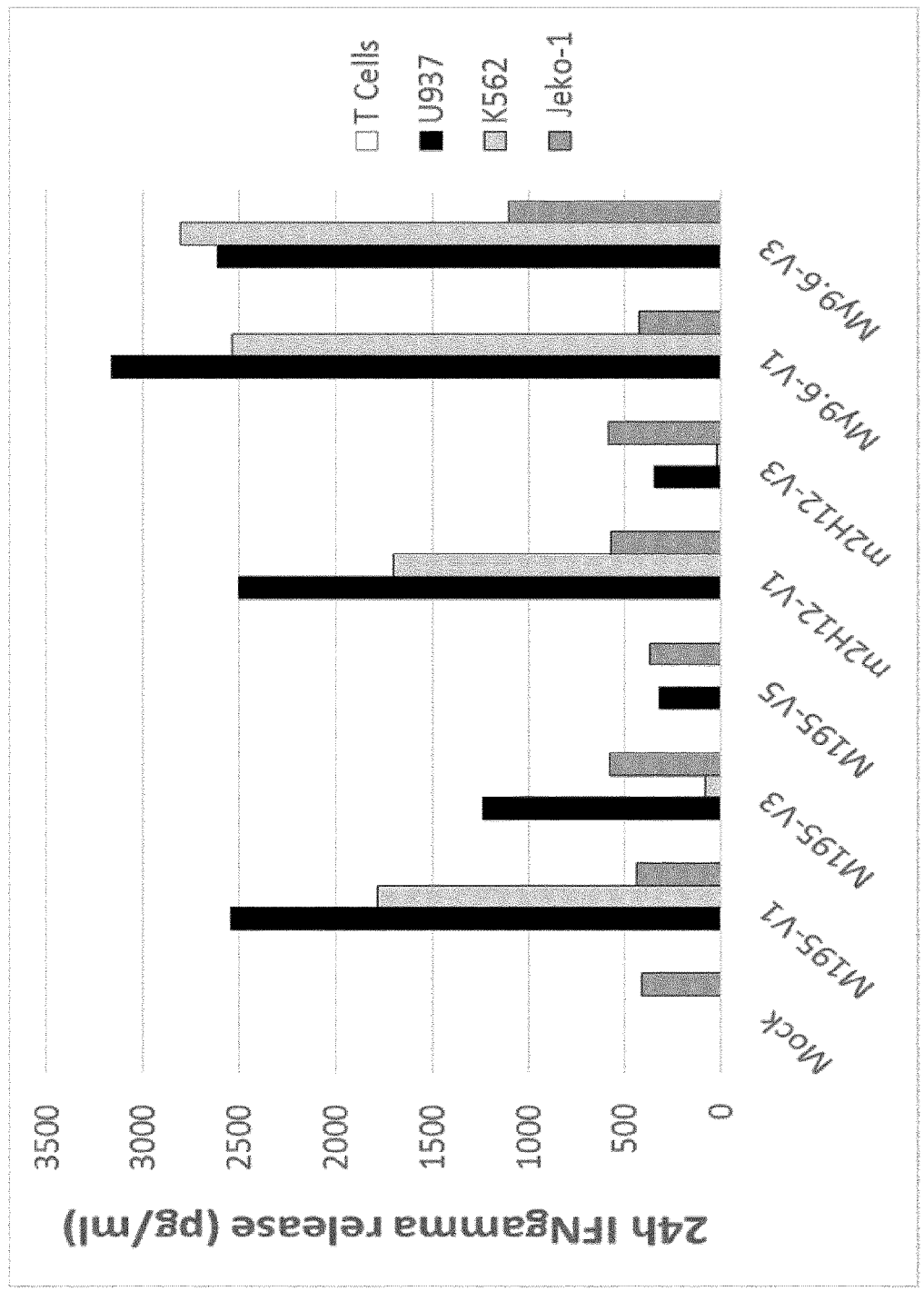
FIG. 7: Amount of IFN gamma released by anti-CD33 CAR expressing T-cells when co-cultured for 24 h with cells expressing different levels of CD33 (U937 and K562), or with cells that do not express CD33 (Jeko-1). IFN gamma release from T-cells cultured alone, in the same conditions that the co-cultures, is also shown. The experiments were done using three independent donors, and results from one representative donor are shown here.
Figure 8:
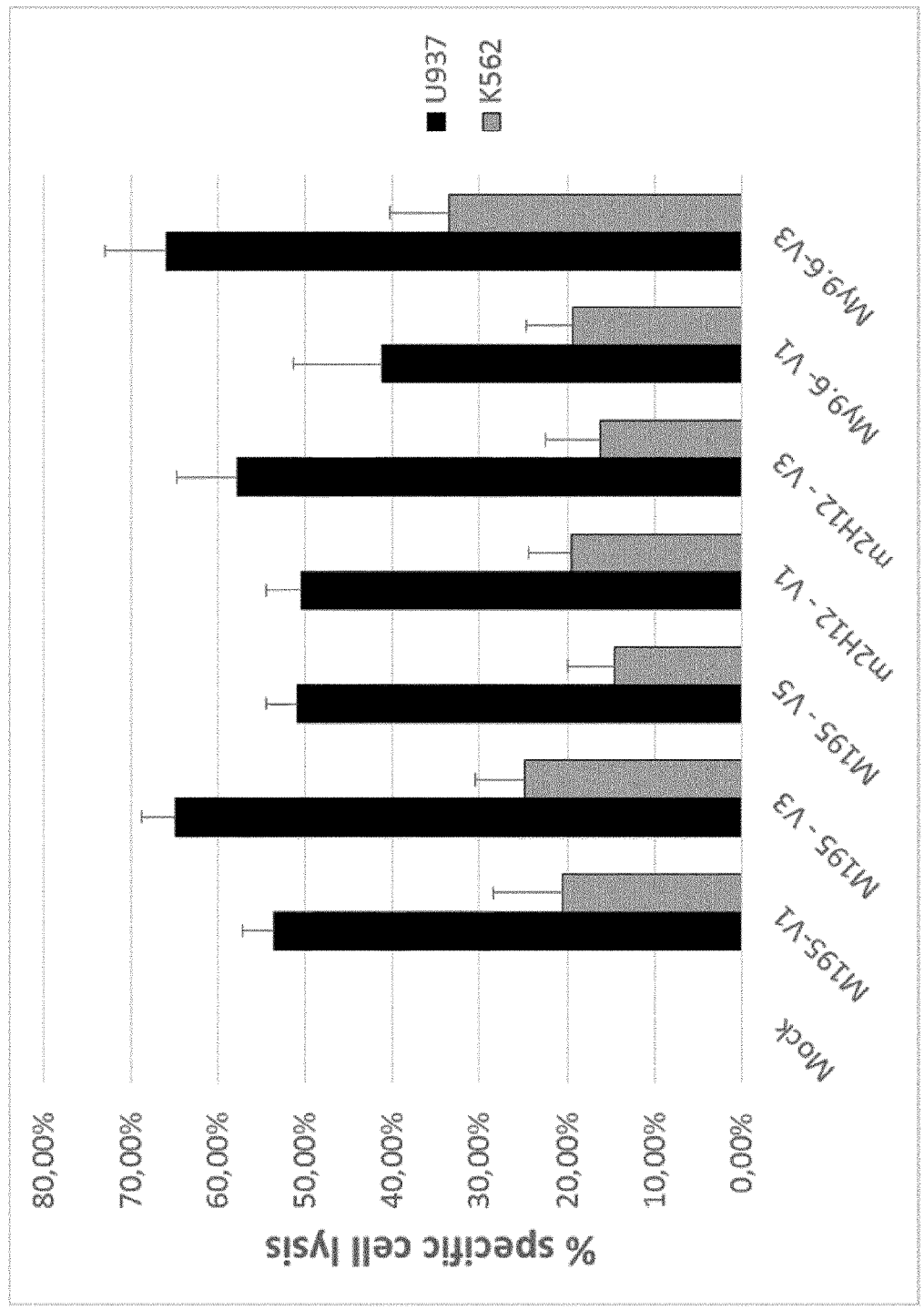
FIG. 8: Specific cytolytic activity of anti-CD33 CAR expressing-T cells. Assays were done 48 h after CAR mRNA transfection. T-cells were co-cultured with U937+Jeko or K562+Jeko cells for 4 hours. Cellular viability for each of the cell lines was determined at the end of the co-cultured and a specific cell lysis percentage was calculated.

Among the CAR molecules generated as illustrated in FIG. 3, 9 were tested for their degranulation activity (FIG. 4 to FIG. 6) and 7 of them were selected for further activity tests: interferon gamma release and cell lysis (FIG. 7 and FIG. 8).

Degranulation activity of each of the CAR comprising a M195, m2H12 or My9.6 scFv within one of the three architectures (v1: FcgRIII-hinge/CD8-transmembrane, v3: CD8-hinge/CD8-transmembrane, or v5: IgG1-hinge/CD8-transmembrane), was measured when CAR+ T-cells were co-cultured for 6 hours with CD33 expressing cells (U937), or with cells expressing undetectable level CD33 (Jeko or Jeko-1). The results are illustrated in FIG. 4 to FIG. 6.

Figure 4:
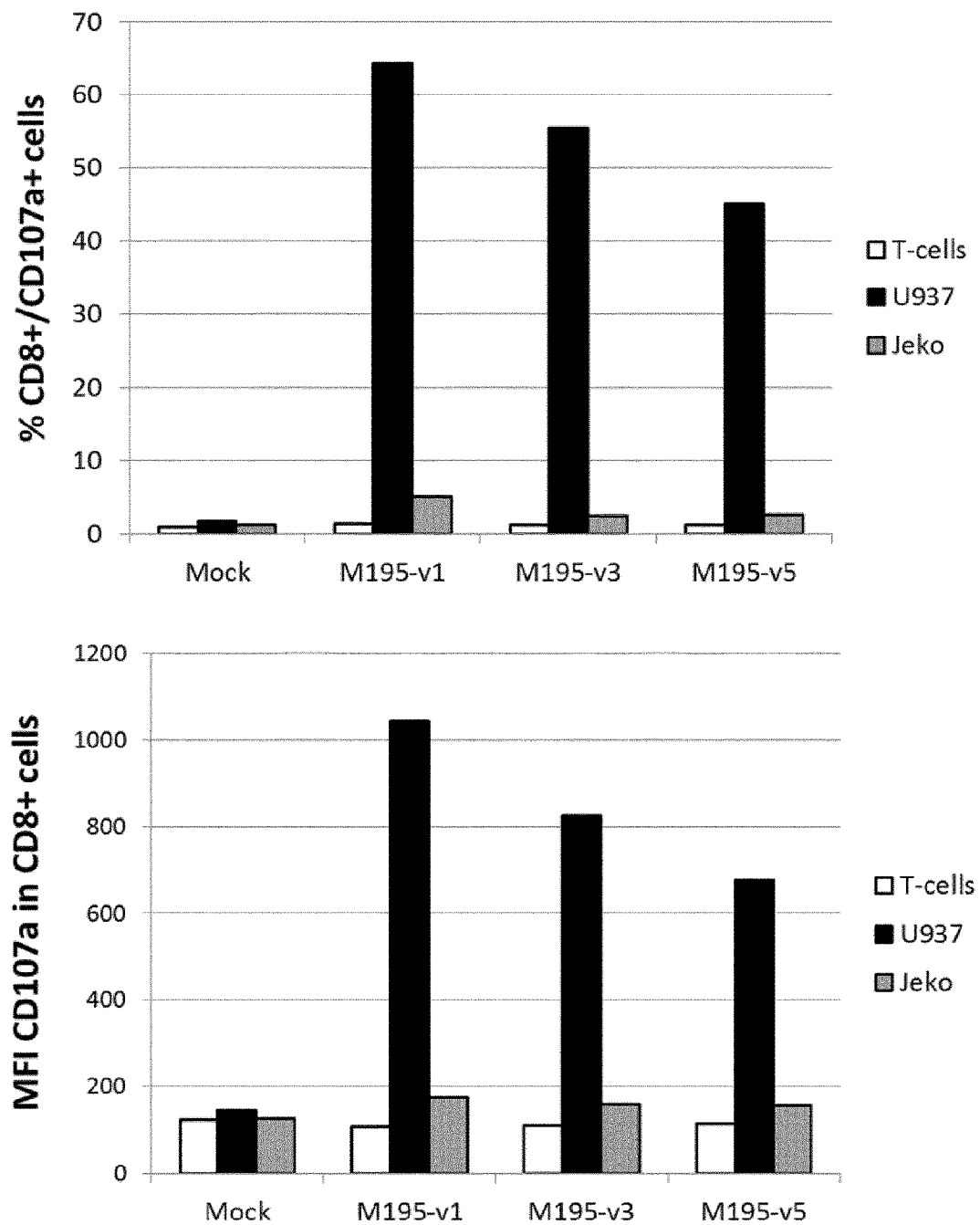
FIG. 4: Degranulation activity (% CD8/CD107a+ cells and mean fluorescence intensity (MFI) CD107a in CD8+ cells) of the M195 scFv with the three architectures (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with CD33 expressing cells (U937), or with cells that do not express CD33 (Jeko). The data is presented as a percentage (%) of degranulation and mean fluorescence intensity (MFI).

FIG. 4 shows degranulation activity (% CD8/CD107a+ cells and MFI CD107a in CD8+ cells) of the M195 scFv with the three architectures (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with CD33 expressing cells (U937), or with cells that do not express CD33 (Jeko). The data is presented as a percentage (%) of degranulation and mean fluorescence activity (MFI).

Figure 5:
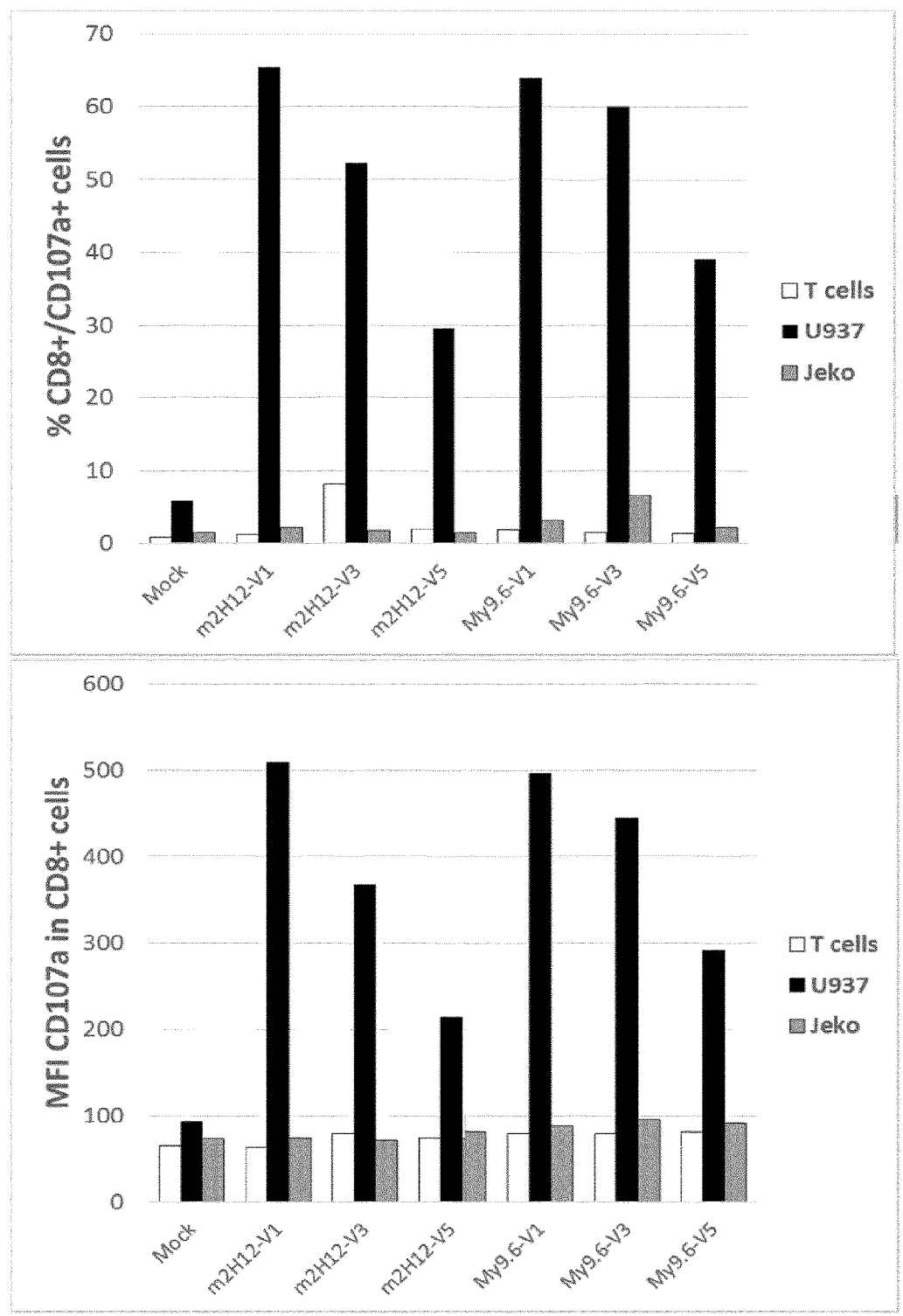
FIG. 5: Degranulation activity (% CD8/CD107a+ cells and MFI CD107a in CD8+ cells) of the m2H12 and My9.6 scFvs with the three architectures (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with CD33 expressing cells (U937), or with cells that do not express CD33 (Jeko). The data is presented as a percentage (%) of degranulation and mean fluorescence intensity (MFI).

FIG. 5 shows degranulation activity (% CD8/CD107a+ cells and MFI CD107a in CD8+ cells) of the m2H12 and My9.6 scFvs with the three architectures (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with CD33 expressing cells (U937), or with cells that do not express CD33 (Jeko). The data is presented as a percentage (%) of degranulation and mean fluorescence activity (MFI).

FIG. 6 shows degranulation activity (% CD8/CD107a+ cells) of 7 constructions: M195-V1, M195-V3, M195-V5, m2H12-V1, m2H12-V3 and My9.6-V1 and My9.6-V3 (v1: FcgRIII-hinge/CD8-transmembrane, v3: CD8-hinge/CD8-transmembrane, v5: IgG1-hinge/CD8-transmembrane), when CAR+ T-cells were co-cultured for 6 hours with cells expressing high or intermediate levels of CD33 (U937 and K562, respectively), or with cells that do not express CD33 (Jeko-1). The data is presented as a percentage (%) of degranulation and mean fluorescence activity (MFI).

Interferon Gamma Release and Cell Lysis Induced by T Cells Expressing CD33 CAR Generated Using Anti-CD33 scFv Antibody Fragments Derived From M195, M2H12, and My9.6

For this, T-cells from various donors were isolated from buffy-coat samples and activated using CD3/CD28 beads. Cells were transiently transfected with mRNAs encoding the different candidates at D11 after activation.

CAR activity was assessed by measuring the IFN gamma release, and the cytotoxic activity when co-cultured with cells expressing various levels of CD33 as follows.

IFN Gamma Release Assay

Anti-CD33 CAR-expressing T-cells were incubated in 96-well plates (40,000 cells/well), together with cell lines expressing various levels of the CD33 protein. Co-cultures were maintained in a final volume of 100 µl of X-Vivo™-15 medium (Lonza) for 24 hours at 37° C. with 5% $CO_2$. After this incubation period the plates were centrifuged at 1500 rpm for 5 minutes and the supernatants were recovered in a new plate. IFN gamma detection in the cell culture supernatants was done by ELISA assay. The IFN gamma release assays were carried by starting the cell co-cultures 24 h after mRNA transfection.

FIG. 7 shows the amount of IFN gamma released by CD33 car T-cells (T cells) when co-cultured for 24 hwith cells expressing different levels of CD33 (U937 and K562), or with cells that do not express CD33 (Jeko-1). IFN gamma release from T-cells cultured alone, in the same conditions that the co-cultures, is also shown. The experiments were done for three independent donors, and results from a representative donor are shown here.

T cells expressing CD33 CAR generated using anti-CD33 scFv antibody fragments derived from M195, M2H12, and My9.6 were then tested for their capacity to lyse CD33+ expressing target cancer cells (U937: Human leukemic monocyte lymphoma cell and K562 human leukemic cell derived from of a patient with chronic myelogenous leukemia (CML) as follows.

Cytotoxicity Assay

Anti-CD33 CAR-expressing T-cells were incubated in 96-well plates (100,000 cells/well), together with 10,000 target cells (expressing CD33) and 10,000 control (CD33neg) cells in the same well. Target and control cells were labelled with fluorescent intracellular dyes (CFSE or Cell Trace Violet) before co-culturing them with CAR+ T-cells. The co-cultures were incubated for 4 hours at 37° C. with 5% $CO_2$. After this incubation period, cells were labelled with a fixable viability dye and analyzed by flow cytometry. Viability of each cellular population (target cells or CD33neg control cells) was determined and the % of specific cell lysis was calculated. Cytotoxicity assays were carried out 48 h after mRNA transfection.

FIG. 8 shows the specific cytolytic activity of CAR-T cells. Assays were done 48 h after CAR mRNA transfection. T-cells were co-cultured with U937+Jeko or K562+Jeko cells for 4 hours. Cellular viability for each of the cell lines was determined at the end of the co-cultured and a specific cell lysis percentage was calculated.

All constructions were active, with My9.6 V3 (My9.6-3, SEQ ID NO 68) CAR exhibiting the higher overall activity as compared to control than other CARS.

The above examples demonstrate that the exemplified CAR structures (V1, V3 and V5) comprising a VH-Linker-VL sequence binding to CD33 are active in all assay.

CARs having the structures V1 and V3 were found particularly active in the degranulation assay, INFy release assay and cytotoxic assay see FIGS. 4 to 8.

The present invention provides therefore an anti-CD33 CAR expressing T cell active against cancer cells.

EXAMPLES OF CAR POLYPEPTIDE SEQUENCES

M195-1
(SEQ ID NO. 1 + SEQ ID NO. 19)

MALPVTALLLPLALLLHAARP EVQLQQSGPELVKPGASVKISCKASGYTFTDYNMHWVKQS

HGKSLEWIGYIYPYNGGTGYNQKFKSKATLTVDNSSSTAYMDVRSLTSEDSAVYYCARGRP

AMDYWGQGTSVTVSS GGGGSGGGGSGGGGS DIVLTQSPASLAVSLGQRATISCRASESV

DNYGISFMNWFQQKPGQPPKLLIYAASNQGSGVPARFSGSGSGTDFSLNIHPMEEDDTAM

```
YFCQQSKEVPWTFGGGTKLEIKGLAVSTISSFFPPGYQIYIWAPLAGTCGVLLLSLVITLYCK
RGRKKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEIGMKG
ERRRGKGHDGLYQGLSTATKDTYDALHMQALPPR

M195-2
                                         (SEQ ID NO. 1 + SEQ ID NO. 20)
MALPVTALLLPLALLLHAARPEVQLQQSGPELVKPGASVKISCKASGYTFTDYNMHWVKQS
HGKSLEWIGYIYPYNGGTGYNQKFKSKATLTVDNSSSTAYMDVRSLTSEDSAVYYCARGRP
AMDYWGQGTSVTVSSGGGGSGGGGSGGGGSDIVLTQSPASLAVSLGQRATISCRASESV
DNYGISFMNWFQQKPGQPPKLLIYAASNQGSGVPARFSGSGSGTDFSLNIHPMEEDDTAM
YFCQQSKEVPWTFGGGTKLEIKGLAVSTISSFFPPGYQIISFFLALTSTALLFLLFFLTLRFSVV
KRGRKKLLYIFKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMAEAYSEIGMK
GERRRGKGHDGLYQGLSTATKDTYDALHMQALPPR

M195-3
                                         (SEQ ID NO. 1 + SEQ ID NO. 21)
MALPVTALLLPLALLLHAARPEVQLQQSGPELVKPGASVKISCKASGYTFTDYNMHWVKQS
HGKSLEWIGYIYPYNGGTGYNQKFKSKATLTVDNSSSTAYMDVRSLTSEDSAVYYCARGRP
AMDYWGQGTSVTVSSGGGGSGGGGSGGGGSDIVLTQSPASLAVSLGQRATISCRASESV
DNYGISFMNWFQQKPGQPPKLLIYAASNQGSGVPARFSGSGSGTDFSLNIHPMEEDDTAM
YFCQQSKEVPWTFGGGTKLEIKTTTPAPRPPTPAPTIASQPLSLRPEACRPAAGGAVHTRG
LDFACDIYIWAPLAGTCGVLLLSLVITLYCKRGRKKLLYIFKQPFMRPVQTTQEEDGCSCRFP
EEEEGGCELRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYDALHMQALP
PR

M195-4
                                         (SEQ ID NO. 1 + SEQ ID NO. 22)
MALPVTALLLPLALLLHAARPEVQLQQSGPELVKPGASVKISCKASGYTFTDYNMHWVKQS
HGKSLEWIGYIYPYNGGTGYNQKFKSKATLTVDNSSSTAYMDVRSLTSEDSAVYYCARGRP
AMDYWGQGTSVTVSSGGGGSGGGGSGGGGSDIVLTQSPASLAVSLGQRATISCRASESV
DNYGISFMNWFQQKPGQPPKLLIYAASNQGSGVPARFSGSGSGTDFSLNIHPMEEDDTAM
YFCQQSKEVPWTFGGGTKLEIKTTTPAPRPPTPAPTIASQPLSLRPEACRPAAGGAVHTRG
LDFACDIISFFLALTSTALLFLLFFLTLRFSVVKRGRKKLLYIFKQPFMRPVQTTQEEDGCSCR
FPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQ
ALPPR

M195-5
                                         (SEQ ID NO. 1 + SEQ ID NO. 23)
MALPVTALLLPLALLLHAARPEVQLQQSGPELVKPGASVKISCKASGYTFTDYNMHWVKQS
HGKSLEWIGYIYPYNGGTGYNQKFKSKATLTVDNSSSTAYMDVRSLTSEDSAVYYCARGRP
AMDYWGQGTSVTVSSGGGGSGGGGSGGGGSDIVLTQSPASLAVSLGQRATISCRASESV
DNYGISFMNWFQQKPGQPPKLLIYAASNQGSGVPARFSGSGSGTDFSLNIHPMEEDDTAM
YFCQQSKEVPWTFGGGTKLEIKEPKSPDKTHTCPPCPAPPVAGPSVFLFPPKPKDTLMIAR
TPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEALHNHYT
```

```
QKSLSLSPGKIYIWAPLAGTCGVLLLSLVITLYCKRGRKKLLYIFKQPFMRPVQTTQEEDGCS

CRFPEEEEGGCELRVKFSRSADAPAYQQGQNQLYNELNLGRREEYDVLDKRRGRFDPEMG

GKPRRKNPQEGLYNELQKDKMAEAYSEIGMKGERRRGKHDGLYQGLSTATKDTYDALH

MQALPPR

M195-6
                                            (SEQ ID NO. 1 + SEQ ID NO. 24)
MALPVTALLLPLALLLHAARPEVQLQQSGPELVKPGASVKISCKASGYTFTDYNMHWVKQS

HGKSLEWIGYIYPYNGGTGYNQKFKSKATLTVDNSSSTAYMDVRSLTSEDSAVYYCARGRP

AMDYWGQGTSVTVSSGGGGSGGGGSGGGGSDIVLTQSPASLAVSLGQRATISCRASESV

DNYGISFMNWFQQKPGQPPKLLIYAASNQGSGVPARFSGSGSGTDFSLNIHPMEEDDTAM

YFCQQSKEVPWTFGGGTKLEIKEPKSPDKTHTCPPCPAPPVAGPSVFLFPPKPKDTLMIAR

TPEVTCVVVDVSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSLTCLLVKGFYPSDIA

VEWESNGQPENNYKTTPPVLDSDGSFFLYSKLTVDKSRWQQGNVFSCSVMHEALHNHYT

QKSLSLSPGKIISFFLALTSTALLFLLFFLTLRFSVVKRGRKKLLYIFKQ[FMRPVQTTQEEDG

CSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKHDGLYQGLSTATKDTYDA

LHMQALPPR m2H12-1
                                            (SEQ ID NO. 1 + SEQ ID NO. 25)
MALPVTALLLPLALLLHAARPQVQLQQSGPELVRPGTFVKISCKASGYTFTNYDINWVNQRP

GQGLEWIGWIYPGDGSTKYNEKFKAKATLTADKSSSTAYLQLNNLTSENSAVYFCASGYED

AMDYWGQGTSVTVSSGGGGSGGGGSGGGGSDIKMTQSPSSMYASLGERVIINCKASQDI

NSYLSWFQQKPGKSPKTLIYRANRLVDGVPSRFSGSGSGQDYSLTISSLEYEDMGIYYCLQ

YDEFPLTFGAGTKLELKRGLAVSTISSFFPPGYQIYIWAPLAGTCGVLLLSLVITLYCKRGRKK

LLYIFKQPFMRPVQTTQEEDGCSCRFPEEEEGGCELRVKFSRSADAPAYQQGQNQLYNEL

NLGRREEYDVLDKRRGRDPEMGGKPRRKNPQEGLYNELQKDKMAEAYSEIGMKGERRRG

KGHDGLYQGLSTATKDTYDALHMQALPPR m2H12-2
                                            (SEQ ID NO. 1 + SEQ ID NO. 26)
MALPVTALLLPLALLLHAARPQVQLQQSGPELVRPGTFVKISCKASGYTFTNYDINWVNQRP

GQGLEWIGWIYPGDGSTKYNEKFKAKATLTADKSSSTAYLQLNNLTSENSAVYFCASGYED

AMDYWGQGTSVTVSSGGGGSGGGGSGGGGSDIKMTQSPSSMYASLGERVIINCKASQDI

NSYLSWFQQKPGKSPKTLIYRANRLVDGVPSRFSGSGSGQDYSLTISSLEYEDMGIYYCLQ

YDEFPLTFGAGTKLELKRGLAVSTISSFFPPGYQIISFFLALTSTALLFLLFFLTLRFSVVKRGR

KKLLYIFKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIGMKGERR

RGKGHDGLYQGLSTATKDTYDALHMQALPPR m2H12-3
                                            (SEQ ID NO. + SEQ ID NO. 27)
MALPVTALLLPLALLLHAARPQVQLQQSGPELVRPGTFVKISCKASGYTFTNYDINWVNQRP

GQGLEWIGWIYPGDGSTKYNEKFKAKATLTADKSSSTAYLQLNNLTSENSAVYFCASGYED

AMDYWGQGTSVTVSSGGGGSGGGGSGGGGSDIKMTQSPSSMYASLGERVIINCKASQDI

NSYLSWFQQKPGKSPKTLIYRANRLVDGVPSRFSGSGSGQDYSLTISSLEYEDMGIYYCLQ

YDEFPLTFGAGTKLELKRTTTPAPRPPTPAPTIASQPLSLRPEACRPAAGGAVHTRGLDFAC
```

```
DIYIWAPLAGTCGVLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR m2H12-4
                                        (SEQ ID NO. 1 + SEQ ID NO. 28)
MALPVTALLLPLALLLHAARPQVQLQQSGPELVRPGTFVKISCKASGYTFTNYDINWVNQRP
GQGLEWIGWIYPGDGSTKYNEKFKAKATLTADKSSSTAYLQLNNLTSENSAVYFCASGYED
AMDYWGQGTSVTVSSGGGGSGGGGSGGGGSDIKMTQSPSSMYASLGERVIINCKASQDI
NSYLSWFQQKPGKSPKTLIYRANRLVDGVPSRFSGSGSGQDYSLTISSLEYEDMGIYYCLQ
YDEFPLTFGAGTKLELKRTTTPAPRPPTPAPTIASQPLSLRPEACRPAAGGAVHTRGLDFAC
DIISFFLALTSTALLFLLFFLTLRFSVVKRGRKKLLYIFKQPFMRPVQTTQEEDGCSCRFPEEE
EGGCELRVKFSRSADAPAYQQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR m2H12-5
                                        (SEQ ID NO. 1 + SEQ ID NO. 29)
MALPVTALLLPLALLLHAARPQVQLQQSGPELVRPGTFVKISCKASGYTFTNYDINWVNQRP
GQGLEWIGWIYPGDGSTKYNEKFKAKATLTADKSSSTAYLQLNNLTSENSAVYFCASGYED
AMDYWGQGTSVTVSSGGGGSGGGGSGGGGSDIKMTQSPSSMYASLGERVIINCKASQDI
NSYLSWFQQKPGKSPKTLIYRANRLVDGVPSRFSGSGSGQDYSLTISSLEYEDMGIYYCLQ
YDEFPLTFGAGTKLELKREPKSPDKTHTCPPCPAPPVAGPSVFLFPPKPKDTLMIARTPEVT
CVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSL
SLSPGKIYIWAPLAGTCGVLLLSLVITLYCKRGRKKLLYIFKQPFMRPVQTTQEEDGCSCRFP
EEEEGGCELRVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDTYDALHMQALP
PR m2H12-6
                                        (SEQ ID NO. 1 + SEQ ID NO. 30)
MALPVTALLLPLALLLHAARPQVQLQQSGPELVRPGTFVKISCKASGYTFTNYDINWVNQRP
GQGLEWIGWIYPGDGSTKYNEKFKAKATLTADKSSSTAYLQLNNLTSENSAVYFCASGYED
AMDYWGQGTSVTVSSGGGGSGGGGSGGGGSDIKMTQSPSSMYASLGERVIINCKASQDI
NSYLSWFQQKPGKSPKTLIYRANRLVDGVPSRFSGSGSGQDYSLTISSLEYEDMGIYYCLQ
YDEFPLTFGAGTKLELKREPKSPDKTHTCPPCPAPPVAGPSVFLFPPKPKDTLMIARTPEVT
CVVVDVSHEDPEVKKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSL
SLSPGKIISFFLSLTSTALLFLLFFLTLRFSVVKRGRKKLLYIFKQPFMRPVQTTQEEDGCSCR
FPEEEEGGCELRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQ
ALPPR

DRB2-1
                                        (SEQ ID NO. 1 + SEQ ID NO. 31)
MALPVTALLLPLALLLHAARPEVKLQESGPELVKPGASVKMSCKASGYKFTDYVVHWLKQK
PGQGLEWIGYINPYNDGTKYNEKFKGKATLTSDKSSSTAYMEVSSLTSEDSAVYYCARDYR
```

YEVYGMDYWGQGTSVTVSSGGGGSGGGGSGGGGSDIVLTQSPTIMSASPGERVTMTCT
ASSSVNIYHWYQQKSGDSPLRWIFDTSKVASGVPARFSGSGSGTSYSLTISTMEAEDAATY
YCQQWRSYPLTFGDGTRLELKRADAAPTVSGLAVSTISSFFPPGYQIYIWAPLAGTCGVLLL
SLVITLYCKRGRKKLLYIFKQPFMRPVQTTQEEDGCSCRFPEEEEGGCELRVKFSRSADAP
AYQQGQNQLYNELNLGRREEYDVLDKRRGRDPEMGGKPRRKNPQEGLYNELQKDKMAE
AYSEIGMKGERRRGKHDGLYQGLSTATKDTYDALHMQALPPR

DRB2-2
                                                       (SEQ ID NO. 1 + SEQ ID NO. 32)
MALPVTALLLPLALLLHAARPEVKLQESGPELVKPGASVKMSCKASGYKFTDYVVHWLKQK
PGQGLEWIGYINPYNDGTKYNEKFKGKATLTSDKSSSTAYMEVSSLTSEDSAVYYCARDYR
YEVYGMDYWGQGTSVTVSSGGGGSGGGGSGGGGSDIVLTQSPTIMSASPGERVTMTCT
ASSSVNIYHWYQQKSGDSPLRWIFDTSKVASGVPARFSGSGSGTSYSLTISTMEAEDAATY
YCQQWRSYPLTFGDGTRLELKRADAAPTVSGLAVSTISSFFPPGYQIISFFLALTSTALLFLLF
FLTLRFSVVKRGRKKLLYIFKQPFMRPVQTTQEEDGCSCRFPEEEEGGCELRVKFSRSADA
PAYQQGQNQLYNELNLGRREEYDVLDKRRGRDPEMGGKPRRKNPQEGLYNELQKDKMA
EAYSEIGMKGERRRGKHDGLYQGLSTATKDTYDALHMQALPPR

DRB2-3
                                                       (SEQ ID NO. 1 + SEQ ID NO. 33)
MALPVTALLLPLALLLHAARPEVKLQESGPELVKPGASVKMSCKASGYKFTDYVVHWLKQK
PGQGLEWIGYINPYNDGTKYNEKFKGKATLTSDKSSSTAYMEVSSLTSEDSAVYYCARDYR
YEVYGMDYWGQGTSVTVSSGGGGSGGGGSGGGGSDIVLTQSPTIMSASPGERVTMTCT
ASSSVNIYHWYQQKSGDSPLRWIFDTSKVASGVPARFSGSGSGTSYSLTISTMEAEDAATY
YCQQWRSYPLTFGDGTRLELKRADAAPTVSTTTPAPRPPTPAPTIASQPLSLRPEACRPAA
GGAVHTRGLDFACDIYIWAPLAGTCGVLLLSLVITLYCKRGRKKLLYIFKQPFMRPVQTTQEE
DGCSCRFPEEEEGGCELRVKFSRSDADAPAYQQGQNQLYNELNLGRREEYDVLDKRRGRD
PEMGGKPRRKNPQEGLYNELQKDKMAEAYSEIGMKGERRRGKHDLYYQGLSTATKDTY
DALHMQALPPR

DRB2-4
                                                       (SEQ ID NO. 1 + SEQ ID NO. 34)
MALPVTALLLPLALLLHAARPEVKLQESGPELVKPGASVKMSCKASGYKFTDYVVHWLKQK
PGQGLEWIGYINPYNDGTKYNEKFKGKATLTSDKSSSTAYMEVSSLTSEDSAVYYCARDYR
YEVYGMDYWGQGTSVTVSSGGGGSGGGGSGGGGSDIVLTQSPTIMSASPGERVTMTCT
ASSSVNIYHWYQQKSGDSPLRWIFDTSKVASGVPARFSGSGSGTSYSLTISTMEAEDAATY
YCQQWRSYPLTFGDGTRLELKRADAAPTVSTTTPAPRPPTPAPTIASQPLSLRPEACRPAA
GGAVHTRGLDFACDIISFFLALTSTALLFLLFFLTLRFSVVKRGRKKLLYIFKQPFMRPVQTTQ
EEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKHDGLYQGLSTATKD
TYDALHMQALPPR

DRB2-5
                                                       (SEQ ID NO. 1 + SEQ ID NO. 35)
MALPVTALLLPLALLLHAARPEVKLQESGPELVKPGASVKMSCKASGYKFTDYVVHWLKQK
PGQGLEWIGYINPYNDGTKYNEKFKGKATLTSDKSSSTAYMEVSSLTSEDSAVYYCARDYR
YEVYGMDYWGQGTSVTVSSGGGGSGGGGSGGGGSDIVLTQSPTIMSASPGERVTMTCT
ASSSVNIYHWYQQKSGDSPLRWIFDTSKVASGVPARFSGSGSGTSYSLTISTMEAEDAATY
YCQQWRSYPLTFGDGTRLELKRADAAPTVSEPKSPDKTHTCPPCPAPPVAGPSVFLFPPK
PKDTLMIARTPEVTCVVVDVSHEDPEVKFNWYVDGVEVHNAKTKPREEQYNSTYRVVSVLT

```
VLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMH

EALHNHYTQKSLSLSPGKIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKHDGLYQGLSTATK

DTYDALHMQALPPR

DRB2-6
                                         (SEQ ID NO. 1 + SEQ ID NO. 36)
MALPVTALLLPLALLLHAARP EVKLQESGPELVKPGASVKMSCKASGYKFTDYVVHWLKQK

PGQGLEWIGYINPYNDGTKYNEKFKGKATLTSDKSSSTAYMEVSSLTSEDSAVYYCARDYR

YEVYGMDYWGQGTSVTVSS GGGGSGGGGSGGGGS DIVLTQSPTIMSASPGERVTMTCT

ASSSVNIYHWYQQKSGDSPLRWIFDTSKVASGVPARFSGSGSGTSYSLTISTMEAEDAATY

YCQQWRSYPLTFGDGTRLELKRADAAPTVS EPKSPDKTHTCPPCPAPPVAGPSVFLFPPK

PKDTLMIARTPEVTCVVVDVSHEDPEVKFMWYVDGVEVHNAKTKPREEQYNSTYRVVSVLT

VLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMH

EALHNHYTQKSLSLSPGKIISFFLALTSTALLFLLFFLTLRFSVVKRGRKKLLYIFKQPFMRPVQ

TTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKHDGLYQGLSTA

TKDTYDALHMQALPPR

My9.6-1
                                         (SEQ ID NO. 1 + SEQ ID NO. 37)
MALPVTALLLPLALLLHAARP QVQLQQPGAEVVKPGASVKMSCKASGYTFTSYYIHWIKQTP

GQGLEWVGVIYPGNDDISYNQKFKGKATLTADKSSTAYMQLSSLTSEDSAVYYCAREVRL

RYFDVWGAGTTVTVSS GGGGSGGGGSGGGGS NIMLTQSPSSLAVSAGEKVTMSCKSSQ

SVFFSSSQKNYLAWYQQIPGQSPKLLIYWASTRESGVPDRFTGSGSGTDFTLTISSVQSEDL

AIYYCHQYLSSRTFGGGTKLEIKR GLAVSTISSFFPPGYQIYIWAPLAGTCGVLLLSLVITLYC

KRGRKKLLYIFKQPFMRPVQTTQEEDGCSCRFPEEEEGGCELRVKFSRSADAPAYQQGQN

QLYNELNLGRREEYDVLDKRRGRDPEMGGKPRRKNPQEGLYNELQKDKMAEAYSEIGMK

GERRRGKHDGLYQGLSTATKDTYDALHMQALPPR

My9.6-2
                                         (SEQ ID NO. 1 + SEQ ID NO. 38)
MALPVTALLLPLALLLHAARP QVQLQQPGAEVVKPGASVKMSCKASGYTFTSYYIHWIKQTP

GQGLEWVGVIYPGNDDISYNQKFKGKATLTADKSSTAYMQLSSLTSEDSAVYYCAREVRL

RYFDVWGAGTTVTVSS GGGGSGGGGSGGGGS NIMLTQSPSSLAVSAGEKVTMSCKSSQ

SVFFSSSQKNYLAWYQQIPGQSPKLLIYWASTRESGVPDRFTGSGSGTDFTLTISSVQSEDL

AIYYCHQYLSSRTFGGGTKLEIKR GLAVSTISSFFPPGYQIISFFLALTSTALLFLLFFLTLRFSV

VKRGRKKLLYIFKQPFMRPVQTTQEEDGCSCRFPEEEEGGCELRVKFSRSADAPAYQQGQ

MQLYNELNLGRREETDVLDKRRGRDPEMGGKPRRKNPQEGLYNELQKDKMAEAYSEIGM

KGERRRGKHDGLYQGLSTATKDTYDALHMQALPPR

My9.6-3
                                         (SEQ ID NO. 1 + SEQ ID NO. 39)
MALPVTALLLPLALLLHAARP QVQLQQPGAEVVKPGASVKMSCKASGYTFTSYYIHWIKQTP

GQGLEWVGVIYPGNDDISYNQKFKGKATLTADKSSTAYMQLSSLTSEDSAVYYCAREVRL
```

-continued

RYFDVWGAGTTVTVSSGGGGSGGGGSGGGGSNIMLTQSPSSLAVSAGEKVTMSCKSSQ
SVFFSSSQKNYLAWYQQIPGQSPKLLIYWASTRESGVPDRFTGSGSGTDFTLTISSVQSEDL
AIYYCHQYLSSRTFGGGTKLEIKRTTTPAPRPPTPAPTIASQPLSLRPEACRPAAGGAVHTR
GLDFACDIYIWAPLAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKDTYDALHMQA
LPPR

My9.6-4
(SEQ ID NO. 1 + SEQ ID NO. 40)
MALPVTALLLPLALLLHAARPQVQLQQPGAEVVKPGASVKMSCKASGYTFTSYYIHWIKQTP
GQGLEWVGVIYPGNDDISYNQKFKGKATLTADKSSTAYMQLSSLTSEDSAVYYCAREVRL
RYFDVWGAGTTVTVSSGGGGSGGGGSGGGGSNIMLTQSPSSLAVSAGEKVTMSCKSSQ
SVFFSSSQKNYLAWYQQIPGQSPKLLIYWASTRESGVPDRFTGSGSGTDFTLTISSVQSEDL
AIYYCHQYLSSRTFGGGTKLEIKRTTTPAPRPPTPAPTIASQPLSLRPEACRPAAGGAVHTR
GLDFACDIISFFLALTSTALLFLLFFLTLRFSVVKRGRKKLLYIFKQPFMRPVQTTQEEDGCSC
RFPEEEEGGCELRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHM
QALPPR

My9.6-5
(SEQ ID NO. 1 + SEQ ID NO. 41)
MALPVTALLLPLALLLHAARPQVQLQQPGAEVVKPGASVKMSCKASGYTFTSYYIHWIKQTP
GQGLEWVGVIYPGNDDISYNQKFKGKATLTADKSSTAYMQLSSLTSEDSAVYYCAREVRL
RYFDVWGAGTTVTVSSGGGGSGGGGSGGGGSNIMLTQSPSSLAVSAGEKVTMSCKSSQ
SVFFSSSQKNYLAWYQQIPGQSPKLLIYWASTRESGVPDRFTGSGSGTDFTLTISSVQSEDL
AIYYCHQYLSSRTFGGGTKLEIKREPKSPDKTHTCPPCPAPPVAGPSVFLFPPKPKDTLMIA
RTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHY
TQKSLSLSPGKIYIWAPLAGTCGVLLLSLVITLYCKRGRKKLLYIFKQPFMRPVQTTQEEDGC
SCRFPEEEEGGCELRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYDAL
HMQALPPR

My9.6-6
(SEQ ID NO. 1 + SEQ ID NO. 42)
MALPVTALLLPLALLLHAARPQVQLQQPGAEVVKPGASVKMSCKASGYTFTSYYIHWIKQTP
GQGLEWVGVIYPGNDDISYNQKFKGKATLTADKSSTAYMQLSSLTSEDSAVYYCAREVRL
RYFDVWGAGTTVTVSSGGGGSGGGGSGGGGSNIMLTQSPSSLAVSAGEKVTMSCKSSQ
SVFFSSSQKNYLAWYQQIPGQSPKLLIYWASTRESGVPDRFTGSGSGTDFTLTISSVQSEDL
AIYYCHQYLSSRTFGGGTKLEIKREPKSPDKTHTCPPCPAPPVAGPSVFLFPPKPKDTLMIA
RTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHEALHNHY
TQKSLSLSPGKIISFFLALTSRALLFLLFFLTLRFSVVKRGRKKLLYIFKQPFMRPVQTTQEED
GCSCRFPEEEEFFCELRVKFSRSADAPAYQQGQNQLYNELNLGRREEYDVLDKRRGRDP

```
EMGGKPRRKNPQEGLYNELQKDKMAEAYSEIGMKGERRRGKGHDGLYQGLSTATKDTYD

ALHMQALPPR
```

REFERENCES

Arimondo, P. B., C. J. Thomas, et al. (2006). "Exploring the cellular activity of camptothecin-triple-helix-forming oligonucleotide conjugates." *Mol Cell Biol* 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." *Rna* 13(6): 803-10.

Bierer, B. E., G. Hollander, et al. (1993). "Cyclosporin A and FK506: molecular mechanisms of immunosuppression and probes for transplantation biology." *Curr Opin Immunol* 5(5): 763-73.

Boch, J., H. Scholze, et al. (2009). "Breaking the code of DNA binding specificity of TAL-type III effectors." *Science* 326(5959): 1509-12.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Cong, L., F. A. Ran, et al. (2013). "Multiplex genome engineering using CRISPR/Cas systems." *Science* 339(6121): 819-23.

Cros, E. et al. (2004). "Problems related to resistance to cytarabine in acute myeloid leukemia". *Leukemia & Lymphoma*. 45(6):1123-1132.

Deltcheva, E., K. Chylinski, et al. (2011). "CRISPR RNA maturation by trans-encoded small RNA and host factor RNase III." *Nature* 471(7340): 602-7.

Donnelly, M. and G. Elliott (2001). "Nuclear localization and shuttling of herpes simplex virus tegument protein VP13/14." *J Virol* 75(6): 2566-74.

Doronina, V. A., C. Wu, et al. (2008). "Site-specific release of nascent chains from ribosomes at a sense codon." *Mol Cell Biol* 28(13): 4227-39.

Eisenschmidt, K., T. Lanio, et al. (2005). "Developing a programmed restriction endonuclease for highly specific DNA cleavage." *Nucleic Acids Res* 33(22): 7039-47.

Gardin, C. et al. (2007). "Postremission treatment of elderly patients with acute myeloid leukemia in first complete remission after intensive induction chemotherapy:results of the multicenter randomized Acute Leukemia French Association (ALFA) 9803 trial". *Blood*. 109(12):5129-5135.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Henderson, D. J., I. Naya, et al. (1991). "Comparison of the effects of FK-506, cyclosporin A and rapamycin on IL-2 production." *Immunology* 73(3): 316-21.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

June, C. H. et al. (2011). "T Cells with Chimeric Antigen Receptors Have Potent Antitumor Effects and Can Establish Memory in Patients with Advanced Leukemia". *Sci. Transl. Med.* 3(95):ra73.

Kalish, J. M. and P. M. Glazer (2005). "Targeted genome modification via triple helix formation." *Ann NY Acad Sci* 1058: 151-61.

Li, T., S. Huang, et al. (2011). "TAL nucleases (TALNs): hybrid proteins composed of TAL effectors and FokI DNA-cleavage domain." *Nucleic Acids Res* 39(1): 359-72.

Liu, J., M. W. Albers, et al. (1992). "Inhibition of T cell signaling by immunophilin-ligand complexes correlates with loss of calcineurin phosphatase activity." *Biochemistry* 31(16): 3896-901.

Mali, P., L. Yang, et al. (2013). "RNA-guided human genome engineering via Cas9." *Science* 339(6121): 823-6.

Maniecki, M. B. et al., (2011) "Is hepatotoxicity in patients treated with gemtuzumabozogamicin due to specific targeting of hepatocytes ?". *Leukemia Research* e84-e86.

Moscou, M. J. and A. J. Bogdanove (2009). "A simple cipher governs DNA recognition by TAL effectors." *Science* 326(5959): 1501.

Paques, F. and P. Duchateau (2007). "Meganucleases and DNA double-strand break-induced recombination: perspectives for gene therapy." *Curr Gene Ther* 7(1): 49-66.

Park, T. S., S. A. Rosenberg, et al. (2011). "Treating cancer with genetically engineered T cells." *Trends Biotechnol* 29(11): 550-7.

Peipp, M., D. Saul, et al. (2004). "Efficient eukaryotic expression of fluorescent scFv fusion proteins directed against CD antigens for FACS applications." *J Immunol Methods* 285(2): 265-80.

Perrin, A., M. Buckle, et al. (1993). "Asymmetrical recognition and activity of the I-SceI endonuclease on its site and on intron-exon junctions." *Embo J* 12(7): 2939-47.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Introduction of double-strand breaks into the genome of mouse cells by expression of a rare-cutting endonuclease." *Mol Cell Biol* 14(12): 8096-106.

Schwemmlein. M. et al. (2006). "A CD33-specific single-chain immunotoxin mediates potent apoptosis of cultured human myeloid leukaemia cells". *British Journal of Haematology.* 133(2): 141-151

Sorek, R., C. M. Lawrence, et al. (2013). "CRISPR-mediated Adaptive Immune Systems in Bacteria and Archaea." *Annu Rev Biochem.*

Stoddard, B. L. (2005). "Homing endonuclease structure and function." *Q Rev Biophys* 38(1): 49-95.

Vitale, C. et al. (2001). "Surface expression and function of p75/AIRM-1 or CD33 in acute myeloid leukemias: engagement of CD33 induces apoptosis of leukemic cells". *PNAS* 98:5764-5769.

The invention claimed is:

1. A method of treating a pre-malignant condition or cancer expressing CD33, comprising administering to a patient in need thereof a therapeutically effective amount of a pharmaceutical composition comprising an engineered immune cell expressing at the cell surface membrane a CD33 specific Chimeric Antigen Receptor (CAR) comprising: (a) an extracellular ligand binding-domain comprising $V_H$ and $V_L$ from a monoclonal anti-CD33 antibody, (b) a hinge selected from FcγRIIIa hinge, CD8α hinge, or IgG1 hinge, (c) a CD8α transmembrane domain and (d) a cytoplasmic domain comprising a CD3 ζ signaling domain and a co-stimulatory domain from 4-1BB.

2. The method according to claim 1, wherein the pre-malignant condition or malignant cancer is a hematological cancer.

3. A method of impairing a hematologic cancer expressing CD33 comprising contacting a hematologic cancer cell with an engineered immune cell expressing at the cell surface membrane a CD33 specific CAR comprising:
 (a) an extracellular ligand binding-domain comprising $V_H$ and $V_L$ from a monoclonal anti-CD33 antibody,
 (b) a hinge selected from FcγRIIIa hinge, CD8α hinge, or IgG1 hinge,
 (c) a CD8α transmembrane domain and
 (d) a cytoplasmic domain comprising a CD3ζ signaling domain and a co-stimulatory domain from 4-1BB
 in an amount effective to cause impairment of said cancer cell.

4. A method of treating a cancer expressing CD33 in a patient comprising administering said patient a therapeutically effective amount of an immune cell expressing at the cell surface membrane a CD33 specific CAR comprising:
 (a) an extracellular ligand binding-domain comprising $V_H$ and $V_L$ from a monoclonal anti-CD33 antibody,
 (b) a hinge selected from FcγRIIIa hinge, CD8α hinge, or IgG1 hinge,
 (c) a CD8α transmembrane domain and
 (d) a cytoplasmic domain comprising a CD3ζ signaling domain and a co-stimulatory domain from 4-1BB.

5. The method according to claim 4, wherein the cancer is a hematological cancer.

6. The method according to claim 1, wherein the CD33 specific CAR comprises a CD8α hinge and a CD8α transmembrane domain.

7. The method according to claim 3, wherein the CD33 specific CAR comprises a CD8α hinge and a CD8α transmembrane domain.

8. The method according to claim 4, wherein the CD33 specific CAR comprises a CD8α hinge and a CD8α transmembrane domain.

9. The method according to claim 1, wherein the CD33 specific CAR comprises a FcγRIIIa hinge and a CD8α transmembrane domain.

10. The method according to claim 3, wherein the CD33 specific CAR comprises a FcγRIIIα hinge and a CD8α transmembrane domain.

11. The method according to claim 4, wherein the CD33 specific CAR comprises a FcγRIIIα hinge and a CD8α transmembrane domain.

12. The method according to claim 1, wherein the CD33 specific CAR comprises an IgG1 hinge and a CD8α transmembrane domain.

13. The method according to claim 3, wherein the CD33 specific CAR comprises an IgG1 hinge and a CD8α transmembrane domain.

14. The method according to claim 4, wherein the CD33 specific CAR comprises an IgG1 hinge and a CD8α transmembrane domain.

15. The method according to claim 1, wherein the $V_H$ comprises a sequence having at least 80% amino acid sequence identity to SEQ ID NO. 11, SEQ ID NO. 13, SEQ ID NO. 15 or SEQ ID NO. 17; and said VL comprises a sequence having at least 80% amino acid sequence identity to SEQ ID NO. 12, SEQ ID NO. 14, SEQ ID NO. 16 or SEQ ID NO. 18.

16. The method according to claim 3, wherein the $V_H$ comprises a sequence having at least 80% amino acid sequence identity to SEQ ID NO. 11, SEQ ID NO. 13, SEQ ID NO. 15 or SEQ ID NO. 17; and said VL comprises a sequence having at least 80% amino acid sequence identity to SEQ ID NO. 12, SEQ ID NO. 14, SEQ ID NO. 16 or SEQ ID NO. 18.

17. The method according to claim 4, wherein the $V_H$ comprises a sequence having at least 80% amino acid sequence identity to SEQ ID NO. 11, SEQ ID NO. 13, SEQ ID NO. 15 or SEQ ID NO. 17; and said VL comprises a sequence having at least 80% amino acid sequence identity to SEQ ID NO. 12, SEQ ID NO. 14, SEQ ID NO. 16 or SEQ ID NO. 18.

18. The method according to claim 1, wherein the engineered immune cell comprises at least one other CAR having specificity for another target other than CD33.

19. The method according to claim 3, wherein the engineered immune cell comprises at least one other CAR having specificity for another target other than CD33.

20. The method according to claim 4, wherein the engineered immune cell comprises at least one other CAR having specificity for another target other than CD33.

21. The method according to claim 1, wherein the engineered immune cell comprises a functionally inactive T-Cell Receptor (TCR).

22. The method according to claim 3, wherein the engineered immune cell comprises a functionally inactive TCR.

23. The method according to claim 4, wherein the engineered immune cell comprises a functionally inactive TCR.

24. The method according to claim 1, wherein the engineered immune cell lacks the expression of CD33.

25. The method according to claim 3, wherein the engineered immune cell lacks the expression of CD33.

26. The method according to claim 4, wherein the engineered immune cell lacks the expression of CD33.

27. The method according to claim 1, wherein the engineered immune cell is modified to be resistant to at least one immune suppressive or chemotherapy drug.

28. The method according to claim 3, wherein the engineered immune cell is modified to be resistant to at least one immune suppressive or chemotherapy drug.

29. The method according to claim 4, wherein the engineered immune cell is modified to be resistant to at least one immune suppressive or chemotherapy drug.

* * * * *

UNITED STATES PATENT AND TRADEMARK OFFICE
CERTIFICATE OF CORRECTION

PATENT NO.        : 9,944,702 B2
APPLICATION NO.   : 15/301686
DATED             : April 17, 2018
INVENTOR(S)       : Roman Galetto Page 1 of 2

It is certified that error appears in the above-identified patent and that said Letters Patent is hereby corrected as shown below:

In the Specification

In the description:

In Columns 5-6 and continuing on Columns 7-8, Table 3:
"SEQ ID NO. 20" should read --SEQ ID NO. 25--;
"SEQ ID NO. 21" should read --SEQ ID NO. 31--; and
"SEQ ID NO. 22" should read --SEQ ID NO. 37--.

In Columns 7-8, Table 4:
"SEQ ID NO. 23" should read --SEQ ID NO. 20--;
"SEQ ID NO. 24" should read --SEQ ID NO. 26--;
"SEQ ID NO. 25" should read --SEQ ID NO. 32--; and
"SEQ ID NO. 26" should read --SEQ ID NO. 38--.

In Columns 7-8, Table 5:
"SEQ ID NO. 27" should read --SEQ ID NO. 21--;
"SEQ ID NO. 28" should read --SEQ ID NO. 27--;
"SEQ ID NO. 29" should read --SEQ ID NO. 33--;
"SEQ ID NO. 30" should read --SEQ ID NO. 39--;
"CD8? hinge" should read --CD8α hinge--;
"CD8? TM" should read --CD8α TM--; and
"CD3?? CD" should read -- CD3ζ CD--.

In Columns 7-8, Table 6:
"SEQ ID NO. 31" should read --SEQ ID NO. 22--;
"SEQ ID NO. 32" should read --SEQ ID NO. 28--;
"SEQ ID NO. 33" should read --SEQ ID NO. 34--;
"SEQ ID NO. 34" should read --SEQ ID NO. 40--; and
"My9-6-5" should read --My9-6-4--.

Signed and Sealed this
Thirtieth Day of April, 2019

Andrei Iancu
*Director of the United States Patent and Trademark Office*

CERTIFICATE OF CORRECTION (continued)
U.S. Pat. No. 9,944,702 B2

In Columns 9-10, Table 7:
"SEQ ID NO. 35" should read --SEQ ID NO. 23--;
"SEQ ID NO. 36" should read --SEQ ID NO. 29--;
"SEQ ID NO. 37" should read --SEQ ID NO. 35--;
"SEQ ID NO. 38" should read --SEQ ID NO. 41--;
"CD8? TM" should read --CD8α TM--; and
"CD3?? CD" should read --CD3ζ CD--.

In Columns 9-10, Table 8:
"SEQ ID NO. 39" should read --SEQ ID NO. 24--;
"SEQ ID NO. 40" should read --SEQ ID NO. 30--; and
"SEQ ID NO. 41" should read --SEQ ID NO. 36--.

SEQUENCE LISTING

<160> NUMBER OF SEQ ID NOS: 87

<210> SEQ ID NO 1
<211> LENGTH: 20
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: signal peptide

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 21
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: signal peptide

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 16
<212> TYPE: PRT
<213> ORGANISM: homo sapiens
<220> FEATURE:
<223> OTHER INFORMATION: FcgRIIIa hinge

<400> SEQUENCE: 3

Gly Leu Ala Val Ser Thr Ile Ser Ser Phe Phe Pro Pro Gly Tyr Gln
1               5                   10                  15

<210> SEQ ID NO 4
<211> LENGTH: 45
<212> TYPE: PRT
<213> ORGANISM: homo sapiens
<220> FEATURE:

<400> SEQUENCE: 4

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 5
<211> LENGTH: 231
<212> TYPE: PRT
<213> ORGANISM: homo sapiens
<220> FEATURE:
<223> OTHER INFORMATION: IgG1 hinge

<400> SEQUENCE: 5

| | | | | | | | | | | | | | | | |
|---|---|---|---|---|---|---|---|---|---|---|---|---|---|---|---|
| Glu | Pro | Lys | Ser | Pro | Asp | Lys | Thr | His | Thr | Cys | Pro | Pro | Cys | Pro | Ala |
| 1 | | | | 5 | | | | | 10 | | | | | 15 | |
| Pro | Pro | Val | Ala | Gly | Pro | Ser | Val | Phe | Leu | Phe | Pro | Pro | Lys | Pro | Lys |
| | | | 20 | | | | | 25 | | | | | 30 | | |
| Asp | Thr | Leu | Met | Ile | Ala | Arg | Thr | Pro | Glu | Val | Thr | Cys | Val | Val | Val |
| | | | 35 | | | | | 40 | | | | | 45 | | |
| Asp | Val | Ser | His | Glu | Asp | Pro | Glu | Val | Lys | Phe | Asn | Trp | Tyr | Val | Asp |
| | | 50 | | | | | 55 | | | | | 60 | | | |
| Gly | Val | Glu | Val | His | Asn | Ala | Lys | Thr | Lys | Pro | Arg | Glu | Glu | Gln | Tyr |
| 65 | | | | | 70 | | | | | 75 | | | | | 80 |
| Asn | Ser | Thr | Tyr | Arg | Val | Val | Ser | Val | Leu | Thr | Val | Leu | His | Gln | Asp |
| | | | | 85 | | | | | 90 | | | | | 95 | |
| Trp | Leu | Asn | Gly | Lys | Glu | Tyr | Lys | Cys | Lys | Val | Ser | Asn | Lys | Ala | Leu |
| | | | | 100 | | | | | 105 | | | | | 110 | |
| Pro | Ala | Pro | Ile | Glu | Lys | Thr | Ile | Ser | Lys | Ala | Lys | Gly | Gln | Pro | Arg |
| | | | 115 | | | | | 120 | | | | | 125 | | |
| Glu | Pro | Gln | Val | Tyr | Thr | Leu | Pro | Pro | Ser | Arg | Asp | Glu | Leu | Thr | Lys |
| | | | 130 | | | | | 135 | | | | | 140 | | |
| Asn | Gln | Val | Ser | Leu | Thr | Cys | Leu | Val | Lys | Gly | Phe | Tyr | Pro | Ser | Asp |
| 145 | | | | | 150 | | | | | 155 | | | | | 160 |
| Ile | Ala | Val | Glu | Trp | Glu | Ser | Asn | Gly | Gln | Pro | Glu | Asn | Asn | Tyr | Lys |
| | | | | 165 | | | | | 170 | | | | | 175 | |
| Thr | Thr | Pro | Pro | Val | Leu | Asp | Ser | Asp | Gly | Ser | Phe | Phe | Leu | Tyr | Ser |
| | | | 180 | | | | | 185 | | | | | 190 | | |
| Lys | Leu | Thr | Val | Asp | Lys | Ser | Arg | Trp | Gln | Gln | Gly | Asn | Val | Phe | Ser |
| | | | 195 | | | | | 200 | | | | | 205 | | |
| Cys | Ser | Val | Met | His | Glu | Ala | Leu | His | Asn | His | Tyr | Thr | Gln | Lys | Ser |
| | | | 210 | | | | | 215 | | | | | 220 | | |
| Leu | Ser | Leu | Ser | Pro | Gly | Lys | | | | | | | | | |
| 225 | | | | | 230 | | | | | | | | | | |

<210> SEQ ID NO 6
<211> LENGTH: 24
<212> TYPE: PRT
<213> ORGANISM: homo sapiens
<220> FEATURE:
<223> OTHER INFORMATION: CD8alpha transmembrane domain

<400> SEQUENCE: 6

| | | | | | | | | | | | | | | | |
|---|---|---|---|---|---|---|---|---|---|---|---|---|---|---|---|
| Ile | Tyr | Ile | Trp | Ala | Pro | Leu | Ala | Gly | Thr | Cys | Gly | Val | Leu | Leu | Leu |
| 1 | | | | 5 | | | | | 10 | | | | | 15 | |
| Ser | Leu | Val | Ile | Thr | Leu | Tyr | Cys | | | | | | | | |
| | | | 20 | | | | | | | | | | | | |

<210> SEQ ID NO 7
<211> LENGTH: 27
<212> TYPE: PRT
<213> ORGANISM: homo sapiens
<220> FEATURE:
<223> OTHER INFORMATION: 41BB transmembrane domain

<400> SEQUENCE: 7

| | | | | | | | | | | | | | | | |
|---|---|---|---|---|---|---|---|---|---|---|---|---|---|---|---|
| Ile | Ile | Ser | Phe | Phe | Leu | Ala | Leu | Thr | Ser | Thr | Ala | Leu | Leu | Phe | Leu |
| 1 | | | | 5 | | | | | 10 | | | | | 15 | |
| Leu | Phe | Phe | Leu | Thr | Leu | Arg | Phe | Ser | Val | Val | | | | | |
| | | | 20 | | | | | 25 | | | | | | | |

<210> SEQ ID NO 8
<211> LENGTH: 42
<212> TYPE: PRT
<213> ORGANISM: homo sapiens
<220> FEATURE:
<223> OTHER INFORMATION: Fragment of 4-1BB (residues 214-255)

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 112
<212> TYPE: PRT
<213> ORGANISM: homo sapiens
<220> FEATURE:
<223> OTHER INFORMATION: fragment of T-cell surface glycoprotein CD3
      zeta chain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 15
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: linker

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 115
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195 heavy chain variable region

<400> SEQUENCE: 11

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110

Thr Val Ser
        115

<210> SEQ ID NO 12
<211> LENGTH: 111
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195 light chain variable region

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110

<210> SEQ ID NO 13
<211> LENGTH: 117
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12 heavy chain variable region

<400> SEQUENCE: 13

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile

```
                35                  40                  45

Gly Trp Ile Tyr Pro Gly Asp Gly Ser Thr Lys Tyr Asn Glu Lys Phe
 50                  55                  60

Lys Ala Lys Ala Thr Leu Thr Ala Asp Lys Ser Ser Thr Ala Tyr
 65                  70                  75                  80

Leu Gln Leu Asn Asn Leu Thr Ser Glu Asn Ser Ala Val Tyr Phe Cys
                 85                  90                  95

Ala Ser Gly Tyr Glu Asp Ala Met Asp Tyr Trp Gly Gln Gly Thr Ser
            100                 105                 110

Val Thr Val Ser Ser
        115

<210> SEQ ID NO 14
<211> LENGTH: 108
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12 light chain variable region

<400> SEQUENCE: 14

Asp Ile Lys Met Thr Gln Ser Pro Ser Ser Met Tyr Ala Ser Leu Gly
 1               5                  10                  15

Glu Arg Val Ile Ile Asn Cys Lys Ala Ser Gln Asp Ile Asn Ser Tyr
                20                  25                  30

Leu Ser Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Leu
                 85                  90                  95

Thr Phe Gly Ala Gly Thr Lys Leu Glu Leu Lys Arg
            100                 105

<210> SEQ ID NO 15
<211> LENGTH: 120
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2 heavy chain variable region

<400> SEQUENCE: 15

Glu Val Lys Leu Gln Glu Ser Gly Pro Glu Leu Val Lys Pro Gly Ala
 1               5                  10                  15

Ser Val Lys Met Ser Cys Lys Ala Ser Gly Tyr Lys Phe Thr Asp Tyr
                20                  25                  30

Val Val His Trp Leu Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Lys Ser Ser Ser Thr Ala Tyr
 65                  70                  75                  80
```

```
Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser
        115                 120

<210> SEQ ID NO 16
<211> LENGTH: 115
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2 light chain variable region

<400> SEQUENCE: 16

Asp Ile Val Leu Thr Gln Ser Pro Thr Ile Met Ser Ala Ser Pro Gly
1               5                   10                  15

Glu Arg Val Thr Met Thr Cys Thr Ala Ser Ser Ser Val Asn Tyr Ile
            20                  25                  30

His Trp Tyr Gln Gln Lys Ser Gly Asp Ser Pro Leu Arg Trp Ile Phe
        35                  40                  45

Asp Thr Ser Lys Val Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Arg Ser Tyr Pro Leu Thr
                85                  90                  95

Phe Gly Asp Gly Thr Arg Leu Glu Leu Lys Arg Ala Asp Ala Ala Pro
            100                 105                 110

Thr Val Ser
        115

<210> SEQ ID NO 17
<211> LENGTH: 118
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6 heavy chain variable region

<400> SEQUENCE: 17

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110
```

Thr Val Thr Val Ser Ser
        115

<210> SEQ ID NO 18
<211> LENGTH: 113
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6 light chain variable region

<400> SEQUENCE: 18

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
            100                 105                 110

Arg

<210> SEQ ID NO 19
<211> LENGTH: 436
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-1 polypeptide CAR sequence

<400> SEQUENCE: 19

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110

Thr Val Ser Ser Gly Gly Gly Gly Ser Gly Gly Gly Gly Ser Gly Gly
        115                 120                 125

Gly Gly Ser Asp Ile Val Leu Thr Gln Ser Pro Ala Ser Leu Ala Val
    130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
            165                 170                 175

Gln Pro Pro Lys Leu Leu Ile Tyr Ala Ala Ser Asn Gln Gly Ser Gly
        180                 185                 190

Val Pro Ala Arg Phe Ser Gly Ser Gly Ser Gly Thr Asp Phe Ser Leu
    195                 200                 205

Asn Ile His Pro Met Glu Glu Asp Thr Ala Met Tyr Phe Cys Gln
210                 215                 220

Gln Ser Lys Glu Val Pro Trp Thr Phe Gly Gly Gly Thr Lys Leu Glu
225                 230                 235                 240

Ile Lys Gly Leu Ala Val Ser Thr Ile Ser Ser Phe Phe Pro Pro Gly
            245                 250                 255

Tyr Gln Ile Tyr Ile Trp Ala Pro Leu Ala Gly Thr Cys Gly Val Leu
        260                 265                 270

Leu Leu Ser Leu Val Ile Thr Leu Tyr Cys Lys Arg Gly Arg Lys Lys
    275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
            325                 330                 335

Tyr Gln Gln Gly Gln Asn Gln Leu Tyr Asn Glu Leu Asn Leu Gly Arg
        340                 345                 350

Arg Glu Glu Tyr Asp Val Leu Asp Lys Arg Arg Gly Arg Asp Pro Glu
    355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
        420                 425                 430

Leu Pro Pro Arg
        435

<210> SEQ ID NO 20
<211> LENGTH: 439
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-2 polypeptide CAR sequence

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

-continued

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Thr Ala Tyr
65                  70                  75                  80

Met Asp Val Arg Ser Leu Thr Ser Glu Asp Ser Ala Val Tyr Tyr Cys
                        85                  90                  95

Ala Arg Gly Arg Pro Ala Met Asp Tyr Trp Gly Gln Gly Thr Ser Val
                100                 105                 110

Thr Val Ser Ser Gly Gly Gly Ser Gly Gly Gly Ser Gly Gly
            115                 120                 125

Gly Gly Ser Asp Ile Val Leu Thr Gln Ser Pro Ala Ser Leu Ala Val
        130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
                180                 185                 190

Val Pro Ala Arg Phe Ser Gly Ser Gly Thr Asp Phe Ser Leu
            195                 200                 205

Asn Ile His Pro Met Glu Glu Asp Thr Ala Met Tyr Phe Cys Gln
    210                 215                 220

Gln Ser Lys Glu Val Pro Trp Thr Phe Gly Gly Gly Thr Lys Leu Glu
225                 230                 235                 240

Ile Lys Gly Leu Ala Val Ser Thr Ile Ser Ser Phe Phe Pro Pro Gly
                245                 250                 255

Tyr Gln Ile Ile Ser Phe Phe Leu Ala Leu Thr Ser Thr Ala Leu Leu
            260                 265                 270

Phe Leu Leu Phe Phe Leu Thr Leu Arg Phe Ser Val Val Lys Arg Gly
        275                 280                 285

Arg Lys Lys Leu Leu Tyr Ile Phe Lys Gln Pro Phe Met Arg Pro Val
    290                 295                 300

Gln Thr Thr Gln Glu Glu Asp Gly Cys Ser Cys Arg Phe Pro Glu Glu
305                 310                 315                 320

Glu Glu Gly Gly Cys Glu Leu Arg Val Lys Phe Ser Arg Ser Ala Asp
                325                 330                 335

Ala Pro Ala Tyr Gln Gln Gly Gln Asn Gln Leu Tyr Asn Glu Leu Asn
            340                 345                 350

Leu Gly Arg Arg Glu Glu Tyr Asp Val Leu Asp Lys Arg Arg Gly Arg
        355                 360                 365

Asp Pro Glu Met Gly Gly Lys Pro Arg Arg Lys Asn Pro Gln Glu Gly
    370                 375                 380

Leu Tyr Asn Glu Leu Gln Lys Asp Lys Met Ala Glu Ala Tyr Ser Glu
385                 390                 395                 400

Ile Gly Met Lys Gly Glu Arg Arg Gly Lys Gly His Asp Gly Leu
                405                 410                 415

Tyr Gln Gly Leu Ser Thr Ala Thr Lys Asp Thr Tyr Asp Ala Leu His
            420                 425                 430

Met Gln Ala Leu Pro Pro Arg
        435

<210> SEQ ID NO 21
<211> LENGTH: 465

```
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-3 polypeptide CAR sequence

<400> SEQUENCE: 21
```

| | | | | | | | | | | | | | | |
|---|---|---|---|---|---|---|---|---|---|---|---|---|---|---|
| Glu | Val | Gln | Leu | Gln | Gln | Ser | Gly | Pro | Glu | Leu | Val | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asp | Tyr |
| | | | 20 | | | | | 25 | | | | | 30 | | |
| Asn | Met | His | Trp | Val | Lys | Gln | Ser | His | Gly | Lys | Ser | Leu | Glu | Trp | Ile |
| | | 35 | | | | | 40 | | | | | 45 | | | |
| Gly | Tyr | Ile | Tyr | Pro | Tyr | Asn | Gly | Gly | Thr | Gly | Tyr | Asn | Gln | Lys | Phe |
| | 50 | | | | | 55 | | | | | 60 | | | | |
| Lys | Ser | Lys | Ala | Thr | Leu | Thr | Val | Asp | Asn | Ser | Ser | Thr | Ala | Tyr |
| 65 | | | | | 70 | | | | | 75 | | | | | 80 |
| Met | Asp | Val | Arg | Ser | Leu | Thr | Ser | Glu | Asp | Ser | Ala | Val | Tyr | Tyr | Cys |
| | | | | 85 | | | | | 90 | | | | | 95 | |
| Ala | Arg | Gly | Arg | Pro | Ala | Met | Asp | Tyr | Trp | Gly | Gln | Gly | Thr | Ser | Val |
| | | | 100 | | | | | 105 | | | | | 110 | | |
| Thr | Val | Ser | Ser | Gly | Gly | Gly | Gly | Ser | Gly | Gly | Gly | Gly | Ser | Gly | Gly |
| | | 115 | | | | | 120 | | | | | 125 | | | |
| Gly | Gly | Ser | Asp | Ile | Val | Leu | Thr | Gln | Ser | Pro | Ala | Ser | Leu | Ala | Val |
| | 130 | | | | | 135 | | | | | 140 | | | | |
| Ser | Leu | Gly | Gln | Arg | Ala | Thr | Ile | Ser | Cys | Arg | Ala | Ser | Glu | Ser | Val |
| 145 | | | | | 150 | | | | | 155 | | | | | 160 |
| Asp | Asn | Tyr | Gly | Ile | Ser | Phe | Met | Asn | Trp | Phe | Gln | Gln | Lys | Pro | Gly |
| | | | | 165 | | | | | 170 | | | | | 175 | |
| Gln | Pro | Pro | Lys | Leu | Leu | Ile | Tyr | Ala | Ala | Ser | Asn | Gln | Gly | Ser | Gly |
| | | | 180 | | | | | 185 | | | | | 190 | | |
| Val | Pro | Ala | Arg | Phe | Ser | Gly | Ser | Gly | Ser | Gly | Thr | Asp | Phe | Ser | Leu |
| | | 195 | | | | | 200 | | | | | 205 | | | |
| Asn | Ile | His | Pro | Met | Glu | Glu | Asp | Asp | Thr | Ala | Met | Tyr | Phe | Cys | Gln |
| | 210 | | | | | 215 | | | | | 220 | | | | |
| Gln | Ser | Lys | Glu | Val | Pro | Trp | Thr | Phe | Gly | Gly | Gly | Thr | Lys | Leu | Glu |
| 225 | | | | | 230 | | | | | 235 | | | | | 240 |
| Ile | Lys | Thr | Thr | Thr | Pro | Ala | Pro | Arg | Pro | Pro | Thr | Pro | Ala | Pro | Thr |
| | | | | 245 | | | | | 250 | | | | | 255 | |
| Ile | Ala | Ser | Gln | Pro | Leu | Ser | Leu | Arg | Pro | Glu | Ala | Cys | Arg | Pro | Ala |
| | | | 260 | | | | | 265 | | | | | 270 | | |
| Ala | Gly | Gly | Ala | Val | His | Thr | Arg | Gly | Leu | Asp | Phe | Ala | Cys | Asp | Ile |
| | | 275 | | | | | 280 | | | | | 285 | | | |
| Tyr | Ile | Trp | Ala | Pro | Leu | Ala | Gly | Thr | Cys | Gly | Val | Leu | Leu | Leu | Ser |
| | 290 | | | | | 295 | | | | | 300 | | | | |
| Leu | Val | Ile | Thr | Leu | Tyr | Cys | Lys | Arg | Gly | Arg | Lys | Lys | Leu | Leu | Tyr |
| 305 | | | | | 310 | | | | | 315 | | | | | 320 |
| Ile | Phe | Lys | Gln | Pro | Phe | Met | Arg | Pro | Val | Gln | Thr | Thr | Gln | Glu | Glu |
| | | | | 325 | | | | | 330 | | | | | 335 | |
| Asp | Gly | Cys | Ser | Cys | Arg | Phe | Pro | Glu | Glu | Glu | Glu | Gly | Gly | Cys | Glu |
| | | | 340 | | | | | 345 | | | | | 350 | | |
| Leu | Arg | Val | Lys | Phe | Ser | Arg | Ser | Ala | Asp | Ala | Pro | Ala | Tyr | Gln | Gln |
| | | 355 | | | | | 360 | | | | | 365 | | | |

Gly Gln Asn Gln Leu Tyr Asn Glu Leu Asn Leu Gly Arg Arg Glu Glu
370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
                420                 425                 430

Arg Arg Arg Gly Lys Gly His Asp Gly Leu Tyr Gln Gly Leu Ser Thr
                435                 440                 445

Ala Thr Lys Asp Thr Tyr Asp Ala Leu His Met Gln Ala Leu Pro Pro
450                 455                 460

Arg
465

<210> SEQ ID NO 22
<211> LENGTH: 468
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-4 polypeptide CAR sequence

<400> SEQUENCE: 22

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Leu Thr Val Asp Asn Ser Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
                100                 105                 110

Thr Val Ser Ser Gly Gly Gly Ser Gly Gly Gly Ser Gly Gly Gly
            115                 120                 125

Gly Gly Ser Asp Ile Val Leu Thr Gln Ser Pro Ala Ser Leu Ala Val
        130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
                180                 185                 190

Val Pro Ala Arg Phe Ser Gly Ser Gly Ser Gly Thr Asp Phe Ser Leu
                195                 200                 205

Asn Ile His Pro Met Glu Glu Asp Asp Thr Ala Met Tyr Phe Cys Gln
            210                 215                 220

Gln Ser Lys Glu Val Pro Trp Thr Phe Gly Gly Gly Thr Lys Leu Glu
225                 230                 235                 240

```
Ile Lys Thr Thr Thr Pro Ala Pro Arg Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Ile Ser Phe Phe Leu Ala Leu Thr Ser Thr Ala Leu Leu Phe Leu Leu
    290                 295                 300

Phe Phe Leu Thr Leu Arg Phe Ser Val Val Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 23
<211> LENGTH: 651
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-5 polypeptide CAR sequence

<400> SEQUENCE: 23

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Leu Thr Val Asp Asn Ser Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
            100                 105                 110
```

```
Thr Val Ser Ser Gly Gly Gly Ser Gly Gly Gly Ser Gly Gly
            115                 120                 125

Gly Gly Ser Asp Ile Val Leu Thr Gln Ser Pro Ala Ser Leu Ala Val
130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
            180                 185                 190

Val Pro Ala Arg Phe Ser Gly Ser Gly Ser Gly Thr Asp Phe Ser Leu
            195                 200                 205

Asn Ile His Pro Met Glu Glu Asp Asp Thr Ala Met Tyr Phe Cys Gln
            210                 215                 220

Gln Ser Lys Glu Val Pro Trp Thr Phe Gly Gly Gly Thr Lys Leu Glu
225                 230                 235                 240

Ile Lys Glu Pro Lys Ser Pro Asp Lys Thr His Thr Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ala Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
450                 455                 460

Lys Ser Leu Ser Leu Ser Pro Gly Lys Ile Tyr Ile Trp Ala Pro Leu
465                 470                 475                 480

Ala Gly Thr Cys Gly Val Leu Leu Leu Ser Leu Val Ile Thr Leu Tyr
                485                 490                 495

Cys Lys Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
            515                 520                 525

Phe Pro Glu Glu Glu Glu Gly Gly Cys Glu Leu Arg Val Lys Phe Ser
```

```
                  530             535             540
Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
                565                 570                 575

Arg Arg Gly Arg Asp Pro Glu Met Gly Gly Lys Pro Arg Arg Lys Asn
            580                 585                 590

Pro Gln Glu Gly Leu Tyr Asn Glu Leu Gln Lys Asp Lys Met Ala Glu
                595                 600                 605

Ala Tyr Ser Glu Ile Gly Met Lys Gly Glu Arg Arg Arg Gly Lys Gly
                610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg
                645                 650

<210> SEQ ID NO 24
<211> LENGTH: 654
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: M195-6 polypeptide CAR sequence

<400> SEQUENCE: 24

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Thr Gly Tyr Asn Gln Lys Phe
        50                  55                  60

Lys Ser Lys Ala Thr Leu Thr Val Asp Asn Ser Ser Ser Thr Ala Tyr
65                  70                  75                  80

Met Asp Val Arg Ser Leu Thr Ser Glu Asp Ser Ala Val Tyr Tyr Cys
                85                  90                  95

Ala Arg Gly Arg Pro Ala Met Asp Tyr Trp Gly Gln Gly Thr Ser Val
                100                 105                 110

Thr Val Ser Ser Gly Gly Gly Gly Ser Gly Gly Gly Gly Ser Gly Gly
            115                 120                 125

Gly Gly Ser Asp Ile Val Leu Thr Gln Ser Pro Ala Ser Leu Ala Val
        130                 135                 140

Ser Leu Gly Gln Arg Ala Thr Ile Ser Cys Arg Ala Ser Glu Ser Val
145                 150                 155                 160

Asp Asn Tyr Gly Ile Ser Phe Met Asn Trp Phe Gln Gln Lys Pro Gly
                165                 170                 175

Gln Pro Pro Lys Leu Leu Ile Tyr Ala Ala Ser Asn Gln Gly Ser Gly
                180                 185                 190

Val Pro Ala Arg Phe Ser Gly Ser Gly Ser Gly Thr Asp Phe Ser Leu
            195                 200                 205

Asn Ile His Pro Met Glu Glu Asp Asp Thr Ala Met Tyr Phe Cys Gln
        210                 215                 220

Gln Ser Lys Glu Val Pro Trp Thr Phe Gly Gly Gly Thr Lys Leu Glu
```

-continued

```
            225                 230                 235                 240
        Ile Lys Glu Pro Lys Ser Pro Asp Lys Thr His Thr Cys Pro Pro Cys
                        245                 250                 255

Pro Ala Pro Pro Val Ala Gly Pro Ser Val Phe Leu Phe Pro Pro Lys
                        260                 265                 270

Pro Lys Asp Thr Leu Met Ile Ala Arg Thr Pro Glu Val Thr Cys Val
                    275                 280                 285

Val Val Asp Val Ser His Glu Asp Pro Glu Val Lys Phe Asn Trp Tyr
                290                 295                 300

Val Asp Gly Val Glu Val His Asn Ala Lys Thr Lys Pro Arg Glu Glu
        305                 310                 315                 320

Gln Tyr Asn Ser Thr Tyr Arg Val Val Ser Val Leu Thr Val Leu His
                        325                 330                 335

Gln Asp Trp Leu Asn Gly Lys Glu Tyr Lys Cys Lys Val Ser Asn Lys
                        340                 345                 350

Ala Leu Pro Ala Pro Ile Glu Lys Thr Ile Ser Lys Ala Lys Gly Gln
                    355                 360                 365

Pro Arg Glu Pro Gln Val Tyr Thr Leu Pro Pro Ser Arg Asp Glu Leu
                370                 375                 380

Thr Lys Asn Gln Val Ser Leu Thr Cys Leu Val Lys Gly Phe Tyr Pro
        385                 390                 395                 400

Ser Asp Ile Ala Val Glu Trp Glu Ser Asn Gly Gln Pro Glu Asn Asn
                        405                 410                 415

Tyr Lys Thr Thr Pro Pro Val Leu Asp Ser Asp Gly Ser Phe Phe Leu
                        420                 425                 430

Tyr Ser Lys Leu Thr Val Asp Lys Ser Arg Trp Gln Gln Gly Asn Val
                    435                 440                 445

Phe Ser Cys Ser Val Met His Glu Ala Leu His Asn His Tyr Thr Gln
                450                 455                 460

Lys Ser Leu Ser Leu Ser Pro Gly Lys Ile Ile Ser Phe Phe Leu Ala
        465                 470                 475                 480

Leu Thr Ser Thr Ala Leu Leu Phe Leu Leu Phe Phe Leu Thr Leu Arg
                        485                 490                 495

Phe Ser Val Val Lys Arg Gly Arg Lys Lys Leu Leu Tyr Ile Phe Lys
                        500                 505                 510

Gln Pro Phe Met Arg Pro Val Gln Thr Thr Gln Glu Glu Asp Gly Cys
                    515                 520                 525

Ser Cys Arg Phe Pro Glu Glu Glu Glu Gly Gly Cys Glu Leu Arg Val
                530                 535                 540

Lys Phe Ser Arg Ser Ala Asp Ala Pro Ala Tyr Gln Gln Gly Gln Asn
        545                 550                 555                 560

Gln Leu Tyr Asn Glu Leu Asn Leu Gly Arg Arg Glu Glu Tyr Asp Val
                        565                 570                 575

Leu Asp Lys Arg Arg Gly Arg Asp Pro Glu Met Gly Gly Lys Pro Arg
                        580                 585                 590

Arg Lys Asn Pro Gln Glu Gly Leu Tyr Asn Glu Leu Gln Lys Asp Lys
                    595                 600                 605

Met Ala Glu Ala Tyr Ser Glu Ile Gly Met Lys Gly Glu Arg Arg Arg
                610                 615                 620

Gly Lys Gly His Asp Gly Leu Tyr Gln Gly Leu Ser Thr Ala Thr Lys
        625                 630                 635                 640

Asp Thr Tyr Asp Ala Leu His Met Gln Ala Leu Pro Pro Arg
                        645                 650
```

```
<210> SEQ ID NO 25
<211> LENGTH: 434
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12-1 polypeptide CAR sequence

<400> SEQUENCE: 25

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
                20                  25                  30

Asp Ile Asn Trp Val Asn Gln Arg Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Gly Ser Gly
    115                 120                 125

Gly Gly Gly Ser Asp Ile Lys Met Thr Gln Ser Pro Ser Ser Met Tyr
    130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
    195                 200                 205

Ser Leu Glu Tyr Glu Asp Met Gly Ile Tyr Tyr Cys Leu Gln Tyr Asp
    210                 215                 220

Glu Phe Pro Leu Thr Phe Gly Ala Gly Thr Lys Leu Glu Leu Lys Arg
225                 230                 235                 240

Gly Leu Ala Val Ser Thr Ile Ser Ser Phe Phe Pro Pro Gly Tyr Gln
                245                 250                 255

Ile Tyr Ile Trp Ala Pro Leu Ala Gly Thr Cys Gly Val Leu Leu Leu
            260                 265                 270

Ser Leu Val Ile Thr Leu Tyr Cys Lys Arg Gly Arg Lys Lys Leu Leu
    275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Gly Gly Cys
305                 310                 315                 320

Glu Leu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350
```

```
Glu Tyr Asp Val Leu Asp Lys Arg Arg Gly Arg Asp Pro Glu Met Gly
            355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 26
<211> LENGTH: 437
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12-2 polypeptide CAR sequence

<400> SEQUENCE: 26

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Asp Ile Lys Met Thr Gln Ser Pro Ser Ser Met Tyr
    130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
    210                 215                 220

Glu Phe Pro Leu Thr Phe Gly Ala Gly Thr Lys Leu Glu Leu Lys Arg
225                 230                 235                 240

Gly Leu Ala Val Ser Thr Ile Ser Ser Phe Phe Pro Pro Gly Tyr Gln
                245                 250                 255
```

```
Ile Ile Ser Phe Phe Leu Ala Leu Thr Ser Thr Ala Leu Leu Phe Leu
                260                 265                 270

Leu Phe Phe Leu Thr Leu Arg Phe Ser Val Val Lys Arg Gly Arg Lys
            275                 280                 285

Lys Leu Leu Tyr Ile Phe Lys Gln Pro Phe Met Arg Pro Val Gln Thr
        290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
        435

<210> SEQ ID NO 27
<211> LENGTH: 463
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12-3 polypeptide CAR sequence

<400> SEQUENCE: 27

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Gly Ser Gly Gly Gly Ser Gly
        115                 120                 125

Gly Gly Gly Ser Asp Ile Lys Met Thr Gln Ser Pro Ser Ser Met Tyr
    130                 135                 140

Ala Ser Leu Gly Glu Arg Val Ile Ile Asn Cys Lys Ala Ser Gln Asp
145                 150                 155                 160
```

Ile Asn Ser Tyr Leu Ser Trp Phe Gln Gln Lys Pro Gly Lys Ser Pro
            165                 170                 175

Lys Thr Leu Ile Tyr Arg Ala Asn Arg Leu Val Asp Gly Val Pro Ser
        180                 185                 190

Arg Phe Ser Gly Ser Gly Ser Gly Gln Asp Tyr Ser Leu Thr Ile Ser
            195                 200                 205

Ser Leu Glu Tyr Glu Asp Met Gly Ile Tyr Tyr Cys Leu Gln Tyr Asp
        210                 215                 220

Glu Phe Pro Leu Thr Phe Gly Ala Gly Thr Lys Leu Glu Leu Lys Arg
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
            260                 265                 270

Gly Ala Val His Thr Arg Gly Leu Asp Phe Ala Cys Asp Ile Tyr Ile
        275                 280                 285

Trp Ala Pro Leu Ala Gly Thr Cys Gly Val Leu Leu Leu Ser Leu Val
    290                 295                 300

Ile Thr Leu Tyr Cys Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Arg
            340                 345                 350

Val Lys Phe Ser Arg Ser Ala Asp Ala Pro Ala Tyr Gln Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460

<210> SEQ ID NO 28
<211> LENGTH: 466
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12-4 polypeptide CAR sequence

<400> SEQUENCE: 28

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
            20                  25                  30

Asp Ile Asn Trp Val Asn Gln Arg Pro Gly Gln Gly Leu Glu Trp Ile
        35                  40                  45

```
Gly Trp Ile Tyr Pro Gly Asp Gly Ser Thr Lys Tyr Asn Glu Lys Phe
         50                  55                  60

Lys Ala Lys Ala Thr Leu Thr Ala Asp Lys Ser Ser Ser Thr Ala Tyr
 65                  70                  75                  80

Leu Gln Leu Asn Asn Leu Thr Ser Glu Asn Ser Ala Val Tyr Phe Cys
                 85                  90                  95

Ala Ser Gly Tyr Glu Asp Ala Met Asp Tyr Trp Gly Gln Gly Thr Ser
                100                 105                 110

Val Thr Val Ser Ser Gly Gly Gly Ser Gly Gly Gly Ser Gly
             115                 120                 125

Gly Gly Gly Ser Asp Ile Lys Met Thr Gln Ser Pro Ser Ser Met Tyr
130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
                180                 185                 190

Arg Phe Ser Gly Ser Gly Ser Gly Gln Asp Tyr Ser Leu Thr Ile Ser
        195                 200                 205

Ser Leu Glu Tyr Glu Asp Met Gly Ile Tyr Tyr Cys Leu Gln Tyr Asp
210                 215                 220

Glu Phe Pro Leu Thr Phe Gly Ala Gly Thr Lys Leu Glu Leu Lys Arg
225                 230                 235                 240

Thr Thr Thr Pro Ala Pro Arg Pro Pro Thr Pro Ala Pro Thr Ile Ala
                245                 250                 255

Ser Gln Pro Leu Ser Leu Arg Pro Glu Ala Cys Arg Pro Ala Ala Gly
                260                 265                 270

Gly Ala Val His Thr Arg Gly Leu Asp Phe Ala Cys Asp Ile Ile Ser
            275                 280                 285

Phe Phe Leu Ala Leu Thr Ser Thr Ala Leu Leu Phe Leu Leu Phe Phe
290                 295                 300

Leu Thr Leu Arg Phe Ser Val Val Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
                340                 345                 350

Glu Leu Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
                420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
450                 455                 460

Pro Arg
```

<210> SEQ ID NO 29
<211> LENGTH: 649
<212> TYPE: PRT
<213> ORGANISM: artificial sequence
<220> FEATURE:
<223> OTHER INFORMATION: description of artificial sequence: synthetic oligopeptide
<220> FEATURE:
<223> OTHER INFORMATION: m2H12-5 polypeptide CAR sequence

<400> SEQUENCE: 29

Gln Val Gln Leu Gln Gln Ser Gly Pro Glu Leu Val Arg Pro Gly Thr
1               5                   10                  15

Phe Val Lys Ile Ser Cys Lys Ala Ser Gly Tyr Thr Phe Thr Asn Tyr
                20                  25                  30

Asp Ile Asn Trp Val Asn Gln Arg Pro Gly Gln Gly Leu Glu Trp Ile
            35                  40                  45

Gly Trp Ile Tyr Pro Gly Asp Gly Ser Thr Lys Tyr Asn Glu Lys Phe
    50                  55                  60

Lys Ala Lys Ala Thr Leu Thr Ala Asp Lys Ser Ser Ser Thr Ala Tyr
65                  70                  75                  80

Leu Gln Leu Asn Asn Leu Thr Ser Glu Asn Ser Ala Val Tyr Phe Cys
                85                  90                  95

Ala Ser Gly Tyr Glu Asp Ala Met Asp Tyr Trp Gly Gln Gly Thr Ser
            100                 105                 110

Val Thr Val Ser Ser Gly Gly Gly Ser Gly Gly Gly Gly Ser Gly
    115                 120                 125

Gly Gly Gly Ser Asp Ile Lys Met Thr Gln Ser Pro Ser Ser Met Tyr
130                 135                 140

Ala Ser Leu Gly Glu Arg Val Ile Ile Asn Cys Lys Ala Ser Gln Asp
145                 150                 155                 160

Ile Asn Ser Tyr Leu Ser Trp Phe Gln Gln Lys Pro Gly Lys Ser Pro
                165                 170                 175

Lys Thr Leu Ile Tyr Arg Ala Asn Arg Leu Val Asp Gly Val Pro Ser
            180                 185                 190

Arg Phe Ser Gly Ser Gly Ser Gly Gln Asp Tyr Ser Leu Thr Ile Ser
    195                 200                 205

Ser Leu Glu Tyr Glu Asp Met Gly Ile Tyr Tyr Cys Leu Gln Tyr Asp
        210                 215                 220

Glu Phe Pro Leu Thr Phe Gly Ala Gly Thr Lys Leu Glu Leu Lys Arg
225                 230                 235                 240

Glu Pro Lys Ser Pro Asp Lys Thr His Thr Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ala Arg Thr Pro Glu Val Thr Cys Val Val Val
    275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu

```
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Asp Glu Leu Thr Lys
            370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
            435                 440                 445
Cys Ser Val Met His Glu Ala Leu His Asn His Tyr Thr Gln Lys Ser
            450                 455                 460
Leu Ser Leu Ser Pro Gly Lys Ile Tyr Ile Trp Ala Pro Leu Ala Gly
465                 470                 475                 480
Thr Cys Gly Val Leu Leu Leu Ser Leu Val Ile Thr Leu Tyr Cys Lys
                485                 490                 495
Arg Gly Arg Lys Lys Leu Leu Tyr Ile Phe Lys Gln Pro Phe Met Arg
            500                 505                 510
Pro Val Gln Thr Thr Gln Glu Glu Asp Gly Cys Ser Cys Arg Phe Pro
            515                 520                 525
Glu Glu Glu Glu Gly Gly Cys Glu Leu Arg Val Lys Phe Ser Arg Ser
            530                 535                 540
Ala Asp Ala Pro Ala Tyr Gln Gln Gly Gln Asn Gln Leu Tyr Asn Glu
545                 550                 555                 560
Leu Asn Leu Gly Arg Arg Glu Glu Tyr Asp Val Leu Asp Lys Arg Arg
                565                 570                 575
Gly Arg Asp Pro Glu Met Gly Gly Lys Pro Arg Arg Lys Asn Pro Gln
            580                 585                 590
Glu Gly Leu Tyr Asn Glu Leu Gln Lys Asp Lys Met Ala Glu Ala Tyr
            595                 600                 605
Ser Glu Ile Gly Met Lys Gly Glu Arg Arg Arg Gly Lys Gly His Asp
            610                 615                 620
Gly Leu Tyr Gln Gly Leu Ser Thr Ala Thr Lys Asp Thr Tyr Asp Ala
625                 630                 635                 640
Leu His Met Gln Ala Leu Pro Pro Arg
                645

<210> SEQ ID NO 30
<211> LENGTH: 652
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: m2H12-6 polypeptide CAR sequence

<400> SEQUENCE: 30

Gln Val Gln Leu Gln Gln Ser Gly Pro Glu Leu Val Arg Pro Gly Thr
1               5                   10                  15
Phe Val Lys Ile Ser Cys Lys Ala Ser Gly Tyr Thr Phe Thr Asn Tyr
                20                  25                  30
Asp Ile Asn Trp Val Asn Gln Arg Pro Gly Gln Gly Leu Glu Trp Ile
```

```
                35                  40                  45
Gly Trp Ile Tyr Pro Gly Asp Gly Ser Thr Lys Tyr Asn Glu Lys Phe
 50                  55                  60
Lys Ala Lys Ala Thr Leu Thr Ala Asp Lys Ser Ser Thr Ala Tyr
 65                  70                  75                  80
Leu Gln Leu Asn Asn Leu Thr Ser Glu Asn Ser Ala Val Tyr Phe Cys
                 85                  90                  95
Ala Ser Gly Tyr Glu Asp Ala Met Asp Tyr Trp Gly Gln Gly Thr Ser
                100                 105                 110
Val Thr Val Ser Ser Gly Gly Gly Ser Gly Gly Gly Ser Gly
                115                 120                 125
Gly Gly Ser Asp Ile Lys Met Thr Gln Ser Pro Ser Ser Met Tyr
130                 135                 140
Ala Ser Leu Gly Glu Arg Val Ile Ile Asn Cys Lys Ala Ser Gln Asp
145                 150                 155                 160
Ile Asn Ser Tyr Leu Ser Trp Phe Gln Gln Lys Pro Gly Lys Ser Pro
                165                 170                 175
Lys Thr Leu Ile Tyr Arg Ala Asn Arg Leu Val Asp Gly Val Pro Ser
                180                 185                 190
Arg Phe Ser Gly Ser Gly Ser Gly Gln Asp Tyr Ser Leu Thr Ile Ser
                195                 200                 205
Ser Leu Glu Tyr Glu Asp Met Gly Ile Tyr Tyr Cys Leu Gln Tyr Asp
210                 215                 220
Glu Phe Pro Leu Thr Phe Gly Ala Gly Thr Lys Leu Glu Leu Lys Arg
225                 230                 235                 240
Glu Pro Lys Ser Pro Asp Lys Thr His Thr Cys Pro Pro Cys Pro Ala
                245                 250                 255
Pro Pro Val Ala Gly Pro Ser Val Phe Leu Phe Pro Pro Lys Pro Lys
                260                 265                 270
Asp Thr Leu Met Ile Ala Arg Thr Pro Glu Val Thr Cys Val Val Val
                275                 280                 285
Asp Val Ser His Glu Asp Pro Glu Val Lys Phe Asn Trp Tyr Val Asp
290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
                325                 330                 335
Trp Leu Asn Gly Lys Glu Tyr Lys Cys Lys Val Ser Asn Lys Ala Leu
                340                 345                 350
Pro Ala Pro Ile Glu Lys Thr Ile Ser Lys Ala Lys Gly Gln Pro Arg
                355                 360                 365
Glu Pro Gln Val Tyr Thr Leu Pro Pro Ser Arg Asp Glu Leu Thr Lys
                370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Val Leu Asp Ser Asp Gly Ser Phe Phe Leu Tyr Ser
                420                 425                 430
Lys Leu Thr Val Asp Lys Ser Arg Trp Gln Gln Gly Asn Val Phe Ser
                435                 440                 445
Cys Ser Val Met His Glu Ala Leu His Asn His Tyr Thr Gln Lys Ser
450                 455                 460
```

-continued

```
Leu Ser Leu Ser Pro Gly Lys Ile Ile Ser Phe Phe Leu Ala Leu Thr
465                 470                 475                 480

Ser Thr Ala Leu Leu Phe Leu Leu Phe Phe Leu Thr Leu Arg Phe Ser
                485                 490                 495

Val Val Lys Arg Gly Arg Lys Lys Leu Leu Tyr Ile Phe Lys Gln Pro
            500                 505                 510

Phe Met Arg Pro Val Gln Thr Thr Gln Glu Glu Asp Gly Cys Ser Cys
            515                 520                 525

Arg Phe Pro Glu Glu Glu Gly Gly Cys Glu Leu Arg Val Lys Phe
530                 535                 540

Ser Arg Ser Ala Asp Ala Pro Ala Tyr Gln Gln Gly Gln Asn Gln Leu
545                 550                 555                 560

Tyr Asn Glu Leu Asn Leu Gly Arg Arg Glu Glu Tyr Asp Val Leu Asp
                565                 570                 575

Lys Arg Arg Gly Arg Asp Pro Glu Met Gly Gly Lys Pro Arg Arg Lys
            580                 585                 590

Asn Pro Gln Glu Gly Leu Tyr Asn Glu Leu Gln Lys Asp Lys Met Ala
            595                 600                 605

Glu Ala Tyr Ser Glu Ile Gly Met Lys Gly Glu Arg Arg Arg Gly Lys
            610                 615                 620

Gly His Asp Gly Leu Tyr Gln Gly Leu Ser Thr Ala Thr Lys Asp Thr
625                 630                 635                 640

Tyr Asp Ala Leu His Met Gln Ala Leu Pro Pro Arg
                645                 650

<210> SEQ ID NO 31
<211> LENGTH: 444
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2-1 polypeptide CAR sequence

<400> SEQUENCE: 31

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160
```

Ser Ser Ser Val Asn Tyr Ile His Trp Tyr Gln Gln Lys Ser Gly Asp
            165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
            195                 200                 205

Ile Ser Thr Met Glu Ala Glu Asp Ala Ala Thr Tyr Tyr Cys Gln Gln
        210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Gly Leu Ala Val Ser Thr
                    245                 250                 255

Ile Ser Ser Phe Phe Pro Pro Gly Tyr Gln Ile Tyr Ile Trp Ala Pro
                260                 265                 270

Leu Ala Gly Thr Cys Gly Val Leu Leu Leu Ser Leu Val Ile Thr Leu
            275                 280                 285

Tyr Cys Lys Arg Gly Arg Lys Lys Leu Leu Tyr Ile Phe Lys Gln Pro
        290                 295                 300

Phe Met Arg Pro Val Gln Thr Thr Gln Glu Glu Asp Gly Cys Ser Cys
305                 310                 315                 320

Arg Phe Pro Glu Glu Glu Glu Gly Gly Cys Glu Leu Arg Val Lys Phe
                    325                 330                 335

Ser Arg Ser Ala Asp Ala Pro Ala Tyr Gln Gln Gly Gln Asn Gln Leu
                340                 345                 350

Tyr Asn Glu Leu Asn Leu Gly Arg Arg Glu Glu Tyr Asp Val Leu Asp
            355                 360                 365

Lys Arg Arg Gly Arg Asp Pro Glu Met Gly Gly Lys Pro Arg Arg Lys
        370                 375                 380

Asn Pro Gln Glu Gly Leu Tyr Asn Glu Leu Gln Lys Asp Lys Met Ala
385                 390                 395                 400

Glu Ala Tyr Ser Glu Ile Gly Met Lys Gly Glu Arg Arg Arg Gly Lys
                    405                 410                 415

Gly His Asp Gly Leu Tyr Gln Gly Leu Ser Thr Ala Thr Lys Asp Thr
                420                 425                 430

Tyr Asp Ala Leu His Met Gln Ala Leu Pro Pro Arg
            435                 440

<210> SEQ ID NO 32
<211> LENGTH: 447
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2-2 polypeptide CAR sequence

<400> SEQUENCE: 32

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Leu Thr Gln Ser Pro Thr
130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Asp Ala Ala Thr Tyr Tyr Cys Gln Gln
210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Gly Leu Ala Val Ser Thr
                245                 250                 255

Ile Ser Ser Phe Phe Pro Pro Gly Tyr Gln Ile Ile Ser Phe Phe Leu
            260                 265                 270

Ala Leu Thr Ser Thr Ala Leu Leu Phe Leu Leu Phe Phe Leu Thr Leu
        275                 280                 285

Arg Phe Ser Val Val Lys Arg Gly Arg Lys Lys Leu Leu Tyr Ile Phe
290                 295                 300

Lys Gln Pro Phe Met Arg Pro Val Gln Thr Thr Gln Glu Glu Asp Gly
305                 310                 315                 320

Cys Ser Cys Arg Phe Pro Glu Glu Glu Glu Gly Gly Cys Glu Leu Arg
                325                 330                 335

Val Lys Phe Ser Arg Ser Ala Asp Ala Pro Ala Tyr Gln Gln Gly Gln
            340                 345                 350

Asn Gln Leu Tyr Asn Glu Leu Asn Leu Gly Arg Arg Glu Glu Tyr Asp
        355                 360                 365

Val Leu Asp Lys Arg Arg Gly Arg Asp Pro Glu Met Gly Gly Lys Pro
370                 375                 380

Arg Arg Lys Asn Pro Gln Glu Gly Leu Tyr Asn Glu Leu Gln Lys Asp
385                 390                 395                 400

Lys Met Ala Glu Ala Tyr Ser Glu Ile Gly Met Lys Gly Glu Arg Arg
                405                 410                 415

Arg Gly Lys Gly His Asp Gly Leu Tyr Gln Gly Leu Ser Thr Ala Thr
            420                 425                 430

Lys Asp Thr Tyr Asp Ala Leu His Met Gln Ala Leu Pro Pro Arg
        435                 440                 445

<210> SEQ ID NO 33
<211> LENGTH: 473
<212> TYPE: PRT
<213> ORGANISM: artificial sequence
<220> FEATURE:

<223> OTHER INFORMATION: description of artificial sequence: synthetic oligopeptide
<220> FEATURE:
<223> OTHER INFORMATION: DRB2-3 polypeptide CAR sequence

<400> SEQUENCE: 33

```
Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
            20                  25                  30

Val Val His Trp Leu Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Ser Gly Gly Gly
            115                 120                 125

Gly Ser Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Asp Ala Ala Thr Tyr Tyr Cys Gln Gln
    210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Thr Thr Pro Ala Pro
                245                 250                 255

Arg Pro Pro Thr Pro Ala Pro Thr Ile Ala Ser Gln Pro Leu Ser Leu
            260                 265                 270

Arg Pro Glu Ala Cys Arg Pro Ala Ala Gly Gly Ala Val His Thr Arg
        275                 280                 285

Gly Leu Asp Phe Ala Cys Asp Ile Tyr Ile Trp Ala Pro Leu Ala Gly
    290                 295                 300

Thr Cys Gly Val Leu Leu Leu Ser Leu Val Ile Thr Leu Tyr Cys Lys
305                 310                 315                 320

Arg Gly Arg Lys Lys Leu Leu Tyr Ile Phe Lys Gln Pro Phe Met Arg
                325                 330                 335

Pro Val Gln Thr Thr Gln Glu Glu Asp Gly Cys Ser Cys Arg Phe Pro
            340                 345                 350

Glu Glu Glu Glu Gly Gly Cys Glu Leu Arg Val Lys Phe Ser Arg Ser
        355                 360                 365

Ala Asp Ala Pro Ala Tyr Gln Gln Gly Gln Asn Gln Leu Tyr Asn Glu
    370                 375                 380
```

```
Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
        435                 440                 445

Gly Leu Tyr Gln Gly Leu Ser Thr Ala Thr Lys Asp Thr Tyr Asp Ala
    450                 455                 460

Leu His Met Gln Ala Leu Pro Pro Arg
465                 470

<210> SEQ ID NO 34
<211> LENGTH: 476
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2-4 polypeptide CAR sequence

<400> SEQUENCE: 34

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
                20                  25                  30

Val Val His Trp Leu Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Gly Ser Gly Gly Gly
            115                 120                 125

Gly Ser Gly Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
        195                 200                 205

Ile Ser Thr Met Glu Ala Glu Asp Ala Ala Thr Tyr Tyr Cys Gln Gln
    210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Thr Thr Thr Pro Ala Pro
                245                 250                 255
```

Arg Pro Pro Thr Pro Ala Pro Thr Ile Ala Ser Gln Pro Leu Ser Leu
              260                 265                 270

Arg Pro Glu Ala Cys Arg Pro Ala Ala Gly Gly Ala Val His Thr Arg
          275                 280                 285

Gly Leu Asp Phe Ala Cys Asp Ile Ile Ser Phe Phe Leu Ala Leu Thr
      290                 295                 300

Ser Thr Ala Leu Leu Phe Leu Leu Phe Phe Leu Thr Leu Arg Phe Ser
305                 310                 315                 320

Val Val Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg
465                 470                 475

<210> SEQ ID NO 35
<211> LENGTH: 659
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2-5 polypeptide CAR sequence

<400> SEQUENCE: 35

Glu Val Lys Leu Gln Glu Ser Gly Pro Glu Leu Val Lys Pro Gly Ala
1               5                   10                  15

Ser Val Lys Met Ser Cys Lys Ala Ser Gly Tyr Lys Phe Thr Asp Tyr
                20                  25                  30

Val Val His Trp Leu Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Val Ser Ser Leu Thr Ser Glu Asp Ser Ala Val Tyr Tyr Cys
                85                  90                  95

Ala Arg Asp Tyr Arg Tyr Glu Val Tyr Gly Met Asp Tyr Trp Gly Gln
                100                 105                 110

Gly Thr Ser Val Thr Val Ser Ser Gly Gly Gly Ser Gly Gly Gly
            115                 120                 125

```
Gly Ser Gly Gly Gly Ser Asp Ile Val Leu Thr Gln Ser Pro Thr
    130                 135                 140

Ile Met Ser Ala Ser Pro Gly Glu Arg Val Thr Met Thr Cys Thr Ala
145                 150                 155                 160

Ser Ser Ser Val Asn Tyr Ile His Trp Tyr Gln Gln Lys Ser Gly Asp
                165                 170                 175

Ser Pro Leu Arg Trp Ile Phe Asp Thr Ser Lys Val Ala Ser Gly Val
            180                 185                 190

Pro Ala Arg Phe Ser Gly Ser Gly Ser Gly Thr Ser Tyr Ser Leu Thr
            195                 200                 205

Ile Ser Thr Met Glu Ala Glu Asp Ala Ala Thr Tyr Tyr Cys Gln Gln
    210                 215                 220

Trp Arg Ser Tyr Pro Leu Thr Phe Gly Asp Gly Thr Arg Leu Glu Leu
225                 230                 235                 240

Lys Arg Ala Asp Ala Ala Pro Thr Val Ser Glu Pro Lys Ser Pro Asp
                245                 250                 255

Lys Thr His Thr Cys Pro Pro Cys Pro Ala Pro Pro Val Ala Gly Pro
            260                 265                 270

Ser Val Phe Leu Phe Pro Pro Lys Pro Lys Asp Thr Leu Met Ile Ala
    275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Ile Tyr Ile Trp Ala Pro Leu Ala Gly Thr Cys Gly Val Leu Leu
                485                 490                 495

Leu Ser Leu Val Ile Thr Leu Tyr Cys Lys Arg Gly Arg Lys Lys Leu
            500                 505                 510

Leu Tyr Ile Phe Lys Gln Pro Phe Met Arg Pro Val Gln Thr Thr Gln
            515                 520                 525

Glu Glu Asp Gly Cys Ser Cys Arg Phe Pro Glu Glu Glu Glu Gly Gly
    530                 535                 540

Cys Glu Leu Arg Val Lys Phe Ser Arg Ser Ala Asp Ala Pro Ala Tyr
```

```
545                 550                 555                 560
Gln Gln Gly Gln Asn Gln Leu Tyr Asn Glu Leu Asn Leu Gly Arg Arg
                565                 570                 575
Glu Glu Tyr Asp Val Leu Asp Lys Arg Arg Gly Arg Asp Pro Glu Met
            580                 585                 590
Gly Gly Lys Pro Arg Lys Asn Pro Gln Glu Gly Leu Tyr Asn Glu
            595                 600                 605
Leu Gln Lys Asp Lys Met Ala Glu Ala Tyr Ser Glu Ile Gly Met Lys
        610                 615                 620
Gly Glu Arg Arg Gly Lys Gly His Asp Gly Leu Tyr Gln Gly Leu
625                 630                 635                 640
Ser Thr Ala Thr Lys Asp Thr Tyr Asp Ala Leu His Met Gln Ala Leu
                645                 650                 655
Pro Pro Arg

<210> SEQ ID NO 36
<211> LENGTH: 662
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: DRB2-6 polypeptide CAR sequence

<400> SEQUENCE: 36

Glu Val Lys Leu Gln Glu Ser Gly Pro Glu Leu Val Lys Pro Gly Ala
1               5                   10                  15
Ser Val Lys Met Ser Cys Lys Ala Ser Gly Tyr Lys Phe Thr Asp Tyr
            20                  25                  30
Val Val His Trp Leu Lys Gln Lys Pro Gly Gln Gly Leu Glu Trp Ile
        35                  40                  45
Gly Tyr Ile Asn Pro Tyr Asn Asp Gly Thr Lys Tyr Asn Glu Lys Phe
    50                  55                  60
Lys Gly Lys Ala Thr Leu Thr Ser Asp Lys Ser Ser Ser Thr Ala Tyr
65                  70                  75                  80
Met Glu Val Ser Ser Leu Thr Ser Glu Asp Ser Ala Val Tyr Tyr Cys
                85                  90                  95
Ala Arg Asp Tyr Arg Tyr Glu Val Tyr Gly Met Asp Tyr Trp Gly Gln
            100                 105                 110
Gly Thr Ser Val Thr Val Ser Ser Gly Gly Gly Gly Ser Gly Gly Gly
        115                 120                 125
Gly Ser Gly Gly Gly Gly Ser Asp Ile Val Leu Thr Gln Ser Pro Thr
    130                 135                 140
Ile Met Ser Ala Ser Pro Gly Glu Arg Val Thr Met Thr Cys Thr Ala
145                 150                 155                 160
Ser Ser Ser Val Asn Tyr Ile His Trp Tyr Gln Gln Lys Ser Gly Asp
                165                 170                 175
Ser Pro Leu Arg Trp Ile Phe Asp Thr Ser Lys Val Ala Ser Gly Val
            180                 185                 190
Pro Ala Arg Phe Ser Gly Ser Gly Ser Gly Thr Ser Tyr Ser Leu Thr
        195                 200                 205
Ile Ser Thr Met Glu Ala Glu Asp Ala Ala Thr Tyr Tyr Cys Gln Gln
    210                 215                 220
Trp Arg Ser Tyr Pro Leu Thr Phe Gly Asp Gly Thr Arg Leu Glu Leu
225                 230                 235                 240
```

-continued

```
Lys Arg Ala Asp Ala Ala Pro Thr Val Ser Glu Pro Lys Ser Pro Asp
                245                 250                 255

Lys Thr His Thr Cys Pro Pro Cys Pro Ala Pro Val Ala Gly Pro
            260                 265                 270

Ser Val Phe Leu Phe Pro Pro Lys Pro Lys Asp Thr Leu Met Ile Ala
        275                 280                 285

Arg Thr Pro Glu Val Thr Cys Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys Ile Ile Ser Phe Phe Leu Ala Leu Thr Ser Thr Ala Leu Leu Phe
                485                 490                 495

Leu Leu Phe Phe Leu Thr Leu Arg Phe Ser Val Val Lys Arg Gly Arg
            500                 505                 510

Lys Lys Leu Leu Tyr Ile Phe Lys Gln Pro Phe Met Arg Pro Val Gln
        515                 520                 525

Thr Thr Gln Glu Glu Asp Gly Cys Ser Cys Arg Phe Pro Glu Glu Glu
    530                 535                 540

Glu Gly Gly Cys Glu Leu Arg Val Lys Phe Ser Arg Ser Ala Asp Ala
545                 550                 555                 560

Pro Ala Tyr Gln Gln Gly Gln Asn Gln Leu Tyr Asn Glu Leu Asn Leu
                565                 570                 575

Gly Arg Arg Glu Glu Tyr Asp Val Leu Asp Lys Arg Arg Gly Arg Asp
            580                 585                 590

Pro Glu Met Gly Gly Lys Pro Arg Arg Lys Asn Pro Gln Glu Gly Leu
        595                 600                 605

Tyr Asn Glu Leu Gln Lys Asp Lys Met Ala Glu Ala Tyr Ser Glu Ile
    610                 615                 620

Gly Met Lys Gly Glu Arg Arg Arg Gly Lys Gly His Asp Gly Leu Tyr
625                 630                 635                 640

Gln Gly Leu Ser Thr Ala Thr Lys Asp Thr Tyr Asp Ala Leu His Met
                645                 650                 655
```

Gln Ala Leu Pro Pro Arg
        660

<210> SEQ ID NO 37
<211> LENGTH: 440
<212> TYPE: PRT
<213> ORGANISM: artificial sequence
<220> FEATURE:
<223> OTHER INFORMATION: description of artificial sequence: synthetic
     oligopeptide
<220> FEATURE:
<223> OTHER INFORMATION: My9-6-1 polypeptide CAR sequence

<400> SEQUENCE: 37

Gln Val Gln Leu Gln Gln Pro Gly Ala Glu Val Val Lys Pro Gly Ala
1               5                  10               15

Ser Val Lys Met Ser Cys Lys Ala Ser Gly Tyr Thr Phe Thr Ser Tyr
             20                  25               30

Tyr Ile His Trp Ile Lys Gln Thr Pro Gly Gln Gly Leu Glu Trp Val
             35                  40               45

Gly Val Ile Tyr Pro Gly Asn Asp Asp Ile Ser Tyr Asn Gln Lys Phe
     50                   55                  60

Lys Gly Lys Ala Thr Leu Thr Ala Asp Lys Ser Ser Thr Thr Ala Tyr
65               70                  75               80

Met Gln Leu Ser Ser Leu Thr Ser Glu Asp Ser Ala Val Tyr Tyr Cys
             85                  90               95

Ala Arg Glu Val Arg Leu Arg Tyr Phe Asp Val Trp Gly Ala Gly Thr
           100                 105              110

Thr Val Thr Val Ser Ser Gly Gly Gly Gly Ser Gly Gly Gly Gly Ser
           115                 120              125

Gly Gly Gly Gly Ser Asn Ile Met Leu Thr Gln Ser Pro Ser Ser Leu
     130                 135                  140

Ala Val Ser Ala Gly Glu Lys Val Thr Met Ser Cys Lys Ser Ser Gln
145              150                 155              160

Ser Val Phe Phe Ser Ser Ser Gln Lys Asn Tyr Leu Ala Trp Tyr Gln
           165                 170              175

Gln Ile Pro Gly Gln Ser Pro Lys Leu Leu Ile Tyr Trp Ala Ser Thr
           180                 185              190

Arg Glu Ser Gly Val Pro Asp Arg Phe Thr Gly Ser Gly Ser Gly Thr
           195                 200              205

Asp Phe Thr Leu Thr Ile Ser Ser Val Gln Ser Glu Asp Leu Ala Ile
     210                 215                  220

Tyr Tyr Cys His Gln Tyr Leu Ser Ser Arg Thr Phe Gly Gly Gly Thr
225              230                 235              240

Lys Leu Glu Ile Lys Arg Gly Leu Ala Val Ser Thr Ile Ser Ser Phe
           245                 250              255

Phe Pro Pro Gly Tyr Gln Ile Tyr Ile Trp Ala Pro Leu Ala Gly Thr
           260                 265              270

Cys Gly Val Leu Leu Leu Ser Leu Val Ile Thr Leu Tyr Cys Lys Arg
           275                 280              285

Gly Arg Lys Lys Leu Leu Tyr Ile Phe Lys Gln Pro Phe Met Arg Pro
     290                 295                  300

Val Gln Thr Thr Gln Glu Glu Asp Gly Cys Ser Cys Arg Phe Pro Glu
305              310                 315              320

Glu Glu Glu Gly Gly Cys Glu Leu Arg Val Lys Phe Ser Arg Ser Ala
           325                 330              335

Asp Ala Pro Ala Tyr Gln Gln Gly Gln Asn Gln Leu Tyr Asn Glu Leu
                340                 345                 350

Asn Leu Gly Arg Arg Glu Glu Tyr Asp Val Leu Asp Lys Arg Arg Gly
            355                 360                 365

Arg Asp Pro Glu Met Gly Gly Lys Pro Arg Arg Lys Asn Pro Gln Glu
        370                 375                 380

Gly Leu Tyr Asn Glu Leu Gln Lys Asp Lys Met Ala Glu Ala Tyr Ser
385                 390                 395                 400

Glu Ile Gly Met Lys Gly Glu Arg Arg Arg Gly Lys Gly His Asp Gly
                405                 410                 415

Leu Tyr Gln Gly Leu Ser Thr Ala Thr Lys Asp Thr Tyr Asp Ala Leu
        420                 425                 430

His Met Gln Ala Leu Pro Pro Arg
        435                 440

<210> SEQ ID NO 38
<211> LENGTH: 443
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6-2 polypeptide CAR sequence

<400> SEQUENCE: 38

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
        50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

```
Lys Leu Glu Ile Lys Arg Gly Leu Ala Val Ser Thr Ile Ser Ser Phe
                245                 250                 255

Phe Pro Pro Gly Tyr Gln Ile Ile Ser Phe Leu Ala Leu Thr Ser
        260                 265                 270

Thr Ala Leu Leu Phe Leu Leu Phe Leu Thr Leu Arg Phe Ser Val
            275                 280                 285

Val Lys Arg Gly Arg Lys Lys Leu Leu Tyr Ile Phe Lys Gln Pro Phe
    290                 295                 300

Met Arg Pro Val Gln Thr Thr Gln Glu Glu Asp Gly Cys Ser Cys Arg
305                 310                 315                 320

Phe Pro Glu Glu Glu Glu Gly Gly Cys Glu Leu Arg Val Lys Phe Ser
                325                 330                 335

Arg Ser Ala Asp Ala Pro Ala Tyr Gln Gln Gly Gln Asn Gln Leu Tyr
                340                 345                 350

Asn Glu Leu Asn Leu Gly Arg Arg Glu Glu Tyr Asp Val Leu Asp Lys
            355                 360                 365

Arg Arg Gly Arg Asp Pro Glu Met Gly Gly Lys Pro Arg Arg Lys Asn
    370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
                420                 425                 430

Asp Ala Leu His Met Gln Ala Leu Pro Pro Arg
            435                 440

<210> SEQ ID NO 39
<211> LENGTH: 469
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6-3 polypeptide CAR sequence

<400> SEQUENCE: 39

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Gly Ser Gly Gly Gly Gly Ser
            115                 120                 125

Gly Gly Gly Gly Ser Asn Ile Met Leu Thr Gln Ser Pro Ser Ser Leu
    130                 135                 140
```

```
Ala Val Ser Ala Gly Glu Lys Val Thr Met Ser Cys Lys Ser Ser Gln
145                 150                 155                 160

Ser Val Phe Phe Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Thr Thr Thr Pro Ala Pro Arg Pro Pro Thr
                245                 250                 255

Pro Ala Pro Thr Ile Ala Ser Gln Pro Leu Ser Leu Arg Pro Glu Ala
                260                 265                 270

Cys Arg Pro Ala Ala Gly Gly Ala Val His Thr Arg Gly Leu Asp Phe
            275                 280                 285

Ala Cys Asp Ile Tyr Ile Trp Ala Pro Leu Ala Gly Thr Cys Gly Val
        290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
                340                 345                 350

Gly Gly Cys Glu Leu Arg Val Lys Phe Ser Arg Ser Ala Asp Ala Pro
            355                 360                 365

Ala Tyr Gln Gln Gly Gln Asn Gln Leu Tyr Asn Glu Leu Asn Leu Gly
        370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
        450                 455                 460

Ala Leu Pro Pro Arg
465

<210> SEQ ID NO 40
<211> LENGTH: 472
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6-4 polypeptide CAR sequence

<400> SEQUENCE: 40

Gln Val Gln Leu Gln Gln Pro Gly Ala Glu Val Val Lys Pro Gly Ala
1               5                   10                  15
```

```
Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Ser Gly Gly Gly Gly Ser
            115                 120                 125

Gly Gly Gly Gly Ser Asn Ile Met Leu Thr Gln Ser Pro Ser Ser Leu
        130                 135                 140

Ala Val Ser Ala Gly Glu Lys Val Thr Met Ser Cys Lys Ser Ser Gln
145                 150                 155                 160

Ser Val Phe Phe Ser Ser Gln Lys Asn Tyr Leu Ala Trp Tyr Gln
            165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
            195                 200                 205

Asp Phe Thr Leu Thr Ile Ser Ser Val Gln Ser Glu Asp Leu Ala Ile
210                 215                 220

Tyr Tyr Cys His Gln Tyr Leu Ser Ser Arg Thr Phe Gly Gly Gly Thr
225                 230                 235                 240

Lys Leu Glu Ile Lys Arg Thr Thr Thr Pro Ala Pro Arg Pro Pro Thr
            245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
            275                 280                 285

Ala Cys Asp Ile Ile Ser Phe Phe Leu Ala Leu Thr Ser Thr Ala Leu
290                 295                 300

Leu Phe Leu Leu Phe Phe Leu Thr Leu Arg Phe Ser Val Val Lys Arg
305                 310                 315                 320

Gly Arg Lys Lys Leu Leu Tyr Ile Phe Lys Gln Pro Phe Met Arg Pro
            325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
            355                 360                 365

Asp Ala Pro Ala Tyr Gln Gln Gly Gln Asn Gln Leu Tyr Asn Glu Leu
            370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
```

```
                435                 440                 445
Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 41
<211> LENGTH: 655
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6-5 polypeptide CAR sequence

<400> SEQUENCE: 41

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Gly Ser Gly Gly Gly Gly Ser
        115                 120                 125

Gly Gly Gly Gly Ser Asn Ile Met Leu Thr Gln Ser Pro Ser Ser Leu
    130                 135                 140

Ala Val Ser Ala Gly Glu Lys Val Thr Met Ser Cys Lys Ser Ser Gln
145                 150                 155                 160

Ser Val Phe Phe Ser Ser Gln Lys Asn Tyr Leu Ala Trp Tyr Gln
                165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ser Glu Asp Leu Ala Ile
    210                 215                 220

Tyr Tyr Cys His Gln Tyr Leu Ser Ser Arg Thr Phe Gly Gly Gly Thr
225                 230                 235                 240

Lys Leu Glu Ile Lys Arg Glu Pro Lys Ser Pro Asp Lys Thr His Thr
                245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ala Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
```

```
            305                 310                 315                 320
Pro Arg Glu Glu Gln Tyr Asn Ser Thr Tyr Arg Val Ser Val Leu
                325                 330                 335

Thr Val Leu His Gln Asp Trp Leu Asn Gly Lys Glu Tyr Lys Cys Lys
                340                 345                 350

Val Ser Asn Lys Ala Leu Pro Ala Pro Ile Glu Lys Thr Ile Ser Lys
                355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
                420                 425                 430

Ser Phe Phe Leu Tyr Ser Lys Leu Thr Val Asp Lys Ser Arg Trp Gln
                435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys Ile Tyr Ile
465                 470                 475                 480

Trp Ala Pro Leu Ala Gly Thr Cys Gly Val Leu Leu Leu Ser Leu Val
                485                 490                 495

Ile Thr Leu Tyr Cys Lys Arg Gly Arg Lys Lys Leu Leu Tyr Ile Phe
                500                 505                 510

Lys Gln Pro Phe Met Arg Pro Val Gln Thr Thr Gln Glu Glu Asp Gly
                515                 520                 525

Cys Ser Cys Arg Phe Pro Glu Glu Glu Glu Gly Gly Cys Glu Leu Arg
                530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
                580                 585                 590

Arg Arg Lys Asn Pro Gln Glu Gly Leu Tyr Asn Glu Leu Gln Lys Asp
                595                 600                 605

Lys Met Ala Glu Ala Tyr Ser Glu Ile Gly Met Lys Gly Glu Arg Arg
610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg
                645                 650                 655

<210> SEQ ID NO 42
<211> LENGTH: 658
<212> TYPE: PRT
<213> ORGANISM: artificial sequence
<220> FEATURE:
<223> OTHER INFORMATION: description of artificial sequence: synthetic
      oligopeptide
<220> FEATURE:
<223> OTHER INFORMATION: My9-6-6 polypeptide CAR sequence

<400> SEQUENCE: 42

Gln Val Gln Leu Gln Gln Pro Gly Ala Glu Val Val Lys Pro Gly Ala
```

-continued

```
1               5                   10                  15
Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
            50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
            85                  90                  95

Ala Arg Glu Val Arg Leu Arg Tyr Phe Asp Val Trp Gly Ala Gly Thr
            100                 105                 110

Thr Val Thr Val Ser Ser Gly Gly Gly Ser Gly Gly Gly Gly Gly Ser
            115                 120                 125

Gly Gly Gly Gly Ser Asn Ile Met Leu Thr Gln Ser Pro Ser Ser Leu
            130                 135                 140

Ala Val Ser Ala Gly Glu Lys Val Thr Met Ser Cys Lys Ser Ser Gln
145                 150                 155                 160

Ser Val Phe Phe Ser Ser Ser Gln Lys Asn Tyr Leu Ala Trp Tyr Gln
            165                 170                 175

Gln Ile Pro Gly Gln Ser Pro Lys Leu Leu Ile Tyr Trp Ala Ser Thr
            180                 185                 190

Arg Glu Ser Gly Val Pro Asp Arg Phe Thr Gly Ser Gly Ser Gly Thr
            195                 200                 205

Asp Phe Thr Leu Thr Ile Ser Ser Val Gln Ser Glu Asp Leu Ala Ile
            210                 215                 220

Tyr Tyr Cys His Gln Tyr Leu Ser Ser Arg Thr Phe Gly Gly Gly Thr
225                 230                 235                 240

Lys Leu Glu Ile Lys Arg Glu Pro Lys Ser Pro Asp Lys Thr His Thr
            245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ala Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430
```

```
Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Ile Ile Ser
465                 470                 475                 480

Phe Phe Leu Ala Leu Thr Ser Thr Ala Leu Leu Phe Leu Leu Phe Phe
                485                 490                 495

Leu Thr Leu Arg Phe Ser Val Val Lys Arg Gly Arg Lys Lys Leu Leu
            500                 505                 510

Tyr Ile Phe Lys Gln Pro Phe Met Arg Pro Val Gln Thr Thr Gln Glu
        515                 520                 525

Glu Asp Gly Cys Ser Cys Arg Phe Pro Glu Glu Glu Glu Gly Gly Cys
530                 535                 540

Glu Leu Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
        595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg

<210> SEQ ID NO 43
<211> LENGTH: 49
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: Target TALEN TRAC_T01

<400> SEQUENCE: 43

Thr Thr Gly Thr Cys Cys Cys Ala Cys Ala Gly Ala Thr Ala Thr Cys
1               5                   10                  15

Cys Ala Gly Ala Ala Cys Cys Cys Thr Gly Ala Cys Cys Cys Thr Gly
            20                  25                  30

Cys Cys Gly Thr Gly Thr Ala Cys Cys Ala Gly Cys Thr Gly Ala Gly
        35                  40                  45

Ala

<210> SEQ ID NO 44
<211> LENGTH: 530
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: TAL binding domain TRAC_T01-L
```

```
<400> SEQUENCE: 44

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
```

-continued

```
                        405                 410                 415
Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 45
<211> LENGTH: 530
<212> TYPE: PRT
<213> ORGANISM: Artificial sequence
<220> FEATURE:
<223> OTHER INFORMATION: description of artificial sequence: synthetic
      oligopeptide
<220> FEATURE:
<223> OTHER INFORMATION: TAL binding domain TRAC_T01-R

<400> SEQUENCE: 45

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
```

```
                210             215             220
Thr Val Gln Arg Leu Leu Pro Val Leu Cys Gln Ala His Gly Leu Thr
225             230             235             240

Pro Gln Gln Val Val Ala Ile Ala Ser Asn Asn Gly Gly Lys Gln Ala
                245             250             255

Leu Glu Thr Val Gln Arg Leu Leu Pro Val Leu Cys Gln Ala His Gly
            260             265             270

Leu Thr Pro Gln Gln Val Val Ala Ile Ala Ser Asn Asn Gly Gly Lys
        275             280             285

Gln Ala Leu Glu Thr Val Gln Arg Leu Leu Pro Val Leu Cys Gln Ala
    290             295             300

His Gly Leu Thr Pro Gln Gln Val Val Ala Ile Ala Ser Asn Gly Gly
305             310             315             320

Gly Lys Gln Ala Leu Glu Thr Val Gln Arg Leu Leu Pro Val Leu Cys
                325             330             335

Gln Ala His Gly Leu Thr Pro Glu Gln Val Val Ala Ile Ala Ser Asn
            340             345             350

Ile Gly Gly Lys Gln Ala Leu Glu Thr Val Gln Ala Leu Leu Pro Val
        355             360             365

Leu Cys Gln Ala His Gly Leu Thr Pro Glu Gln Val Val Ala Ile Ala
    370             375             380

Ser His Asp Gly Gly Lys Gln Ala Leu Glu Thr Val Gln Arg Leu Leu
385             390             395             400

Pro Val Leu Cys Gln Ala His Gly Leu Thr Pro Glu Gln Val Val Ala
                405             410             415

Ile Ala Ser Asn Ile Gly Gly Lys Gln Ala Leu Glu Thr Val Gln Ala
            420             425             430

Leu Leu Pro Val Leu Cys Gln Ala His Gly Leu Thr Pro Glu Gln Val
        435             440             445

Val Ala Ile Ala Ser His Asp Gly Gly Lys Gln Ala Leu Glu Thr Val
    450             455             460

Gln Arg Leu Leu Pro Val Leu Cys Gln Ala His Gly Leu Thr Pro Gln
465             470             475             480

Gln Val Val Ala Ile Ala Ser Asn Asn Gly Gly Lys Gln Ala Leu Glu
                485             490             495

Thr Val Gln Arg Leu Leu Pro Val Leu Cys Gln Ala His Gly Leu Thr
            500             505             510

Pro Gln Gln Val Val Ala Ile Ala Ser Asn Gly Gly Gly Arg Pro Ala
        515             520             525

Leu Glu
    530
```

<210> SEQ ID NO 46
<211> LENGTH: 2814
<212> TYPE: DNA
<213> ORGANISM: Artificial sequence
<220> FEATURE:
<223> OTHER INFORMATION: description of artificial sequence: synthetic polynucleotide
<220> FEATURE:
<223> OTHER INFORMATION: polynucleotide encoding TRAC_T01-L TALEN
<400> SEQUENCE: 46

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
```

| | |
|---|---|
| aaaccgaagg ttcgttcgac agtggcgcag caccacgagg cactggtcgg ccacgggttt | 180 |
| acacacgcgc acatcgttgc gttaagccaa caccCggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccCc agcaggtggt ggccatcgcc agcaatggcg gtggcaagca ggcgctggag | 540 |
| acggtccagc ggctgttgcc ggtgctgtgc caggcccacg gcttgacccc ccagcaggtg | 600 |
| gtggccatcg ccagcaataa tggtggcaag caggcgctgg acggtccag cggctgttg | 660 |
| ccggtgctgt gccaggccca cggcttgacc ccccagcagg tggtggccat cgccagcaat | 720 |
| ggcggtggca agcaggcgct ggagacggtc cagcggctgt tgccggtgct gtgccaggcc | 780 |
| cacggcttga ccccggagca ggtggtggcc atcgccagcc acgatggcgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg gcggcaagca ggcgctggag acggtccagc ggctgttgcc ggtgctgtgc | 1080 |
| caggcccacg gcttgacccc ggagcaggtg gtggccatcg ccagcaatat tggtggcaag | 1140 |
| caggcgctgg agacggtgca ggcgctgttg ccggtgctgt gccaggccca cggcttgacc | 1200 |
| ccggagcagg tggtggccat cgccagccac gatggcggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gaccccccag caggtggtgg ccatcgccag caataatggt | 1440 |
| ggcaagcagg cgctggagac ggtccagcgg ctgttgccgg tgctgtgcca ggcccacggc | 1500 |
| ttgaccccgg agcaggtggt ggccatcgcc agcaatattg gtggcaagca ggcgctggag | 1560 |
| acggtgcagg cgctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtg caggcgctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |
| ctgttgccgg tgctgtgcca ggcccacggc ttgaccccTc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acgcgccat ctacaccgtg gctcccccca tcgactacgg cgtgatcgtg | 2460 |
| gacaccaagg cctactccgg cggctacaac ctgcccatcg ccaggccga cgaaatgcag | 2520 |

```
aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 47
<211> LENGTH: 2832
<212> TYPE: DNA
<213> ORGANISM: Artificial sequence
<220> FEATURE:
<223> OTHER INFORMATION: description of artificial sequence: synthetic
    polynucleotide
<220> FEATURE:
<223> OTHER INFORMATION: polynucleotide encoding TRAC_T01-R TALEN

<400> SEQUENCE: 47

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacga tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcac gttgccaga ggcgacacac     300 gaagcgatcg ttggcgtcgg caaacagtgg tccggcgcac gcgctctgga ggccttgctc    360 acggtggcg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccgag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtc aggcgctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag    1020
caggtggtgg ccatcgccag ccacgatggc ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaataa tggtggcaag    1260
caggcgctgg agacggtcca gcggctgttg ccggtgctgt gccaggccca cggcttgacc    1320
ccccagcagg tggtggccat cgccagcaat aatggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgaccccgg agcaggtggt ggccatcgcc agccacgatg gcggcaagca ggcgctggag    1680
```

```
acggtccagc ggctgttgcc ggtgctgtgc caggcccacg gcttgacccc ggagcaggtg      1740
gtggccatcg ccagcaatat tggtggcaag caggcgctgg agacggtgca ggcgctgttg      1800
ccggtgctgt gccaggccca cggcttgacc ccggagcagg tggtggccat cgccagccac      1860
gatggcggca agcaggcgct ggagacggtc agcggctgt tgccggtgct gtgccaggcc       1920
cacggcttga ccccccagca ggtggtggcc atcgccagca ataatggtgg caagcaggcg      1980
ctggagacgg tccagcggct gttgccggtg ctgtgccagg cccacggctt gacccctcag      2040
caggtggtgg ccatcgccag caatggcggc ggcaggccgg cgctggagag cattgttgcc      2100
cagttatctc gccctgatcc ggcgttggcc gcgttgacca acgaccacct cgtcgccttg      2160
gcctgcctcg gcgggcgtcc tgcgctggat gcagtgaaaa agggattggg ggatcctatc      2220
agccgttccc agctggtgaa gtccgagctg gaggagaaga atccgagtt gaggcacaag       2280 ctgaagtacg tgccccacga gtacatcgag ctgatcgaga tcgcccggaa cagcacccag      2340
gaccgtatcc tggagatgaa ggtgatgag ttcttcatga aggtgtacgg ctacaggggc       2400
aagcacctgg gcggctccag gaagcccgac ggcgccatct acaccgtggg ctcccccatc      2460
gactacggcg tgatcgtgga caccaaggcc tactccggcg gctacaacct gcccatcggc      2520
caggccgacg aaatgcagag gtacgtggag gagaaccaga ccaggaacaa gcacatcaac      2580
cccaacgagt ggtggaaggt gtacccctcc agcgtgaccg agttcaagtt cctgttcgtg      2640
tccggccact tcaagggcaa ctacaaggcc cagctgacca ggctgaacca tcaccaac       2700 tgcaacggcg ccgtgctgtc cgtggaggag ctcctgatcg cggcgagat gatcaaggcc      2760 ggcaccctga ccctggagga ggtgaggagg aagttcaaca cggcgagat caacttcgcg     2820 gccgactgat aa                                                         2832

<210> SEQ ID NO 48
<211> LENGTH: 457
<212> TYPE: PRT
<213> ORGANISM: Artificial sequence
<220> FEATURE:
<223> OTHER INFORMATION: M195-1

<400> SEQUENCE: 48

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Ile Ser Cys Lys Ala Ser Gly Tyr
            35                  40                  45

Thr Phe Thr Asp Tyr Asn Met His Trp Val Lys Gln Ser His Gly Lys
        50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

Gln Gly Thr Ser Val Thr Val Ser Ser Gly Gly Gly Ser Gly Gly
    130                 135                 140

Gly Gly Ser Gly Gly Gly Gly Ser Asp Ile Val Leu Thr Gln Ser Pro
```

```
                145                 150                 155                 160
Ala Ser Leu Ala Val Ser Leu Gly Gln Arg Ala Thr Ile Ser Cys Arg
                165                 170                 175

Ala Ser Glu Ser Val Asp Asn Tyr Gly Ile Ser Phe Met Asn Trp Phe
            180                 185                 190

Gln Gln Lys Pro Gly Gln Pro Pro Lys Leu Leu Ile Tyr Ala Ala Ser
        195                 200                 205

Asn Gln Gly Ser Gly Val Pro Ala Arg Phe Ser Gly Ser Gly Ser Gly
    210                 215                 220

Thr Asp Phe Ser Leu Asn Ile His Pro Met Glu Glu Asp Asp Thr Ala
225                 230                 235                 240

Met Tyr Phe Cys Gln Gln Ser Lys Glu Val Pro Trp Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Ile Tyr Ile Trp Ala Pro Leu Ala Gly
        275                 280                 285

Thr Cys Gly Val Leu Leu Leu Ser Leu Val Ile Thr Leu Tyr Cys Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg
    450                 455

<210> SEQ ID NO 49
<211> LENGTH: 460
<212> TYPE: PRT
<213> ORGANISM: Artificial sequence
<220> FEATURE:
<223> OTHER INFORMATION: M195-2

<400> SEQUENCE: 49

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Thr Phe Thr Asp Tyr Asn Met His Trp Val Lys Gln Ser His Gly Lys
```

```
                 50                  55                  60
Ser Leu Glu Trp Ile Gly Tyr Ile Tyr Pro Tyr Asn Gly Thr Gly
 65                  70                  75                  80

Tyr Asn Gln Lys Phe Lys Ser Lys Ala Thr Leu Thr Val Asp Asn Ser
                 85                  90                  95

Ser Ser Thr Ala Tyr Met Asp Val Arg Ser Leu Thr Ser Glu Asp Ser
                100                 105                 110

Ala Val Tyr Tyr Cys Ala Arg Gly Arg Pro Ala Met Asp Tyr Trp Gly
                115                 120                 125

Gln Gly Thr Ser Val Thr Val Ser Ser Gly Gly Gly Ser Gly Gly
            130                 135                 140

Gly Gly Ser Gly Gly Gly Ser Asp Ile Val Leu Thr Gln Ser Pro
145                 150                 155                 160

Ala Ser Leu Ala Val Ser Leu Gly Gln Arg Ala Thr Ile Ser Cys Arg
                165                 170                 175

Ala Ser Glu Ser Val Asp Asn Tyr Gly Ile Ser Phe Met Asn Trp Phe
                180                 185                 190

Gln Gln Lys Pro Gly Gln Pro Pro Lys Leu Leu Ile Tyr Ala Ala Ser
                195                 200                 205

Asn Gln Gly Ser Gly Val Pro Ala Arg Phe Ser Gly Ser Gly Ser Gly
210                 215                 220

Thr Asp Phe Ser Leu Asn Ile His Pro Met Glu Glu Asp Asp Thr Ala
225                 230                 235                 240

Met Tyr Phe Cys Gln Gln Ser Lys Glu Val Pro Trp Thr Phe Gly Gly
                245                 250                 255

Gly Thr Lys Leu Glu Ile Lys Gly Leu Ala Val Ser Thr Ile Ser Ser
                260                 265                 270

Phe Phe Pro Pro Gly Tyr Gln Ile Ile Ser Phe Leu Ala Leu Thr
            275                 280                 285

Ser Thr Ala Leu Leu Phe Leu Leu Phe Phe Leu Thr Leu Arg Phe Ser
290                 295                 300

Val Val Lys Arg Gly Arg Lys Lys Leu Leu Tyr Ile Phe Lys Gln Pro
305                 310                 315                 320

Phe Met Arg Pro Val Gln Thr Thr Gln Glu Glu Asp Gly Cys Ser Cys
                325                 330                 335

Arg Phe Pro Glu Glu Glu Glu Gly Gly Cys Glu Leu Arg Val Lys Phe
                340                 345                 350

Ser Arg Ser Ala Asp Ala Pro Ala Tyr Gln Gln Gly Gln Asn Gln Leu
                355                 360                 365

Tyr Asn Glu Leu Asn Leu Gly Arg Arg Glu Glu Tyr Asp Val Leu Asp
                370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
                420                 425                 430

Gly His Asp Gly Leu Tyr Gln Gly Leu Ser Thr Ala Thr Lys Asp Thr
                435                 440                 445

Tyr Asp Ala Leu His Met Gln Ala Leu Pro Pro Arg
450                 455                 460

<210> SEQ ID NO 50
```

<211> LENGTH: 486
<212> TYPE: PRT
<213> ORGANISM: Artificial sequence
<220> FEATURE:
<223> OTHER INFORMATION: M195-3

<400> SEQUENCE: 50

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Thr Phe Thr Asp Tyr Asn Met His Trp Val Lys Gln Ser His Gly Lys
    50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

Gln Gly Thr Ser Val Thr Val Ser Ser Gly Gly Gly Ser Gly Gly
130                 135                 140

Gly Gly Ser Gly Gly Gly Ser Asp Ile Val Leu Thr Gln Ser Pro
145                 150                 155                 160

Ala Ser Leu Ala Val Ser Leu Gly Gln Arg Ala Thr Ile Ser Cys Arg
            165                 170                 175

Ala Ser Glu Ser Val Asp Asn Tyr Gly Ile Ser Phe Met Asn Trp Phe
        180                 185                 190

Gln Gln Lys Pro Gly Gln Pro Pro Lys Leu Leu Ile Tyr Ala Ala Ser
    195                 200                 205

Asn Gln Gly Ser Gly Val Pro Ala Arg Phe Ser Gly Ser Gly Ser Gly
210                 215                 220

Thr Asp Phe Ser Leu Asn Ile His Pro Met Glu Glu Asp Asp Thr Ala
225                 230                 235                 240

Met Tyr Phe Cys Gln Gln Ser Lys Glu Val Pro Trp Thr Phe Gly Gly
                245                 250                 255

Gly Thr Lys Leu Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380
```

```
Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 51
<211> LENGTH: 489
<212> TYPE: PRT
<213> ORGANISM: Artificial sequence
<220> FEATURE:
<223> OTHER INFORMATION: M195-4

<400> SEQUENCE: 51

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
                20                  25                  30

Val Lys Pro Gly Ala Ser Val Lys Ile Ser Cys Lys Ala Ser Gly Tyr
            35                  40                  45

Thr Phe Thr Asp Tyr Asn Met His Trp Val Lys Gln Ser His Gly Lys
    50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

Gln Gly Thr Ser Val Thr Val Ser Ser Gly Gly Gly Ser Gly Gly
    130                 135                 140

Gly Gly Ser Gly Gly Gly Ser Asp Ile Val Leu Thr Gln Ser Pro
145                 150                 155                 160

Ala Ser Leu Ala Val Ser Leu Gly Gln Arg Ala Thr Ile Ser Cys Arg
                165                 170                 175

Ala Ser Glu Ser Val Asp Asn Tyr Gly Ile Ser Phe Met Asn Trp Phe
            180                 185                 190

Gln Gln Lys Pro Gly Gln Pro Pro Lys Leu Leu Ile Tyr Ala Ala Ser
        195                 200                 205

Asn Gln Gly Ser Gly Val Pro Ala Arg Phe Ser Gly Ser Gly Ser Gly
    210                 215                 220

Thr Asp Phe Ser Leu Asn Ile His Pro Met Glu Glu Asp Asp Thr Ala
225                 230                 235                 240

Met Tyr Phe Cys Gln Gln Ser Lys Glu Val Pro Trp Thr Phe Gly Gly
                245                 250                 255
```

Gly Thr Lys Leu Glu Ile Lys Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Ile Ser Phe Phe Leu Ala Leu Thr Ser Thr Ala
305                 310                 315                 320

Leu Leu Phe Leu Leu Phe Phe Leu Thr Leu Arg Phe Ser Val Val Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 52
<211> LENGTH: 672
<212> TYPE: PRT
<213> ORGANISM: Artificial sequence
<220> FEATURE:
<223> OTHER INFORMATION: M195-5

<400> SEQUENCE: 52

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Thr Phe Thr Asp Tyr Asn Met His Trp Val Lys Gln Ser His Gly Lys
    50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

```
Gln Gly Thr Ser Val Thr Val Ser Ser Gly Gly Gly Ser Gly Gly
        130                 135                 140
Gly Gly Ser Gly Gly Gly Ser Asp Ile Val Leu Thr Gln Ser Pro
145                 150                 155                 160
Ala Ser Leu Ala Val Ser Leu Gly Gln Arg Ala Thr Ile Ser Cys Arg
                165                 170                 175
Ala Ser Glu Ser Val Asp Asn Tyr Gly Ile Ser Phe Met Asn Trp Phe
            180                 185                 190
Gln Gln Lys Pro Gly Gln Pro Pro Lys Leu Leu Ile Tyr Ala Ala Ser
        195                 200                 205
Asn Gln Gly Ser Gly Val Pro Ala Arg Phe Ser Gly Ser Gly Ser Gly
    210                 215                 220
Thr Asp Phe Ser Leu Asn Ile His Pro Met Glu Glu Asp Asp Thr Ala
225                 230                 235                 240
Met Tyr Phe Cys Gln Gln Ser Lys Glu Val Pro Trp Thr Phe Gly Gly
                245                 250                 255
Gly Thr Lys Leu Glu Ile Lys Glu Pro Lys Ser Pro Asp Lys Thr His
            260                 265                 270
Thr Cys Pro Pro Cys Pro Ala Pro Pro Val Ala Gly Pro Ser Val Phe
        275                 280                 285
Leu Phe Pro Pro Lys Pro Lys Asp Thr Leu Met Ile Ala Arg Thr Pro
    290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
    370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
        435                 440                 445
Gly Ser Phe Phe Leu Tyr Ser Lys Leu Thr Val Asp Lys Ser Arg Trp
    450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys Ile Tyr
                485                 490                 495
Ile Trp Ala Pro Leu Ala Gly Thr Cys Gly Val Leu Leu Leu Ser Leu
            500                 505                 510
Val Ile Thr Leu Tyr Cys Lys Arg Gly Arg Lys Lys Leu Leu Tyr Ile
        515                 520                 525
Phe Lys Gln Pro Phe Met Arg Pro Val Gln Thr Thr Gln Glu Glu Asp
    530                 535                 540
```

```
Gly Cys Ser Cys Arg Phe Pro Glu Glu Glu Gly Gly Cys Glu Leu
545                 550                 555                 560

Arg Val Lys Phe Ser Arg Ser Ala Asp Ala Pro Ala Tyr Gln Gln Gly
                565                 570                 575

Gln Asn Gln Leu Tyr Asn Glu Leu Asn Leu Gly Arg Arg Glu Glu Tyr
            580                 585                 590

Asp Val Leu Asp Lys Arg Arg Gly Arg Asp Pro Glu Met Gly Gly Lys
        595                 600                 605

Pro Arg Arg Lys Asn Pro Gln Glu Gly Leu Tyr Asn Glu Leu Gln Lys
    610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
                645                 650                 655

Thr Lys Asp Thr Tyr Asp Ala Leu His Met Gln Ala Leu Pro Pro Arg
            660                 665                 670
```

```
<210> SEQ ID NO 53
<211> LENGTH: 675
<212> TYPE: PRT
<213> ORGANISM: Artificial sequence
<220> FEATURE:
<223> OTHER INFORMATION: M195-6

<400> SEQUENCE: 53
```

```
Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Thr Phe Thr Asp Tyr Asn Met His Trp Val Lys Gln Ser His Gly Lys
    50                  55                  60

Ser Leu Glu Trp Ile Gly Tyr Ile Tyr Pro Tyr Asn Gly Gly Thr Gly
65                  70                  75                  80

Tyr Asn Gln Lys Phe Lys Ser Lys Ala Thr Leu Thr Val Asp Asn Ser
                85                  90                  95

Ser Ser Thr Ala Tyr Met Asp Val Arg Ser Leu Thr Ser Glu Asp Ser
            100                 105                 110

Ala Val Tyr Tyr Cys Ala Arg Gly Arg Pro Ala Met Asp Tyr Trp Gly
        115                 120                 125

Gln Gly Thr Ser Val Thr Val Ser Ser Gly Gly Gly Gly Ser Gly Gly
    130                 135                 140

Gly Gly Ser Gly Gly Gly Gly Ser Asp Ile Val Leu Thr Gln Ser Pro
145                 150                 155                 160

Ala Ser Leu Ala Val Ser Leu Gly Gln Arg Ala Thr Ile Ser Cys Arg
                165                 170                 175

Ala Ser Glu Ser Val Asp Asn Tyr Gly Ile Ser Phe Met Asn Trp Phe
            180                 185                 190

Gln Gln Lys Pro Gly Gln Pro Pro Lys Leu Leu Ile Tyr Ala Ala Ser
        195                 200                 205

Asn Gln Gly Ser Gly Val Pro Ala Arg Phe Ser Gly Ser Gly Ser Gly
    210                 215                 220

Thr Asp Phe Ser Leu Asn Ile His Pro Met Glu Glu Asp Asp Thr Ala
225                 230                 235                 240
```

```
Met Tyr Phe Cys Gln Gln Ser Lys Glu Val Pro Trp Thr Phe Gly Gly
                245                 250                 255
Gly Thr Lys Leu Glu Ile Lys Glu Pro Lys Ser Pro Asp Lys Thr His
            260                 265                 270
Thr Cys Pro Pro Cys Pro Ala Pro Pro Val Ala Gly Pro Ser Val Phe
        275                 280                 285
Leu Phe Pro Pro Lys Pro Lys Asp Thr Leu Met Ile Ala Arg Thr Pro
290                 295                 300
Glu Val Thr Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
        435                 440                 445
Gly Ser Phe Phe Leu Tyr Ser Lys Leu Thr Val Asp Lys Ser Arg Trp
450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys Ile Ile
                485                 490                 495
Ser Phe Phe Leu Ala Leu Thr Ser Thr Ala Leu Leu Phe Leu Leu Phe
            500                 505                 510
Phe Leu Thr Leu Arg Phe Ser Val Val Lys Arg Gly Arg Lys Lys Leu
        515                 520                 525
Leu Tyr Ile Phe Lys Gln Pro Phe Met Arg Pro Val Gln Thr Thr Gln
530                 535                 540
Glu Glu Asp Gly Cys Ser Cys Arg Phe Pro Glu Glu Glu Glu Gly Gly
545                 550                 555                 560
Cys Glu Leu Arg Val Lys Phe Ser Arg Ser Ala Asp Ala Pro Ala Tyr
                565                 570                 575
Gln Gln Gly Gln Asn Gln Leu Tyr Asn Glu Leu Asn Leu Gly Arg Arg
            580                 585                 590
Glu Glu Tyr Asp Val Leu Asp Lys Arg Arg Gly Arg Asp Pro Glu Met
        595                 600                 605
Gly Gly Lys Pro Arg Arg Lys Asn Pro Gln Glu Gly Leu Tyr Asn Glu
610                 615                 620
Leu Gln Lys Asp Lys Met Ala Glu Ala Tyr Ser Glu Ile Gly Met Lys
625                 630                 635                 640
Gly Glu Arg Arg Arg Gly Lys Gly His Asp Gly Leu Tyr Gln Gly Leu
                645                 650                 655
Ser Thr Ala Thr Lys Asp Thr Tyr Asp Ala Leu His Met Gln Ala Leu
```

Pro Pro Arg
        675

<210> SEQ ID NO 54
<211> LENGTH: 455
<212> TYPE: PRT
<213> ORGANISM: Artificial sequence
<220> FEATURE:
<223> OTHER INFORMATION: m2H12-1

<400> SEQUENCE: 54

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Arg Pro Gly Thr Phe Val Lys Ile Ser Cys Lys Ala Ser Gly Tyr
        35                  40                  45

Thr Phe Thr Asn Tyr Asp Ile Asn Trp Val Asn Gln Arg Pro Gly Gln
    50                  55                  60

Gly Leu Glu Trp Ile Gly Trp Ile Tyr Pro Gly Asp Gly Ser Thr Lys
65                  70                  75                  80

Tyr Asn Glu Lys Phe Lys Ala Lys Ala Thr Leu Thr Ala Asp Lys Ser
                85                  90                  95

Ser Ser Thr Ala Tyr Leu Gln Leu Asn Asn Leu Thr Ser Glu Asn Ser
            100                 105                 110

Ala Val Tyr Phe Cys Ala Ser Gly Tyr Glu Asp Ala Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Asp Ile Lys Met Thr Gln Ser
145                 150                 155                 160

Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
            180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
    210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
                245                 250                 255

Leu Glu Leu Lys Arg Gly Leu Ala Val Ser Thr Ile Ser Ser Phe Phe
            260                 265                 270

Pro Pro Gly Tyr Gln Ile Tyr Ile Trp Ala Pro Leu Ala Gly Thr Cys
        275                 280                 285

Gly Val Leu Leu Leu Ser Leu Val Ile Thr Leu Tyr Cys Lys Arg Gly
    290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
                325                 330                 335

Glu Glu Gly Gly Cys Glu Leu Arg Val Lys Phe Ser Arg Ser Ala Asp

```
                340                 345                 350
Ala Pro Ala Tyr Gln Gly Gln Asn Gln Leu Tyr Asn Glu Leu Asn
            355                 360                 365

Leu Gly Arg Arg Glu Tyr Asp Val Leu Asp Lys Arg Arg Gly Arg
        370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
        435                 440                 445

Met Gln Ala Leu Pro Pro Arg
    450                 455

<210> SEQ ID NO 55
<211> LENGTH: 458
<212> TYPE: PRT
<213> ORGANISM: Artificial sequence
<220> FEATURE:
<223> OTHER INFORMATION: m2H12-2

<400> SEQUENCE: 55

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Arg Pro Gly Thr Phe Val Lys Ile Ser Cys Lys Ala Ser Gly Tyr
        35                  40                  45

Thr Phe Thr Asn Tyr Asp Ile Asn Trp Val Asn Gln Arg Pro Gly Gln
    50                  55                  60

Gly Leu Glu Trp Ile Gly Trp Ile Tyr Pro Gly Asp Gly Ser Thr Lys
65                  70                  75                  80

Tyr Asn Glu Lys Phe Lys Ala Lys Ala Thr Leu Thr Ala Asp Lys Ser
                85                  90                  95

Ser Ser Thr Ala Tyr Leu Gln Leu Asn Asn Leu Thr Ser Glu Asn Ser
            100                 105                 110

Ala Val Tyr Phe Cys Ala Ser Gly Tyr Glu Asp Ala Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Asp Ile Lys Met Thr Gln Ser
145                 150                 155                 160

Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
            180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
    210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
```

```
                       245                 250                 255
Leu Glu Leu Lys Arg Gly Leu Ala Val Ser Thr Ile Ser Ser Phe Phe
            260                 265                 270

Pro Pro Gly Tyr Gln Ile Ile Ser Phe Phe Leu Ala Leu Thr Ser Thr
            275                 280                 285

Ala Leu Leu Phe Leu Leu Phe Phe Leu Thr Leu Arg Phe Ser Val Val
            290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
            370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
            450                 455

<210> SEQ ID NO 56
<211> LENGTH: 484
<212> TYPE: PRT
<213> ORGANISM: Artificial sequence
<220> FEATURE:
<223> OTHER INFORMATION: m2H12-3

<400> SEQUENCE: 56

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Arg Pro Gly Thr Phe Val Lys Ile Ser Cys Lys Ala Ser Gly Tyr
        35                  40                  45

Thr Phe Thr Asn Tyr Asp Ile Asn Trp Val Asn Gln Arg Pro Gly Gln
    50                  55                  60

Gly Leu Glu Trp Ile Gly Trp Ile Tyr Pro Gly Asp Gly Ser Thr Lys
65                  70                  75                  80

Tyr Asn Glu Lys Phe Lys Ala Lys Ala Thr Leu Thr Ala Asp Lys Ser
                85                  90                  95

Ser Ser Thr Ala Tyr Leu Gln Leu Asn Asn Leu Thr Ser Glu Asn Ser
            100                 105                 110

Ala Val Tyr Phe Cys Ala Ser Gly Tyr Glu Asp Ala Met Asp Tyr Trp
            115                 120                 125

Gly Gln Gly Thr Ser Val Thr Val Ser Ser Gly Gly Gly Gly Ser Gly
            130                 135                 140

Gly Gly Gly Ser Gly Gly Gly Gly Ser Asp Ile Lys Met Thr Gln Ser
```

```
                145                 150                 155                 160
Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
            180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
    210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
                245                 250                 255

Leu Glu Leu Lys Arg Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 57
<211> LENGTH: 487
<212> TYPE: PRT
<213> ORGANISM: Artificial sequence
<220> FEATURE:
<223> OTHER INFORMATION: m2H12-4

<400> SEQUENCE: 57

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30
```

```
Val Arg Pro Gly Thr Phe Val Lys Ile Ser Cys Lys Ala Ser Gly Tyr
         35                  40                  45

Thr Phe Thr Asn Tyr Asp Ile Asn Trp Val Asn Gln Arg Pro Gly Gln
 50                  55                  60

Gly Leu Glu Trp Ile Gly Trp Ile Tyr Pro Gly Asp Gly Ser Thr Lys
 65                  70                  75                  80

Tyr Asn Glu Lys Phe Lys Ala Lys Ala Thr Leu Thr Ala Asp Lys Ser
                 85                  90                  95

Ser Ser Thr Ala Tyr Leu Gln Leu Asn Asn Leu Thr Ser Glu Asn Ser
                100                 105                 110

Ala Val Tyr Phe Cys Ala Ser Gly Tyr Glu Asp Ala Met Asp Tyr Trp
                115                 120                 125

Gly Gln Gly Thr Ser Val Thr Val Ser Ser Gly Gly Gly Gly Ser Gly
        130                 135                 140

Gly Gly Gly Ser Gly Gly Gly Ser Asp Ile Lys Met Thr Gln Ser
145                 150                 155                 160

Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
        180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
        210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
                245                 250                 255

Leu Glu Leu Lys Arg Thr Thr Thr Pro Ala Pro Arg Pro Pro Thr Pro
        260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
        290                 295                 300

Cys Asp Ile Ile Ser Phe Phe Leu Ala Leu Thr Ser Thr Ala Leu Leu
305                 310                 315                 320

Phe Leu Leu Phe Phe Leu Thr Leu Arg Phe Ser Val Val Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
        370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
        435                 440                 445
```

Ile Gly Met Lys Gly Glu Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 58
<211> LENGTH: 670
<212> TYPE: PRT
<213> ORGANISM: Artificial sequence
<220> FEATURE:
<223> OTHER INFORMATION: m2H12-5

<400> SEQUENCE: 58

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
                20                  25                  30

Val Arg Pro Gly Thr Phe Val Lys Ile Ser Cys Lys Ala Ser Gly Tyr
            35                  40                  45

Thr Phe Thr Asn Tyr Asp Ile Asn Trp Val Asn Gln Arg Pro Gly Gln
    50                  55                  60

Gly Leu Glu Trp Ile Gly Trp Ile Tyr Pro Gly Asp Gly Ser Thr Lys
65                  70                  75                  80

Tyr Asn Glu Lys Phe Lys Ala Lys Ala Thr Leu Thr Ala Asp Lys Ser
                85                  90                  95

Ser Ser Thr Ala Tyr Leu Gln Leu Asn Asn Leu Thr Ser Glu Asn Ser
            100                 105                 110

Ala Val Tyr Phe Cys Ala Ser Gly Tyr Glu Asp Ala Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Asp Ile Lys Met Thr Gln Ser
145                 150                 155                 160

Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
            180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
    210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
                245                 250                 255

Leu Glu Leu Lys Arg Glu Pro Lys Ser Pro Asp Lys Thr His Thr Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
            325                 330                 335

Arg Glu Glu Gln Tyr Asn Ser Thr Tyr Arg Val Val Ser Val Leu Thr
        340                 345                 350

Val Leu His Gln Asp Trp Leu Asn Gly Lys Glu Tyr Lys Cys Lys Val
    355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Tyr Ile Trp
                485                 490                 495

Ala Pro Leu Ala Gly Thr Cys Gly Val Leu Leu Leu Ser Leu Val Ile
            500                 505                 510

Thr Leu Tyr Cys Lys Arg Gly Arg Lys Lys Leu Leu Tyr Ile Phe Lys
        515                 520                 525

Gln Pro Phe Met Arg Pro Val Gln Thr Thr Gln Glu Glu Asp Gly Cys
    530                 535                 540

Ser Cys Arg Phe Pro Glu Glu Glu Glu Gly Gly Cys Glu Leu Arg Val
545                 550                 555                 560

Lys Phe Ser Arg Ser Ala Asp Ala Pro Ala Tyr Gln Gln Gly Gln Asn
                565                 570                 575

Gln Leu Tyr Asn Glu Leu Asn Leu Gly Arg Arg Glu Glu Tyr Asp Val
            580                 585                 590

Leu Asp Lys Arg Arg Gly Arg Asp Pro Glu Met Gly Gly Lys Pro Arg
        595                 600                 605

Arg Lys Asn Pro Gln Glu Gly Leu Tyr Asn Glu Leu Gln Lys Asp Lys
    610                 615                 620

Met Ala Glu Ala Tyr Ser Glu Ile Gly Met Lys Gly Glu Arg Arg Arg
625                 630                 635                 640

Gly Lys Gly His Asp Gly Leu Tyr Gln Gly Leu Ser Thr Ala Thr Lys
                645                 650                 655

Asp Thr Tyr Asp Ala Leu His Met Gln Ala Leu Pro Pro Arg
            660                 665                 670

<210> SEQ ID NO 59
<211> LENGTH: 673
<212> TYPE: PRT
<213> ORGANISM: Artificial sequence
<220> FEATURE:
<223> OTHER INFORMATION: m2H12-6

<400> SEQUENCE: 59

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
                20                  25                  30

Val Arg Pro Gly Thr Phe Val Lys Ile Ser Cys Lys Ala Ser Gly Tyr
            35                  40                  45

Thr Phe Thr Asn Tyr Asp Ile Asn Trp Val Asn Gln Arg Pro Gly Gln
        50                  55                  60

Gly Leu Glu Trp Ile Gly Trp Ile Tyr Pro Gly Asp Gly Ser Thr Lys
65                  70                  75                  80

Tyr Asn Glu Lys Phe Lys Ala Lys Ala Thr Leu Thr Ala Asp Lys Ser
                85                  90                  95

Ser Ser Thr Ala Tyr Leu Gln Leu Asn Asn Leu Thr Ser Glu Asn Ser
            100                 105                 110

Ala Val Tyr Phe Cys Ala Ser Gly Tyr Glu Asp Ala Met Asp Tyr Trp
        115                 120                 125

Gly Gln Gly Thr Ser Val Thr Val Ser Ser Gly Gly Gly Gly Ser Gly
        130                 135                 140

Gly Gly Gly Ser Gly Gly Gly Ser Asp Ile Lys Met Thr Gln Ser
145                 150                 155                 160

Pro Ser Ser Met Tyr Ala Ser Leu Gly Glu Arg Val Ile Ile Asn Cys
                165                 170                 175

Lys Ala Ser Gln Asp Ile Asn Ser Tyr Leu Ser Trp Phe Gln Gln Lys
            180                 185                 190

Pro Gly Lys Ser Pro Lys Thr Leu Ile Tyr Arg Ala Asn Arg Leu Val
        195                 200                 205

Asp Gly Val Pro Ser Arg Phe Ser Gly Ser Gly Ser Gly Gln Asp Tyr
210                 215                 220

Ser Leu Thr Ile Ser Ser Leu Glu Tyr Glu Asp Met Gly Ile Tyr Tyr
225                 230                 235                 240

Cys Leu Gln Tyr Asp Glu Phe Pro Leu Thr Phe Gly Ala Gly Thr Lys
                245                 250                 255

Leu Glu Leu Lys Arg Glu Pro Lys Ser Pro Asp Lys Thr His Thr Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser

```
                    435                 440                 445
Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys Ile Ile Ser Phe
                485                 490                 495

Phe Leu Ala Leu Thr Ser Thr Ala Leu Leu Phe Leu Leu Phe Phe Leu
                500                 505                 510

Thr Leu Arg Phe Ser Val Val Lys Arg Gly Arg Lys Lys Leu Leu Tyr
            515                 520                 525

Ile Phe Lys Gln Pro Phe Met Arg Pro Val Gln Thr Thr Gln Glu Glu
        530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
    610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 60
<211> LENGTH: 465
<212> TYPE: PRT
<213> ORGANISM: Artificial sequence
<220> FEATURE:
<223> OTHER INFORMATION: DRB2-1

<400> SEQUENCE: 60

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Glu Leu
                20                  25                  30

Val Lys Pro Gly Ala Ser Val Lys Met Ser Cys Lys Ala Ser Gly Tyr
            35                  40                  45

Lys Phe Thr Asp Tyr Val Val His Trp Leu Lys Gln Lys Pro Gly Gln
        50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Val Ser Ser Leu Thr Ser Glu Asp Ser
            100                 105                 110

Ala Val Tyr Tyr Cys Ala Arg Asp Tyr Arg Tyr Glu Val Tyr Gly Met
        115                 120                 125
```

```
Asp Tyr Trp Gly Gln Gly Thr Ser Val Thr Val Ser Gly Gly Gly
        130                 135                 140
Gly Ser Gly Gly Gly Gly Ser Gly Gly Gly Ser Asp Ile Val Leu
145                 150                 155                 160
Thr Gln Ser Pro Thr Ile Met Ser Ala Ser Pro Gly Glu Arg Val Thr
                165                 170                 175
Met Thr Cys Thr Ala Ser Ser Ser Val Asn Tyr Ile His Trp Tyr Gln
                180                 185                 190
Gln Lys Ser Gly Asp Ser Pro Leu Arg Trp Ile Phe Asp Thr Ser Lys
        195                 200                 205
Val Ala Ser Gly Val Pro Ala Arg Phe Ser Gly Ser Gly Ser Gly Thr
    210                 215                 220
Ser Tyr Ser Leu Thr Ile Ser Thr Met Glu Ala Glu Asp Ala Ala Thr
225                 230                 235                 240
Tyr Tyr Cys Gln Gln Trp Arg Ser Tyr Pro Leu Thr Phe Gly Asp Gly
                245                 250                 255
Thr Arg Leu Glu Leu Lys Arg Ala Asp Ala Ala Pro Thr Val Ser Gly
                260                 265                 270
Leu Ala Val Ser Thr Ile Ser Ser Phe Phe Pro Pro Gly Tyr Gln Ile
        275                 280                 285
Tyr Ile Trp Ala Pro Leu Ala Gly Thr Cys Gly Val Leu Leu Leu Ser
290                 295                 300
Leu Val Ile Thr Leu Tyr Cys Lys Arg Gly Arg Lys Lys Leu Leu Tyr
305                 310                 315                 320
Ile Phe Lys Gln Pro Phe Met Arg Pro Val Gln Thr Thr Gln Glu Glu
                325                 330                 335
Asp Gly Cys Ser Cys Arg Phe Pro Glu Glu Glu Glu Gly Gly Cys Glu
                340                 345                 350
Leu Arg Val Lys Phe Ser Arg Ser Ala Asp Ala Pro Ala Tyr Gln Gln
        355                 360                 365
Gly Gln Asn Gln Leu Tyr Asn Glu Leu Asn Leu Gly Arg Arg Glu Glu
    370                 375                 380
Tyr Asp Val Leu Asp Lys Arg Gly Arg Asp Pro Glu Met Gly Gly
385                 390                 395                 400
Lys Pro Arg Arg Lys Asn Pro Gln Glu Gly Leu Tyr Asn Glu Leu Gln
                405                 410                 415
Lys Asp Lys Met Ala Glu Ala Tyr Ser Glu Ile Gly Met Lys Gly Glu
                420                 425                 430
Arg Arg Arg Gly Lys Gly His Asp Gly Leu Tyr Gln Gly Leu Ser Thr
        435                 440                 445
Ala Thr Lys Asp Thr Tyr Asp Ala Leu His Met Gln Ala Leu Pro Pro
    450                 455                 460
Arg
465

<210> SEQ ID NO 61
<211> LENGTH: 468
<212> TYPE: PRT
<213> ORGANISM: Artificial sequence
<220> FEATURE:
<223> OTHER INFORMATION: DRB2-2

<400> SEQUENCE: 61

Met Ala Leu Pro Val Thr Ala Leu Leu Leu Pro Leu Ala Leu Leu Leu
1               5                   10                  15
```

```
His Ala Ala Arg Pro Glu Val Lys Leu Gln Glu Ser Gly Pro Glu Leu
            20                  25                  30

Val Lys Pro Gly Ala Ser Val Lys Met Ser Cys Lys Ala Ser Gly Tyr
        35                  40                  45

Lys Phe Thr Asp Tyr Val Val His Trp Leu Lys Gln Lys Pro Gly Gln
50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Val Ser Ser Leu Thr Ser Glu Asp Ser
            100                 105                 110

Ala Val Tyr Tyr Cys Ala Arg Asp Tyr Arg Tyr Glu Val Tyr Gly Met
        115                 120                 125

Asp Tyr Trp Gly Gln Gly Thr Ser Val Thr Val Ser Ser Gly Gly Gly
130                 135                 140

Gly Ser Gly Gly Gly Gly Ser Gly Gly Gly Gly Ser Asp Ile Val Leu
145                 150                 155                 160

Thr Gln Ser Pro Thr Ile Met Ser Ala Ser Pro Gly Glu Arg Val Thr
                165                 170                 175

Met Thr Cys Thr Ala Ser Ser Ser Val Asn Tyr Ile His Trp Tyr Gln
            180                 185                 190

Gln Lys Ser Gly Asp Ser Pro Leu Arg Trp Ile Phe Asp Thr Ser Lys
        195                 200                 205

Val Ala Ser Gly Val Pro Ala Arg Phe Ser Gly Ser Gly Ser Gly Thr
        210                 215                 220

Ser Tyr Ser Leu Thr Ile Ser Thr Met Glu Ala Glu Asp Ala Ala Thr
225                 230                 235                 240

Tyr Tyr Cys Gln Gln Trp Arg Ser Tyr Pro Leu Thr Phe Gly Asp Gly
            245                 250                 255

Thr Arg Leu Glu Leu Lys Arg Ala Asp Ala Ala Pro Thr Val Ser Gly
            260                 265                 270

Leu Ala Val Ser Thr Ile Ser Ser Phe Phe Pro Pro Gly Tyr Gln Ile
            275                 280                 285

Ile Ser Phe Phe Leu Ala Leu Thr Ser Thr Ala Leu Leu Phe Leu Leu
290                 295                 300

Phe Phe Leu Thr Leu Arg Phe Ser Val Val Lys Arg Gly Arg Lys Lys
305                 310                 315                 320

Leu Leu Tyr Ile Phe Lys Gln Pro Phe Met Arg Pro Val Gln Thr Thr
            325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
        370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
            420                 425                 430
```

Lys Gly Glu Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 62
<211> LENGTH: 494
<212> TYPE: PRT
<213> ORGANISM: Artificial sequence
<220> FEATURE:
<223> OTHER INFORMATION: DRB2-3

<400> SEQUENCE: 62

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Glu Leu
            20                  25                  30

Val Lys Pro Gly Ala Ser Val Lys Met Ser Cys Lys Ala Ser Gly Tyr
        35                  40                  45

Lys Phe Thr Asp Tyr Val Val His Trp Leu Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Val Ser Ser Leu Thr Ser Glu Asp Ser
            100                 105                 110

Ala Val Tyr Tyr Cys Ala Arg Asp Tyr Arg Tyr Glu Val Tyr Gly Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Leu
145                 150                 155                 160

Thr Gln Ser Pro Thr Ile Met Ser Ala Ser Pro Gly Glu Arg Val Thr
                165                 170                 175

Met Thr Cys Thr Ala Ser Ser Ser Val Asn Tyr Ile His Trp Tyr Gln
            180                 185                 190

Gln Lys Ser Gly Asp Ser Pro Leu Arg Trp Ile Phe Asp Thr Ser Lys
        195                 200                 205

Val Ala Ser Gly Val Pro Ala Arg Phe Ser Gly Ser Gly Ser Gly Thr
    210                 215                 220

Ser Tyr Ser Leu Thr Ile Ser Thr Met Glu Ala Glu Asp Ala Ala Thr
225                 230                 235                 240

Tyr Tyr Cys Gln Gln Trp Arg Ser Tyr Pro Leu Thr Phe Gly Asp Gly
                245                 250                 255

Thr Arg Leu Glu Leu Lys Arg Ala Asp Ala Ala Pro Thr Val Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

-continued

```
Ala Pro Leu Ala Gly Thr Cys Gly Val Leu Leu Ser Leu Val Ile
                325                 330                 335

Thr Leu Tyr Cys Lys Arg Gly Arg Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
    435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 63
<211> LENGTH: 497
<212> TYPE: PRT
<213> ORGANISM: Artificial sequence
<220> FEATURE:
<223> OTHER INFORMATION: DRB2-4

<400> SEQUENCE: 63

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Glu Leu
            20                  25                  30

Val Lys Pro Gly Ala Ser Val Lys Met Ser Cys Lys Ala Ser Gly Tyr
        35                  40                  45

Lys Phe Thr Asp Tyr Val Val His Trp Leu Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Val Ser Ser Leu Thr Ser Glu Asp Ser
            100                 105                 110

Ala Val Tyr Tyr Cys Ala Arg Asp Tyr Arg Tyr Glu Val Tyr Gly Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Leu
145                 150                 155                 160

Thr Gln Ser Pro Thr Ile Met Ser Ala Ser Pro Gly Glu Arg Val Thr
                165                 170                 175

Met Thr Cys Thr Ala Ser Ser Ser Val Asn Tyr Ile His Trp Tyr Gln
            180                 185                 190
```

-continued

```
Gln Lys Ser Gly Asp Ser Pro Leu Arg Trp Ile Phe Asp Thr Ser Lys
            195                 200                 205

Val Ala Ser Gly Val Pro Ala Arg Phe Ser Gly Ser Gly Ser Gly Thr
210                 215                 220

Ser Tyr Ser Leu Thr Ile Ser Thr Met Glu Ala Glu Asp Ala Ala Thr
225                 230                 235                 240

Tyr Tyr Cys Gln Gln Trp Arg Ser Tyr Pro Leu Thr Phe Gly Asp Gly
            245                 250                 255

Thr Arg Leu Glu Leu Lys Arg Ala Asp Ala Ala Pro Thr Val Ser Thr
            260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
            290                 295                 300

Ala Val His Thr Arg Gly Leu Asp Phe Ala Cys Asp Ile Ile Ser Phe
305                 310                 315                 320

Phe Leu Ala Leu Thr Ser Thr Ala Leu Leu Phe Leu Leu Phe Phe Leu
            325                 330                 335

Thr Leu Arg Phe Ser Val Val Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Gly Gly Cys Glu
            370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
            405                 410                 415

Tyr Asp Val Leu Asp Lys Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

Arg
```

<210> SEQ ID NO 64
<211> LENGTH: 680
<212> TYPE: PRT
<213> ORGANISM: Artificial sequence
<220> FEATURE:
<223> OTHER INFORMATION: DRB2-5

<400> SEQUENCE: 64

```
Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Glu Leu
            20                  25                  30

Val Lys Pro Gly Ala Ser Val Lys Met Ser Cys Lys Ala Ser Gly Tyr
            35                  40                  45

Lys Phe Thr Asp Tyr Val Val His Trp Leu Lys Gln Lys Pro Gly Gln
```

```
                50                  55                  60
Gly Leu Glu Trp Ile Gly Tyr Ile Asn Pro Tyr Asn Asp Gly Thr Lys
 65                  70                  75                  80

Tyr Asn Glu Lys Phe Lys Gly Lys Ala Thr Leu Thr Ser Asp Lys Ser
                     85                  90                  95

Ser Ser Thr Ala Tyr Met Glu Val Ser Ser Leu Thr Ser Glu Asp Ser
                100                 105                 110

Ala Val Tyr Tyr Cys Ala Arg Asp Tyr Arg Tyr Glu Val Tyr Gly Met
                115                 120                 125

Asp Tyr Trp Gly Gln Gly Thr Ser Val Thr Val Ser Ser Gly Gly Gly
            130                 135                 140

Gly Ser Gly Gly Gly Gly Ser Gly Gly Gly Gly Ser Asp Ile Val Leu
145                 150                 155                 160

Thr Gln Ser Pro Thr Ile Met Ser Ala Ser Pro Gly Glu Arg Val Thr
                    165                 170                 175

Met Thr Cys Thr Ala Ser Ser Ser Val Asn Tyr Ile His Trp Tyr Gln
                180                 185                 190

Gln Lys Ser Gly Asp Ser Pro Leu Arg Trp Ile Phe Asp Thr Ser Lys
            195                 200                 205

Val Ala Ser Gly Val Pro Ala Arg Phe Ser Gly Ser Gly Ser Gly Thr
210                 215                 220

Ser Tyr Ser Leu Thr Ile Ser Thr Met Glu Ala Glu Asp Ala Ala Thr
225                 230                 235                 240

Tyr Tyr Cys Gln Gln Trp Arg Ser Tyr Pro Leu Thr Phe Gly Asp Gly
                245                 250                 255

Thr Arg Leu Glu Leu Lys Arg Ala Asp Ala Ala Pro Thr Val Ser Glu
                260                 265                 270

Pro Lys Ser Pro Asp Lys Thr His Thr Cys Pro Pro Cys Pro Ala Pro
            275                 280                 285

Pro Val Ala Gly Pro Ser Val Phe Leu Phe Pro Pro Lys Pro Lys Asp
            290                 295                 300

Thr Leu Met Ile Ala Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
                340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
            450                 455                 460

Leu Thr Val Asp Lys Ser Arg Trp Gln Gln Gly Asn Val Phe Ser Cys
465                 470                 475                 480
```

```
Ser Val Met His Glu Ala Leu His Asn His Tyr Thr Gln Lys Ser Leu
            485                 490                 495

Ser Leu Ser Pro Gly Lys Ile Tyr Ile Trp Ala Pro Leu Ala Gly Thr
            500                 505                 510

Cys Gly Val Leu Leu Ser Leu Val Ile Thr Leu Tyr Cys Lys Arg
            515                 520                 525

Gly Arg Lys Lys Leu Leu Tyr Ile Phe Lys Gln Pro Phe Met Arg Pro
            530                 535                 540

Val Gln Thr Thr Gln Glu Glu Asp Gly Cys Ser Cys Arg Phe Pro Glu
545                 550                 555                 560

Glu Glu Glu Gly Gly Cys Glu Leu Arg Val Lys Phe Ser Arg Ser Ala
            565                 570                 575

Asp Ala Pro Ala Tyr Gln Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
            595                 600                 605

Arg Asp Pro Glu Met Gly Gly Lys Pro Arg Arg Lys Asn Pro Gln Glu
            610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
            645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
            675                 680

<210> SEQ ID NO 65
<211> LENGTH: 683
<212> TYPE: PRT
<213> ORGANISM: Artificial sequence
<220> FEATURE:
<223> OTHER INFORMATION: DRB2-6

<400> SEQUENCE: 65

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Glu Leu
            20                  25                  30

Val Lys Pro Gly Ala Ser Val Lys Met Ser Cys Lys Ala Ser Gly Tyr
            35                  40                  45

Lys Phe Thr Asp Tyr Val Val His Trp Leu Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
            85                  90                  95

Ser Ser Thr Ala Tyr Met Glu Val Ser Ser Leu Thr Ser Glu Asp Ser
            100                 105                 110

Ala Val Tyr Tyr Cys Ala Arg Asp Tyr Arg Tyr Glu Val Tyr Gly Met
            115                 120                 125

Asp Tyr Trp Gly Gln Gly Thr Ser Val Thr Val Ser Ser Gly Gly Gly
            130                 135                 140

Gly Ser Gly Gly Gly Gly Ser Gly Gly Gly Gly Ser Asp Ile Val Leu
145                 150                 155                 160
```

```
Thr Gln Ser Pro Thr Ile Met Ser Ala Ser Pro Gly Glu Arg Val Thr
            165                 170                 175

Met Thr Cys Thr Ala Ser Ser Ser Val Asn Tyr Ile His Trp Tyr Gln
            180                 185                 190

Gln Lys Ser Gly Asp Ser Pro Leu Arg Trp Ile Phe Asp Thr Ser Lys
            195                 200                 205

Val Ala Ser Gly Val Pro Ala Arg Phe Ser Gly Ser Gly Ser Gly Thr
210                 215                 220

Ser Tyr Ser Leu Thr Ile Ser Thr Met Glu Ala Glu Asp Ala Ala Thr
225                 230                 235                 240

Tyr Tyr Cys Gln Gln Trp Arg Ser Tyr Pro Leu Thr Phe Gly Asp Gly
            245                 250                 255

Thr Arg Leu Glu Leu Lys Arg Ala Asp Ala Ala Pro Thr Val Ser Glu
            260                 265                 270

Pro Lys Ser Pro Asp Lys Thr His Thr Cys Pro Pro Cys Pro Ala Pro
            275                 280                 285

Pro Val Ala Gly Pro Ser Val Phe Leu Phe Pro Pro Lys Pro Lys Asp
            290                 295                 300

Thr Leu Met Ile Ala Arg Thr Pro Glu Val Thr Cys Val Val Val Asp
305                 310                 315                 320

Val Ser His Glu Asp Pro Glu Val Lys Phe Asn Trp Tyr Val Asp Gly
            325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Ala Leu Pro
370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
            405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
            435                 440                 445

Thr Pro Pro Val Leu Asp Ser Asp Gly Ser Phe Phe Leu Tyr Ser Lys
450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
            485                 490                 495

Ser Leu Ser Pro Gly Lys Ile Ile Ser Phe Phe Leu Ala Leu Thr Ser
            500                 505                 510

Thr Ala Leu Leu Phe Leu Leu Phe Phe Leu Thr Leu Arg Phe Ser Val
            515                 520                 525

Val Lys Arg Gly Arg Lys Lys Leu Leu Tyr Ile Phe Lys Gln Pro Phe
530                 535                 540

Met Arg Pro Val Gln Thr Thr Gln Glu Glu Asp Gly Cys Ser Cys Arg
545                 550                 555                 560

Phe Pro Glu Glu Glu Glu Gly Gly Cys Glu Leu Arg Val Lys Phe Ser
            565                 570                 575
```

```
Arg Ser Ala Asp Ala Pro Ala Tyr Gln Gly Gln Asn Gln Leu Tyr
                580                 585                 590

Asn Glu Leu Asn Leu Gly Arg Arg Glu Tyr Asp Val Leu Asp Lys
            595                 600                 605

Arg Arg Gly Arg Asp Pro Glu Met Gly Gly Lys Pro Arg Arg Lys Asn
610                 615                 620

Pro Gln Glu Gly Leu Tyr Asn Glu Leu Gln Lys Asp Lys Met Ala Glu
625                 630                 635                 640

Ala Tyr Ser Glu Ile Gly Met Lys Gly Glu Arg Arg Arg Gly Lys Gly
                645                 650                 655

His Asp Gly Leu Tyr Gln Gly Leu Ser Thr Ala Thr Lys Asp Thr Tyr
                660                 665                 670

Asp Ala Leu His Met Gln Ala Leu Pro Pro Arg
            675                 680

<210> SEQ ID NO 66
<211> LENGTH: 461
<212> TYPE: PRT
<213> ORGANISM: Artificial sequence
<220> FEATURE:
<223> OTHER INFORMATION: My9.6-1

<400> SEQUENCE: 66

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
                20                  25                  30

Val Lys Pro Gly Ala Ser Val Lys Met Ser Cys Lys Ala Ser Gly Tyr
            35                  40                  45

Thr Phe Thr Ser Tyr Tyr Ile His Trp Ile Lys Gln Thr Pro Gly Gln
        50                  55                  60

Gly Leu Glu Trp Val Gly Val Ile Tyr Pro Gly Asn Asp Asp Ile Ser
65                  70                  75                  80

Tyr Asn Gln Lys Phe Lys Gly Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Ser Asn Ile Met Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Val Phe Phe Ser Ser Ser Gln Lys Asn Tyr
            180                 185                 190

Leu Ala Trp Tyr Gln Gln Ile Pro Gly Gln Ser Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
225                 230                 235                 240

Glu Asp Leu Ala Ile Tyr Tyr Cys His Gln Tyr Leu Ser Ser Arg Thr
                245                 250                 255
```

```
Phe Gly Gly Gly Thr Lys Leu Glu Ile Lys Arg Gly Leu Ala Val Ser
                260                 265                 270

Thr Ile Ser Ser Phe Pro Pro Gly Tyr Gln Ile Tyr Ile Trp Ala
            275                 280                 285

Pro Leu Ala Gly Thr Cys Gly Val Leu Leu Ser Leu Val Ile Thr
        290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Gly Gly Cys Glu Leu Arg Val Lys
            340                 345                 350

Phe Ser Arg Ser Ala Asp Ala Pro Ala Tyr Gln Gln Gly Gln Asn Gln
                355                 360                 365

Leu Tyr Asn Glu Leu Asn Leu Gly Arg Arg Glu Glu Tyr Asp Val Leu
            370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
                435                 440                 445

Thr Tyr Asp Ala Leu His Met Gln Ala Leu Pro Pro Arg
450                 455                 460

<210> SEQ ID NO 67
<211> LENGTH: 464
<212> TYPE: PRT
<213> ORGANISM: Artificial sequence
<220> FEATURE:
<223> OTHER INFORMATION: My9.6-2

<400> SEQUENCE: 67

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
                20                  25                  30

Val Lys Pro Gly Ala Ser Val Lys Met Ser Cys Lys Ala Ser Gly Tyr
            35                  40                  45

Thr Phe Thr Ser Tyr Tyr Ile His Trp Ile Lys Gln Thr Pro Gly Gln
    50                  55                  60

Gly Leu Glu Trp Val Gly Val Ile Tyr Pro Gly Asn Asp Asp Ile Ser
65                  70                  75                  80

Tyr Asn Gln Lys Phe Lys Gly Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Gly Ser Asn Ile Met Leu Thr Gln
145                 150                 155                 160
```

Ser Pro Ser Ser Leu Ala Val Ser Ala Gly Glu Lys Val Thr Met Ser
            165                 170                 175

Cys Lys Ser Ser Gln Ser Val Phe Phe Ser Ser Ser Lys Asn Tyr
        180                 185                 190

Leu Ala Trp Tyr Gln Gln Ile Pro Gly Gln Ser Pro Lys Leu Leu Ile
            195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
225                 230                 235                 240

Glu Asp Leu Ala Ile Tyr Tyr Cys His Gln Tyr Leu Ser Ser Arg Thr
                245                 250                 255

Phe Gly Gly Gly Thr Lys Leu Glu Ile Lys Arg Gly Leu Ala Val Ser
            260                 265                 270

Thr Ile Ser Ser Phe Phe Pro Gly Tyr Gln Ile Ile Ser Phe Phe
            275                 280                 285

Leu Ala Leu Thr Ser Thr Ala Leu Leu Phe Leu Leu Phe Phe Leu Thr
            290                 295                 300

Leu Arg Phe Ser Val Val Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
            355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
            435                 440                 445

Thr Lys Asp Thr Tyr Asp Ala Leu His Met Gln Ala Leu Pro Pro Arg
    450                 455                 460

<210> SEQ ID NO 68
<211> LENGTH: 490
<212> TYPE: PRT
<213> ORGANISM: Artificial sequence
<220> FEATURE:
<223> OTHER INFORMATION: My9.6-3

<400> SEQUENCE: 68

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
            20                  25                  30

Val Lys Pro Gly Ala Ser Val Lys Met Ser Cys Lys Ala Ser Gly Tyr
        35                  40                  45

Thr Phe Thr Ser Tyr Tyr Ile His Trp Ile Lys Gln Thr Pro Gly Gln
    50                  55                  60

```
Gly Leu Glu Trp Val Gly Val Ile Tyr Pro Gly Asn Asp Asp Ile Ser
 65                  70                  75                  80

Tyr Asn Gln Lys Phe Lys Gly Lys Ala Thr Leu Thr Ala Asp Lys Ser
                 85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Ser Asn Ile Met Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Val Phe Phe Ser Ser Ser Gln Lys Asn Tyr
            180                 185                 190

Leu Ala Trp Tyr Gln Gln Ile Pro Gly Gln Ser Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
225                 230                 235                 240

Glu Asp Leu Ala Ile Tyr Tyr Cys His Gln Tyr Leu Ser Ser Arg Thr
                245                 250                 255

Phe Gly Gly Gly Thr Lys Leu Glu Ile Lys Arg Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
```

-continued

```
                485                 490
```

<210> SEQ ID NO 69
<211> LENGTH: 493
<212> TYPE: PRT
<213> ORGANISM: Artificial sequence
<220> FEATURE:
<223> OTHER INFORMATION: My9.6-4

<400> SEQUENCE: 69

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
            20                  25                  30

Val Lys Pro Gly Ala Ser Val Lys Met Ser Cys Lys Ala Ser Gly Tyr
        35                  40                  45

Thr Phe Thr Ser Tyr Tyr Ile His Trp Ile Lys Gln Thr Pro Gly Gln
    50                  55                  60

Gly Leu Glu Trp Val Gly Val Ile Tyr Pro Gly Asn Asp Asp Ile Ser
65                  70                  75                  80

Tyr Asn Gln Lys Phe Lys Gly Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Ser Asn Ile Met Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Val Phe Phe Ser Ser Ser Gln Lys Asn Tyr
            180                 185                 190

Leu Ala Trp Tyr Gln Gln Ile Pro Gly Gln Ser Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
225                 230                 235                 240

Glu Asp Leu Ala Ile Tyr Tyr Cys His Gln Tyr Leu Ser Ser Arg Thr
                245                 250                 255

Phe Gly Gly Gly Thr Lys Leu Glu Ile Lys Arg Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Ile Ser Phe Leu Ala Leu
305                 310                 315                 320

Thr Ser Thr Ala Leu Leu Phe Leu Leu Phe Phe Leu Thr Leu Arg Phe
                325                 330                 335

Ser Val Val Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
```

-continued

```
              355                 360                 365
Cys Arg Phe Pro Glu Glu Glu Gly Gly Cys Glu Leu Arg Val Lys
            370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 70
<211> LENGTH: 676
<212> TYPE: PRT
<213> ORGANISM: Artificial sequence
<220> FEATURE:
<223> OTHER INFORMATION: My9.6-5

<400> SEQUENCE: 70

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
            20                  25                  30

Val Lys Pro Gly Ala Ser Val Lys Met Ser Cys Lys Ala Ser Gly Tyr
        35                  40                  45

Thr Phe Thr Ser Tyr Tyr Ile His Trp Ile Lys Gln Thr Pro Gly Gln
    50                  55                  60

Gly Leu Glu Trp Val Gly Val Ile Tyr Pro Gly Asn Asp Asp Ile Ser
65                  70                  75                  80

Tyr Asn Gln Lys Phe Lys Gly Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Ser Asn Ile Met Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Val Phe Phe Ser Ser Gln Lys Asn Tyr
            180                 185                 190

Leu Ala Trp Tyr Gln Gln Ile Pro Gly Gln Ser Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
```

```
            225                 230                 235                 240
        Glu Asp Leu Ala Ile Tyr Tyr Cys His Gln Tyr Leu Ser Ser Arg Thr
                            245                 250                 255
        Phe Gly Gly Gly Thr Lys Leu Glu Ile Lys Arg Glu Pro Lys Ser Pro
                            260                 265                 270
        Asp Lys Thr His Thr Cys Pro Pro Cys Pro Ala Pro Val Ala Gly
                        275                 280                 285
        Pro Ser Val Phe Leu Phe Pro Pro Lys Pro Lys Asp Thr Leu Met Ile
                    290                 295                 300
        Ala Arg Thr Pro Glu Val Thr Cys Val Val Val Asp Val Ser His Glu
        305                 310                 315                 320
        Asp Pro Glu Val Lys Phe Asn Trp Tyr Val Asp Gly Val Glu Val His
                                325                 330                 335
        Asn Ala Lys Thr Lys Pro Arg Glu Glu Gln Tyr Asn Ser Thr Tyr Arg
                        340                 345                 350
        Val Val Ser Val Leu Thr Val Leu His Gln Asp Trp Leu Asn Gly Lys
                    355                 360                 365
        Glu Tyr Lys Cys Lys Val Ser Asn Lys Ala Leu Pro Ala Pro Ile Glu
                370                 375                 380
        Lys Thr Ile Ser Lys Ala Lys Gly Gln Pro Arg Glu Pro Gln Val Tyr
        385                 390                 395                 400
        Thr Leu Pro Pro Ser Arg Asp Glu Leu Thr Lys Asn Gln Val Ser Leu
                            405                 410                 415
        Thr Cys Leu Val Lys Gly Phe Tyr Pro Ser Asp Ile Ala Val Glu Trp
                        420                 425                 430
        Glu Ser Asn Gly Gln Pro Glu Asn Asn Tyr Lys Thr Thr Pro Pro Val
                    435                 440                 445
        Leu Asp Ser Asp Gly Ser Phe Phe Leu Tyr Ser Lys Leu Thr Val Asp
                450                 455                 460
        Lys Ser Arg Trp Gln Gln Gly Asn Val Phe Ser Cys Ser Val Met His
        465                 470                 475                 480
        Glu Ala Leu His Asn His Tyr Thr Gln Lys Ser Leu Ser Leu Ser Pro
                            485                 490                 495
        Gly Lys Ile Tyr Ile Trp Ala Pro Leu Ala Gly Thr Cys Gly Val Leu
                        500                 505                 510
        Leu Leu Ser Leu Val Ile Thr Leu Tyr Cys Lys Arg Gly Arg Lys Lys
                    515                 520                 525
        Leu Leu Tyr Ile Phe Lys Gln Pro Phe Met Arg Pro Val Gln Thr Thr
                530                 535                 540
        Gln Glu Glu Asp Gly Cys Ser Cys Arg Phe Pro Glu Glu Glu Glu Gly
        545                 550                 555                 560
        Gly Cys Glu Leu Arg Val Lys Phe Ser Arg Ser Ala Asp Ala Pro Ala
                            565                 570                 575
        Tyr Gln Gln Gly Gln Asn Gln Leu Tyr Asn Glu Leu Asn Leu Gly Arg
                        580                 585                 590
        Arg Glu Glu Tyr Asp Val Leu Asp Lys Arg Arg Gly Arg Asp Pro Glu
                    595                 600                 605
        Met Gly Gly Lys Pro Arg Arg Lys Asn Pro Gln Glu Gly Leu Tyr Asn
                610                 615                 620
        Glu Leu Gln Lys Asp Lys Met Ala Glu Ala Tyr Ser Glu Ile Gly Met
        625                 630                 635                 640
        Lys Gly Glu Arg Arg Arg Gly Lys Gly His Asp Gly Leu Tyr Gln Gly
                            645                 650                 655
```

Leu Ser Thr Ala Thr Lys Asp Thr Tyr Asp Ala Leu His Met Gln Ala
            660                 665                 670

Leu Pro Pro Arg
        675

<210> SEQ ID NO 71
<211> LENGTH: 679
<212> TYPE: PRT
<213> ORGANISM: Artificial sequence
<220> FEATURE:
<223> OTHER INFORMATION: My9.6-6

<400> SEQUENCE: 71

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Val
            20                  25                  30

Val Lys Pro Gly Ala Ser Val Lys Met Ser Cys Lys Ala Ser Gly Tyr
        35                  40                  45

Thr Phe Thr Ser Tyr Tyr Ile His Trp Ile Lys Gln Thr Pro Gly Gln
    50                  55                  60

Gly Leu Glu Trp Val Gly Val Ile Tyr Pro Gly Asn Asp Asp Ile Ser
65                  70                  75                  80

Tyr Asn Gln Lys Phe Lys Gly Lys Ala Thr Leu Thr Ala Asp Lys Ser
                85                  90                  95

Ser Thr Thr Ala Tyr Met Gln Leu Ser Ser Leu Thr Ser Glu Asp Ser
            100                 105                 110

Ala Val Tyr Tyr Cys Ala Arg Glu Val Arg Leu Arg Tyr Phe Asp Val
        115                 120                 125

Trp Gly Ala Gly Thr Thr Val Thr Val Ser Ser Gly Gly Gly Gly Ser
    130                 135                 140

Gly Gly Gly Gly Ser Gly Gly Gly Ser Asn Ile Met Leu Thr Gln
145                 150                 155                 160

Ser Pro Ser Ser Leu Ala Val Ser Ala Gly Glu Lys Val Thr Met Ser
                165                 170                 175

Cys Lys Ser Ser Gln Ser Val Phe Phe Ser Ser Ser Gln Lys Asn Tyr
            180                 185                 190

Leu Ala Trp Tyr Gln Gln Ile Pro Gly Gln Ser Pro Lys Leu Leu Ile
        195                 200                 205

Tyr Trp Ala Ser Thr Arg Glu Ser Gly Val Pro Asp Arg Phe Thr Gly
    210                 215                 220

Ser Gly Ser Gly Thr Asp Phe Thr Leu Thr Ile Ser Ser Val Gln Ser
225                 230                 235                 240

Glu Asp Leu Ala Ile Tyr Tyr Cys His Gln Tyr Leu Ser Ser Arg Thr
                245                 250                 255

Phe Gly Gly Gly Thr Lys Leu Glu Ile Lys Arg Glu Pro Lys Ser Pro
            260                 265                 270

Asp Lys Thr His Thr Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ala Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

```
Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
            355                 360                 365

Glu Tyr Lys Cys Lys Val Ser Asn Lys Ala Leu Pro Ala Pro Ile Glu
            370                 375                 380

Lys Thr Ile Ser Lys Ala Lys Gly Gln Pro Arg Glu Pro Gln Val Tyr
385                 390                 395                 400

Thr Leu Pro Pro Ser Arg Asp Glu Leu Thr Lys Asn Gln Val Ser Leu
            405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
            435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
            485                 490                 495

Gly Lys Ile Ile Ser Phe Phe Leu Ala Leu Thr Ser Thr Ala Leu Leu
            500                 505                 510

Phe Leu Leu Phe Phe Leu Thr Leu Arg Phe Ser Val Val Lys Arg Gly
            515                 520                 525

Arg Lys Lys Leu Leu Tyr Ile Phe Lys Gln Pro Phe Met Arg Pro Val
            530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
                565                 570                 575

Ala Pro Ala Tyr Gln Gln Gly Gln Asn Gln Leu Tyr Asn Glu Leu Asn
            580                 585                 590

Leu Gly Arg Arg Glu Glu Tyr Asp Val Leu Asp Lys Arg Arg Gly Arg
            595                 600                 605

Asp Pro Glu Met Gly Gly Lys Pro Arg Arg Lys Asn Pro Gln Glu Gly
            610                 615                 620

Leu Tyr Asn Glu Leu Gln Lys Asp Lys Met Ala Glu Ala Tyr Ser Glu
625                 630                 635                 640

Ile Gly Met Lys Gly Glu Arg Arg Arg Gly Lys Gly His Asp Gly Leu
                645                 650                 655

Tyr Gln Gly Leu Ser Thr Ala Thr Lys Asp Thr Tyr Asp Ala Leu His
            660                 665                 670

Met Gln Ala Leu Pro Pro Arg
            675

<210> SEQ ID NO 72
<211> LENGTH: 44
<212> TYPE: DNA
<213> ORGANISM: Artificial sequence
<220> FEATURE:
<223> OTHER INFORMATION: TALEN1_CD33_Exon3

<400> SEQUENCE: 72
tgcatcccct ctttctcctc actagacttg acccacaggc ccaa                    44
```

<210> SEQ ID NO 73
<211> LENGTH: 49
<212> TYPE: DNA
<213> ORGANISM: Artificial sequence
<220> FEATURE:
<223> OTHER INFORMATION: TALEN2_CD33_Exon3

<400> SEQUENCE: 73
ttctcctcac tagacttgac ccacaggccc aaaatcctca tccctggca        49

<210> SEQ ID NO 74
<211> LENGTH: 49
<212> TYPE: DNA
<213> ORGANISM: Artificial sequence
<220> FEATURE:
<223> OTHER INFORMATION: TALEN1_CD33_Exon4

<400> SEQUENCE: 74
tcctctccta gatgttccac agaacccaac aactggtatc tttccagga        49

<210> SEQ ID NO 75
<211> LENGTH: 44
<212> TYPE: DNA
<213> ORGANISM: Artificial sequence
<220> FEATURE:
<223> OTHER INFORMATION: TALEN2_CD33_Exon4

<400> SEQUENCE: 75
tcctagatgt tccacagaac ccaacaactg gtatctttcc agga        44

<210> SEQ ID NO 76
<211> LENGTH: 17
<212> TYPE: DNA
<213> ORGANISM: Artificial sequence
<220> FEATURE:
<223> OTHER INFORMATION: Sequence bound by TALEN1 Left exon 3

<400> SEQUENCE: 76
tgcatcccct ctttctc        17

<210> SEQ ID NO 77
<211> LENGTH: 17
<212> TYPE: DNA
<213> ORGANISM: Artificial sequence
<220> FEATURE:
<223> OTHER INFORMATION: Sequence bound by TALEN2 Left exon 3

<400> SEQUENCE: 77
ttctcctcac tagactt        17

<210> SEQ ID NO 78
<211> LENGTH: 17
<212> TYPE: DNA
<213> ORGANISM: Artificial sequence
<220> FEATURE:
<223> OTHER INFORMATION: Sequence bound by TALEN1 Left exon 4

<400> SEQUENCE: 78
tcctctccta gatgttc        17

<210> SEQ ID NO 79
<211> LENGTH: 17
<212> TYPE: DNA
<213> ORGANISM: Artificial sequence
<220> FEATURE:
<223> OTHER INFORMATION: Sequence bound by TALEN2 Left exon 4

<400> SEQUENCE: 79
tcctagatgt tccacag                                                    17

<210> SEQ ID NO 80
<211> LENGTH: 10
<212> TYPE: DNA
<213> ORGANISM: Artificial sequence
<220> FEATURE:
<223> OTHER INFORMATION: spacer 1 (Exon3)

<400> SEQUENCE: 80
ctcactagac                                                            10

<210> SEQ ID NO 81
<211> LENGTH: 15
<212> TYPE: DNA
<213> ORGANISM: Artificial sequence
<220> FEATURE:
<223> OTHER INFORMATION: spacer2 (Exon3)

<400> SEQUENCE: 81
gacccacagg cccaa                                                      15

<210> SEQ ID NO 82
<211> LENGTH: 15
<212> TYPE: DNA
<213> ORGANISM: Artificial sequence
<220> FEATURE:
<223> OTHER INFORMATION: spacer 1 (Exon4)

<400> SEQUENCE: 82
cacagaaccc aacaa                                                      15

<210> SEQ ID NO 83
<211> LENGTH: 10
<212> TYPE: DNA
<213> ORGANISM: Artificial sequence
<220> FEATURE:
<223> OTHER INFORMATION: spacer 2 (Exon4)

<400> SEQUENCE: 83
aacccaacaa                                                            10

<210> SEQ ID NO 84
<211> LENGTH: 17
<212> TYPE: DNA
<213> ORGANISM: Artificial sequence
<220> FEATURE:
<223> OTHER INFORMATION: Sequence bound by TALEN1 right exon 3

<400> SEQUENCE: 84
ttgacccaca ggcccaa                                                    17

<210> SEQ ID NO 85
<211> LENGTH: 17
<212> TYPE: DNA
<213> ORGANISM: Artificial sequence
<220> FEATURE:
<223> OTHER INFORMATION: Sequence bound by TALEN2 right exon 3

<400> SEQUENCE: 85
aatcctcatc cctggca                                                    17

<210> SEQ ID NO 86

```
<211> LENGTH: 17
<212> TYPE: DNA
<213> ORGANISM: Artificial sequence
<220> FEATURE:
<223> OTHER INFORMATION: Sequence bound by TALEN1 right exon 4

<400> SEQUENCE: 86
ctggtatctt tccagga                                                   17

<210> SEQ ID NO 87
<211> LENGTH: 17
<212> TYPE: DNA
<213> ORGANISM: Artificial sequence
<220> FEATURE:
<223> OTHER INFORMATION: Sequence bound by TALEN2 right exon 4

<400> SEQUENCE: 87
ctggtatctt tccagga                                                   17
```